(12) United States Patent
Takeuchi et al.

(10) Patent No.: US 10,619,140 B2
(45) Date of Patent: Apr. 14, 2020

(54) COMPOSITIONS AND METHODS FOR THE TREATMENT OF HEMOGLOBINOPATHIES

(71) Applicant: FRED HUTCHINSON CANCER RESEARCH CENTER, Seattle, WA (US)

(72) Inventors: Ryo Takeuchi, Seattle, WA (US); Mark T Groudine, Seattle, WA (US); Barry L. Stoddard, Seattle, WA (US); Michael A Bender, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 15/461,091

(22) Filed: Mar. 16, 2017

(65) Prior Publication Data

US 2017/0298329 A1    Oct. 19, 2017

Related U.S. Application Data

(62) Division of application No. 14/380,935, filed as application No. PCT/US2013/027459 on Feb. 22, 2013, now abandoned.

(60) Provisional application No. 61/603,231, filed on Feb. 24, 2012.

(51) Int. Cl.
| | | |
|---|---|---|
| *C12N 9/22* | (2006.01) | |
| *A61K 38/46* | (2006.01) | |
| *C12N 9/16* | (2006.01) | |

(52) U.S. Cl.
CPC .............. *C12N 9/22* (2013.01); *A61K 38/465* (2013.01); *C12N 9/16* (2013.01); *C07K 2319/80* (2013.01)

(58) Field of Classification Search
CPC .................................................. C12N 15/1037
See application file for complete search history.

(56) References Cited

U.S. PATENT DOCUMENTS

| | | |
|---|---|---|
| 2002/0182673 A1 | 12/2002 | Chen et al. |
| 2006/0206949 A1 | 9/2006 | Arnould |
| 2009/0220476 A1 | 9/2009 | Paques |
| 2009/0271881 A1 | 10/2009 | Arnould |
| 2010/0086533 A1 | 4/2010 | Montaya |
| 2011/0182867 A1 | 7/2011 | Orkin et al. |
| 2012/0276074 A1* | 11/2012 | Scharenberg .......... A61K 38/45 424/94.2 |
| 2014/0148361 A1 | 5/2014 | Stoddard et al. |
| 2015/0166969 A1 | 6/2015 | Takeuchi et al. |

FOREIGN PATENT DOCUMENTS

| | | |
|---|---|---|
| CN | 101802184 A | 8/2010 |
| JP | 2010-534070 A | 11/2010 |
| WO | WO 2009/013559 A1 | 1/2009 |
| WO | WO 2009/013622 A2 | 1/2009 |
| WO | WO 2010/030963 A2 | 3/2010 |
| WO | WO 2011/156430 A2 | 12/2011 |
| WO | WO 2013/126794 A1 | 8/2013 |
| WO | WO 2014/036219 A2 | 3/2014 |

OTHER PUBLICATIONS

Zou, et al., "Site-specific gene correction of a point mutation in human iPS cells derived from an adult patient with sickle cell disease." Blood (2011); 118 (17): 4599-4608.
Baxter et al., "Engineering domain fusion chimeras from I-Onul family LAGLIDADG homing endonucleases", Nucl. Acids Res. (2012); 401(16): 7985-8000.
Beard et al., "Efficient and stable MGMT-mediated selection of long-term repopulating stem cells in nonhuman primates", J. Clin. Invest. (2010); 120(7): 2345-2354.
Bender et al., "β-globin Gene Switching and DNase I Sensitivity of the Endogenous β-globin Locus in Mice Do Not Require the Locus Control Region", Mol. Cell. (2000); 5(2): 387-393.
Boitano et al., "Aryl hydrocarbon receptor antagonists promote the expansion of human hematopoietic stem cells", Science (2011); 329(5997): 1345-1348.
Brunstein et al., "Allogeneic hematopoietic cell transplantation for hematologic malignancy: relative risks and benefits of double umbilical cord blood", Blood (2010); 116(22): 4693-4699.
Butler et al., "Endothelial cells are essential for the self-renewal and repopulation of Notch-dependent hematopoietic stem cells", Cell Stem Cell (2011); 6(3): 251-264.
Cermak et al., "Efficient design and assembly of custom TALEN and other TAL effector-based constructs for DNA targeting", Nucl. Acids Res. (2011); 39(12): e82-e82.
Certo et al., "Tracking genome engineering outcome at individual DNA breakpoints", Nat Methods (2011); 8(8): 671-676.
Chen et al., "High-frequency genome editing using ssDNA oligonucleotides with zinc-finger nucleases", Nat. Methods (2011); 8(9): 753-755.
Cong et al., "Multiplex genome engineering using CRISPR/Cas systems", Science, 2013; 339(6121): 819-23. doi: 10.1126/science. 1231143. Epub Jan. 3, 2013.
Dahlberg et al., "Ex vivo expansion of human hematopoietic stem and progenitor cells", Blood (2010); 117(23): 6083-6090.

(Continued)

*Primary Examiner* — Karen Cochrane Carlson
(74) *Attorney, Agent, or Firm* — Cooley LLP

(57) ABSTRACT

Provided are compositions and methods for the treatment of hemoglobinopathies such as thalassemias and sickle cell disease. Compositions and methods include one or more endonuclease(s) or endonuclease fusion protein(s), including one or more homing endonuclease(s) and/or homing endonuclease fusion protein(s) and/or CRISPR endonuclease(s) and/or CRISPR endonuclease fusion protein(s): (a) to disrupt a Bcl11a coding region; (b) to disrupt a Bcl11a gene regulatory region; (c) to modify an adult human β-globin locus; (d) to disrupt a HbF silencing DNA regulatory element or pathway, such as a Bcl11a-regulated HbF silencing region; (e) to mutate one or more γ-globin gene promoter(s) to achieve increased expression of a γ-globin gene; (f) to mutate one or more δ-globin gene promoter(s) to achieve increased expression of a δ-globin gene; and/or (g) to correct one or more β-globin gene mutation(s).

9 Claims, 46 Drawing Sheets

Specification includes a Sequence Listing.

(56) References Cited

OTHER PUBLICATIONS

Delaney et al., "Notch-mediated expansion of human cord blood progenitor cells capable of rapid myeloid reconstitution", Nat Med (2010); 16(2): 232-236.
Doyon et al., "Directed Evolution and Substrate Specificity Profile of Homing Endonuclease I-SceI", J. Am. Chem. Soc. (2006); 128(7): 2477-2484.
European Patent Application No. 13751886.6, Partial European Search Report dated Nov. 23, 2015, 5 pages.
European Patent Application No. 13751886.6, Extended European Search Report dated Mar. 10, 2016, 9 pages.
Forget, "Molecular Basis of Hereditary Persistence of Fetal Hemoglobin", Ann. NY Acad. Sci. (1998); 850: 38-44.
Galanello et al., "Amelioration of Sardinian $\beta^0$ thalassemia by genetic modifiers", Blood (2009); 114(18): 3935-3937.
Giarratana et al., "Ex vivo generation of fully mature human red blood cells from hematopoietic stem cells", Nat. Biotechnol. (2005); 23(1): 69-74.
Gooley et al., "Reduced mortality after allogenetic hematopoietic-cell transplantation", N. Engl. J. Med. (2011); 363(22): 2091-101.
International Application No. PCT/US2013/027459, International Preliminary Report on Patentability dated Aug. 26, 2014, 10 pages.
International Application No. PCT/US2013/027459, International Search Report and Written Opinion dated Jun. 26, 2013, 15 pages.
Jacoby, K., "Expanding LAGLIDADG endonuclease scaffold diversity by rapidly surveying evolutionary sequence space", Nucleic Acid Research, 2012; 40 (11): 4954-4964. Published online Feb. 14, 2012.
Jarjour et al., "High-resolution profiling of homing endonuclease binding and catalytic specificity using yeast surface display", Nucleic Acids Res (2009); 37(20): 6871-80.
Jinek et al., "A programmable dual-RNA-guided DNA endonuclease in adaptive bacterial immunity", Science, 2012; 337(6096): 816-821. doi: 10.1126/science.1225829. Epub Jun. 28, 2012.
Mak et al., "The crystal structure of TAL effector PthXo1 bound to its DNA target", Science (2012); 335(6069): 716-719.
Mali et al., "RNA-Guided Human Genome Engineering via Cas9", Science, 2013; 339: 823-826.
Munoz et al., "Molecular basis of engineered meganuclease targeting of the endogenous human RAG1 locus", Nucleic Acids Res. (2011); 39(2): 729-743.
Offner et al., "Mortality hazard functions as related to neutropenia at different times after marrow transplantation", Blood (1996); 88(10): 4058-4062.
Pászty et al., "Transgenic Knockout Mice with Exclusively Human Sickle Hemoglobin and Sickle Cell Disease", Science (1997); 278(5339): 876-878.
Porcu et al., "The human β globin locus introduced by YAC transfer exhibits a specific and reproducible pattern of developmental regulation in transgenic mice", Blood (1997); 90(11): 4602-4609.
Sankaran et al., "Transcriptional silencing of fetal hemoglobin by BCL11A", Annals of the NY Academy of Sciences: Cooley's anaemia: 9th Symposium, 2010; pp. 64-68. XP002743270.
Sankaran et al., "A Functional Element Necessary for Fetal Hemoglobin Silencing", N. Engl. J. Med. (2011); 365: 807-814.
Sankaran et al., "Developmental and species-divergent globin switching are driven by BCL11A", Nature (2009); 460: 1093-1097.
Sankaran et al., "Human fetal hemoglobin expression is regulated by the developmental stage-specific repressor BCL11A", Science (2008); 322(5909): 1839-1342.
Stoddard, "Homing endonucleases: from microbial genetic invaders to reagents for targeted DNA modification", Structure (2011); 19(1): 7-15.

Sun, N., "Optimized TAL effector nucleases (TALENs) for use in treatment of sickle cell disease", Mol. BioSyst., 2012; 8: 1255-1263.
Takeuchi et al., "Optimization of in vivo activity of a bifunctional homing endonuclease and maturase reverses evolutionary degradation ", Nucl. Acids Res. (2009); 37(3):877-890.
Takeuchi et al., "Tapping natural reservoirs of homing endonucleases for targeted gene modification", Proc. Natl. Acad. Sci. U.S.A. (2011); 108(32): 13077-13082.
Taylor et al., "LAHEDES: the LAGLIDADG homing endonuclease database and engineering server", Nucl. Acids Res. (2012); 40(Web Server issue):W110-116 (2012).
Trobridge et al., "Cocal-pseudotyped Lentiviral Vectors Resist Inactivation by Human Serum and Efficiently Transduce Primate Hematopoietic Repopulating Cells", Mol. Ther. (2008); 18: 725-733.
Varnum-Finney et al., "Pluripotent, cytokine-dependent, hematopoietic stem cells are immortalized by constitutive Notch1 signaling", Nat Med (2000); 6: 1278-1281.
Wang et al., "Desmoglein 2 is a receptor for adenovirus serotypes 3, 7, 11, and 14", Nat. Med. (2011); 17(1): 96-104. Published online Dec. 12, 2010. doi: 10.1038/nm.2270.
Wang et al., "Tightly regulated gene expression in human hematopoietic stem cells after transduction with helper-dependent Ad5/35 vectors", Exp. Hematol. (2008); 36(7): 823-831.
Watts et al., "Combination of HOXB4 and Delta-1 ligand improves expansion of cord blood cells", Blood (2010); 116(26): 5859-5866.
Wilber et al., "Transcriptional regulation of fetal to adult hemoglobin switching: new therapeutic opportunities", Blood (2011); 117(15): 3945-3953.
Xu et al., "Correction of Sickle Cell Disease in Adult Mice by Interference with Fetal Hemoglobin Silencing", Science (2011); 334(6058): 993-936.
Yang et al., "A mouse model for beta 0-thalassemia", Proc. Natl. Acad. Sci. U.S.A. (1995); 92(25): 11608-11612.
Zhang et al., "Differential Effects of HOXB4 on Nonhuman Primate Short- and Long-Term Repopulating Cells", PLoS Med (2006); 3(5): e173 (2006).
Arnould et al., "Engineered I-CreI Derivatives Cleaving Sequences from the Human XPC Gene can Induce Highly Efficient Gene Correction in Mammalian Cells." Journal of Molecular Biology (2007); 371(1): 49-65.
Chen et al., "Directed evolution of homing endonuclease I-SceI with altered sequence specificity." Protein Engineering, Design and Selection (2009); 22(4): 249-256.
European Patent Application No. 17178186.7, Extended European Search Report dated Nov. 16, 2017, 7 pages.
International Preliminary Report on Patentability, dated Dec. 10, 2012, in International Patent Application No. PCT/US2011/039527, 5 pages.
International Search Report and Written Opinion, dated Feb. 23, 2012, in International Patent Application No. PCT/US2011/039527, 9 pages.
REBASE Homing Endonucleases web page, http://rebase.neb.com/cgi-bin/azlist?homing, viewed Nov. 27, 2016.
Sethuraman, J., et al., "Genes within Genes: Multiple LAGLIDADG Homing Endonucleases Target the Ribosomal Protein S3 Gene Encoded within an mI Group I Intron of Ophiostoma and Related Taxa." Molecular Biology and Evolution (2009); 26(10): 2299-2315.
Thein, "The Molecular Basis of β-Thalassemia." Cold Spring Harb Perspect Med (2013); 3: a011700, pp. 1-24.
Sebastino, V., et al., "In Situ Genetic Correction of the Sickle Cell Anemia Mutation in Human Induced Pluripotent Stem Cells Using Engineered Zinc Finger Nucleases." Stem Cells (Nov. 2011); 29(11): 1717-1726.

\* cited by examiner (SEQ ID NO: 1)

Nucleotide Sequence of a Human Fetal Hemoglobin (HbF) Silencing Region (chr11:5212342-5215944 in HG18)

| | | |
|---|---|---|
| 1 | CCAGTGAGCAGGTTGGTTTAAGATAAGCAGGGTTTCATTAGTTTGTGAGA | 50 |
| 51 | ATGAAAAATGAACCTTCATTCCACTATTCCCTTAACTTGCCCTGAGATTG | 100 |
| 101 | GCTGTTCTGTCATGTGTGTCTTGACTCAGAAACCCTGTTCTCCTCTACAT | 150 |
| 151 | ATCTCCCCACCGCATCTCTTTCAGCAGTTGTTTCTAAAAATATCCTCCTA | 200 |
| 201 | GTTTCATTTTTGCAGAAGTGTTTTAGGCTAATATAGTGGAATGTATCTTA | 250 |
| 251 | GAGTTTAACTTATTTGTTTCTGTCACTTTATACTAAGAAAACTTATCTAA | 300 |
| 301 | AAGCAGATGTTTTAACAAGTTGACTCAATATAAAGTTCTTCTTTGCCTCT | 350 |
| 351 | AGAGATTTTTGTCTCCAAGGGAATTTTGAGAGGTTGGAATGGACAAATCT | 400 |
| 401 | ATTGCTGCAGTTTAAACTTGCTTGCTTCCTCCTTCTTTTGGTAAATTCTT | 450 |
| 451 | CCTATAATAAAACTCtaattttttattatattgaaataaatatccattaa | 500 |
| 501 | aagaatatttaaaaaatGAATAGTGTTTATTTACCAGTTATTGAAATAGG | 550 |
| 551 | TTCTGGAAACATGAATTTTAAGGTTAACATTTTAATGACAGATAAAATCA | 600 |
| 601 | AATATTATATACAAATATTTTGAATGTTTAAAATTATGGTATGACTAAAG | 650 |
| 651 | AAAGAATGCAAAGTGAAAAGTAGATTTACCATATTCAGCCAGATTAAATT | 700 |
| 701 | TAACGAAGTTCCTGGGAATATGCTAGTACAGAACATTTTTACAGATGTGT | 750 |
| 751 | TCTTAAAAAAAATGTGGAATTAGACCCAGGAATGAAGATCCCAGTAGTT | 800 |
| 801 | TTTCACTCTTTTCTGAATTCAAATAATGCCACAATGGCAGACAAATACAC | 850 |
| 851 | ACCCATGAGCATATCCAAaaggaaggattgaaggaaagaggaggaagaaa | 900 |
| 901 | tggagaaaggaaggaaggaagaggggaagagagaggatggaagggatgga | 950 |
| 951 | ggagaagaaggaaAAATAAATAATGgagaggagaggagaaaaaaggaggg | 1000 |
| 1001 | gagaggagaggagaagggataggGaagagaaagagaaagggaagggaaga | 1050 |
| 1051 | gaggaaagaagagaagaggagagaaaagaaacgaagagagggGaagggaa | 1100 |
| 1101 | ggaaaaaaagaggaaaaagagacaagagaagagaTaagactgacagtt | 1150 |
| 1151 | caaattttggtggtgatatggatcaatagaaactcaaactctgttggtga | 1200 |
| 1201 | cactgtacaatagtataaccccctttggaaaacctttaatagtatccacaa | 1250 |
| 1251 | atgctggatgcttgataagtctattacctagcaattacatttttagatat | 1300 |

FIG. 6

```
1301  tcagaaacacatgcatgtgtgtatccaaagacatgtatagaaatgcttat  1350
1351  gacagcaataatcataaaaacctcaaaccggtagccacttaaatgcttac  1400
1401  caacagtagaattgataaattacggtatagtcaaagaatagaatattaca  1450
1451  cagaaatgaaaagaatcaactactgcttaacacgtagcgatacaaatgca  1500
1501  ttttacagcatttggttgattaaaagtaaccagaggtgagttcaaactat  1550
1551  atgactttatttgtatatagAAAGATGGATGATGTGCCTGAGATTCTGAT  1600
1601  CACAAGGGGAAATGTTATAAAATAGGGTAGAGAGGAGCCATGAATGACCT  1650
1651  TTAAACTTTGTTACAAGTTATTTTTCTGTAACCTggaagccaacgaaaga  1700
1701  tattgaataattcaagaaaggtggtggcatggtttgatttgtgtctttaa  1750
1751  aagattattctcacttagtgaagaaatgtatttagaagtagagaaaatg  1800
1801  ggagacaaatagctgggcttctgttgcagtaGGGAAGAAAGTGACAATGC  1850
1851  CATTTCTATTATCAGACTTGGACCATGACGGTGATGTCAGTCGTGAACAC  1900
1901  AAGAATAGGGCCACATTTGTGAGTTTAGTGGTACGATaaaatcagaaata  1950
1951  cagtcttggatacattgtattgtatgcactcttgtaaaatgcaaaaagat  2000
2001  gtacttagatatgtggatctggagctcagAAAGAATACAACCAGGTCAAG  2050
2051  AATACAGAATGGAACAGAACATACAAGAACAGATCATAATGTGCTGTGTG  2100
2101  AATCACTACCACTACCTGTTAAAAATGACAGATGATGTACTTCATcaata  2150
2151  tctccttaaaatcttagaatgtgtttgtgagggaggaattatgtttccaa  2200
2201  ttcatatataagaaaattgattctaaaaaaaatgttaggtaaattcttaa  2250
2251  ggccaTGAGGACTGTTATTTGATCTTTGTCTGTTAATTCCAAAGACTTGG  2300
2301  CTTTTCACTTTAATTCTGTTCTACCTGAAATGATTTTACACATTGGGAGA  2350
2351  TCTGGTTACATGTTTATTCTATATGGATTGCATTGAGAGGATTTGTATAA  2400
2401  CAGAATAAGGTCtttttttcttttctcttctgagatggagtttcatccct  2450
2451  attgcccaagctagagtgcaatggtgcaatctaggctcaccgcaacctct  2500
2501  gcctcctgggttcaagcaattctcctgcctcagccacctgaatagctggg  2550
2551  actgcaggcatgcaccacacgcccggctgatttgtattttagtagaga   2600
2601  tggggtttcaccatgttggtcaggctggtcttgaactcctgacctcaagt  2650
2651  gatctgcctgccttggcctcccaaagtgctgggtttacaagcctgagcca  2700
2701  ccgcatccagccAGGATAAGGTCTAAAAGTGGAAAGAATAGCATCTACTC  2750
```

FIG. 6 (Cont.)

```
2751 TTGTTCAGGAAACAATGAGGACCTGACTGGGCAGTAAGAGTGGTGATTAA 2800
2801 TAGATAGGGACAAATTGAAGCAGAATCGAACTGTTGATTAgaggtaggga 2850
2851 aatgattttaatctgtgaccttggtgaatgggcaagtagctatctaatga 2900
2901 ctaaaatggaaaacactggaagagaaacagttttagtataacaagtgaaa 2950
2951 tacccatgctgagtctgaggtgcctataggacatctatataaataagccc 3000
3001 agtacattgtttgatatatgggtttggcactgaggttggaggtcagaggt 3050
3051 tagaaatcagagttgggaattgggattatacaggctgtatttaagagttt 3100
3101 agatataactgtgaatccaagagtgtgaTGAATACAAAGTTAAATGAAGG 3150
3151 ACCTTTAATGAACACCAACATTTAATGTGAAATCTCAAGGAAGTATGAAG 3200
3201 TAAGACATAGTCCCCAAAATCCCCGATGATTTTAGAACTCAGTATCGATT 3250
3251 TTAATTAGTGTAATGCCAATGTGGGTTAGAATGGAAGTCAACTTGCTGTT 3300
3301 GGTTTCAGAGCAGGTAGGAGATAAGGTTCTAGATTTTGACACAGTGAAAA 3350
3351 GCTGAAACAAAAAGGAAAAGGTAGGGTGAAAGATGGGAAATGTATGTAAG 3400
3401 GAGGATGAGCCACATGGTATGGGAGGTATACTAAGGACTCTAGGGTCAGA 3450
3451 GAAATATGGGTTATATCCTTCTACAAAATTCACATTCTTggctgggtgtg 3500
3501 gtggctcacgcctgtgatcccagcactttcagaggccgaggagggtggat 3550
3551 cacctgatgttaggagttcgagatcagcctgaccaacatggtgaaacccc 3600
3601 cta                                                3603
```

FIG. 6 (Cont.)

(SEQ ID NO: 2)

Nucleotide Sequence of a 350 bp Portion of a Human HbF Silencing Region
(Including Sites for Bcl11a Occupancy)

| | | |
|---|---|---|
| 1 | AAAGATGGATGATGTGCCTGAGATTCTGATCACAAGGGGAAATGTTATAA | 50 |
| 51 | AATAGGGTAGAGAGGAGCCATGAATGACCTTTAAACTTTGTTACAAGTTA | 100 |
| 101 | TTTTTCTGTAACCTggaagccaacgaaagatattgaataattcaagaaag | 150 |
| 151 | gtggtggcatggtttgatttgtgtctttaaaagattattctcacttagtg | 200 |
| 201 | aagaaatgtatttagaagtagagaaaatgggagacaaatagctgggctt | 250 |
| 251 | ctgttgcagtaGGGAAGAAAGTGACAATGCCATTTCTATTATCAGACTTG | 300 |
| 301 | GACCATGACGGTGATGTCAGTCGTGAACACAAGAATAGGGCCACATTTGT | 350 |

FIG. 7

(SEQ ID NO: 13)

Human b-globin Gene from 1 kb Upstream of the
Cap Site through the PolyA Site

| 1 | GCAATGAAAATAAATGTTTTTTATTAGGCAGAATCCAGATGCTCAAGGCC | 50 |
|---|---|---|
| 51 | CTTCATAATATCCCCCAGTTTAGTAGTTGGACTTAGGGAACAAAGGAACC | 100 |
| 101 | TTTAATAGAAATTGGACAGCAAGAAAGCGAGCTTAGTGATACTTGTGGGC | 150 |
| 151 | CAGGGCATTAGCCACACCAGCCACCACTTTCTGATAGGCAGCCTGCACTG | 200 |
| 201 | GTGGGGTGAATTCTTTGCCAAAGTGATGGGCCAGCACACAGACCAGCACG | 250 |
| 251 | TTGCCCAGGAGCTGTGGGAGGAAGATAAGAGGTATGAACATGATTAGCAA | 300 |
| 301 | AAGGGCCTAGCTTGGACTCAGAATAATCCAGCCTTATCCCAACCATAAAA | 350 |
| 351 | TAAAAGCAGAATGGTAGCTGGATTGTAGCTGCTATTAGCAATATGAAACC | 400 |
| 401 | TCTTACATCAGTTACAATTTATATGCAGAAATATTTATATGCAGAGATAT | 450 |
| 451 | TGCTATTGCCTTAACCCAGAAATTATCACTGTTATTCTTTAGAATGGTGC | 500 |
| 501 | AAAGAGGCATGATACATTGTATCATTATTGCCCTGAAAGAAAGAGATTAG | 550 |
| 551 | GGAAAGTATTAGAAATAAGATAAACAAAAAGTATATTAAAAGAAGAAAG | 600 |
| 601 | CATTTTTTAAAATTACAAATGCAAaattaccctgatttggtcaatatgtg | 650 |
| 651 | tacacatattaaaacattacactttaacccataaatatgtataatgatta | 700 |
| 701 | tgtatcaattaaaaataaaaGAAAATAAAGTAGGGAGATTATGAATATGC | 750 |
| 751 | AAATAAGCACACATATATTCCAAATAGTAATGTACTAGGCAGACTGTGTA | 800 |
| 801 | AAGTTTTTTTTTAAGTTACTTAATGTATCTCAGAGATATTTCCTTTTGTT | 850 |
| 851 | ATACACAATGTTAAGGCATTAAGTATAATAGTAAAAATTGCGgagaagaa | 900 |
| 901 | aaaaaagaaagcaagaattaaacaaaagaaaacaattgttatgaacagc | 950 |
| 951 | aaataaaagaaactaaaaCGATCCTGAGACTTCCACACTGATGCAATCAT | 1000 |
| 1001 | TCGTCTGTTTCCCATTCTAAACTGTACCCTGTTACTTATCCCCTTCCTAT | 1050 |
| 1051 | GACATGAACTTAACCATAGAAAAGAAGGGGAAAGAAAACATCAAGCGTCC | 1100 |
| 1101 | CATAGACTCACCCTGAAGTTCTCAGGATCCACGTGCAGCTTGTCACAGTG | 1150 |
| 1151 | CAGCTCACTCAGTGTGGCAAAGGTGCCCTTGAGGTTGTCCAGGTGAGCCA | 1200 |
| 1201 | GGCCATCACTAAAGGCACCGAGCACTTTCTTGCCATGAGCCTTCACCTTA | 1250 |
| 1251 | GGGTTGCCCATAACAGCATCAGGAGTGGACAGATCCCCAAAGGACTCAAA | 1300 |

FIG. 8

```
1301  GAACCTCTGGGTCCAAGGGTAGACCACCAGCAGCCTAAGGGTGGGAAAAT  1350
1351  AGACCAATAGGCAGAGAGAGTCAGTGCCTATCAGAAACCCAAGAGTCTTC  1400
1401  TCTGTCTCCACATGCCCAGTTTCTATTGGTCTCCTTAAACCTGTCTTGTA  1450
1451  ACCTTGATACCAACCTGCCCAGGGCCTCACCACCAACTTCATCCACGTTC  1500
1501  ACCTTGCCCCACAGGGCAGTAACGGCAGACTTCTCCTCAGGAGTCAGATG  1550
1551  CACCATGGTGTCTGTTTGAGGTTGCTAGTGAACACAGTTGTGTCAGAAGC  1600
1601  AAATGTAAGCAATAGATGGCTCTGCCCTGACTTTTATGCCCAGCCCTGGC  1650
1651  TCCTGCCCTCCCTGCTCCTGGGAGTAGATTGGCCAACCCTAGGGTGTGGC  1700
1701  TCCACAGGGTGAGGTCTAAGTGATGACAGCCGTACCTGTCCTTGGCTCTT  1750
1751  CTGGCACTGGCTTAGGAGTTGGACTTCAAACCCTCAGCCCTCCCTCTAAG  1800
1801  ATATATCTCTTGGCCCCATACCATCAGTACAAATTGCTACTAAAAACATC  1850
1851  CTCCTTTGCAAGTGTATTTACGTAATATTTGGAAtcacagcttggtaagc  1900
1901  atattgaagatcgtttcccaattttcttattacacaaataagaagttga  1950
1951  tgcactaaaagtggaagagttttgtctaCCATAATTCAGCTTTGGGATAT  2000
2001  GTAGATGGATCTCTTCCTGCGTCTCCAGAATATGCAAAATACTTACAGGA  2050
2051  CAGAATGGATGAAAACTCTACCTCGGTTCTAAGCATATCTTCTCCTTATT  2100
2101  TGGATTAAAACCTTCTGGTAAGAAAAGAAAAAatatatatatatatgtgt  2150
2151  gtatatatacacacatacatatacatatatatGCATTCATTTGTTGTTGT  2200
2201  TTTTCTTAATTTGCTCATGCATGCTAATAAATTATGTCTAAAAATAGAAT  2250
2251  AAATACAAATCAATGTGCTCTGTGCATTAGTTACTTATTAGGTTTTGGGA  2300
2301  AACAAGAGATAAAAAACTAGAGACCTCTTAATGCAGTCAAAAATACAAAT  2350
2351  AAATAAAAAGTCACTTACAACCCAAAGTGTGACTATCAATGGGGTAATCA  2400
2401  GTGGTGTCAAATAGGAGGTTAACTGGGGACATCTAACTGTTTCTGCCTGG  2450
2451  ACTAATCTGCAAGAGTGTCTGGGGGAACAAAAAGCCTCTGTGACTTAGAA  2500
2501  AGTAGGGGTAGGAGGGGAAAAGGTCTTCTACTTGGCTCAGATTATTTTTT  2550
2551  TCCTCTAGTCCACTAAGAATACTGCGTTTTAAAATCATTTCCTTGATTCA  2600
2601  AGTTCC                                              2606
```

FIG. 8 (Cont.)

(SEQ ID NO: 14)

606 bp Region of Human b-globin Spanning from the Promoter into Intron 2
(Mutations within this Region Result in Thalassemias and Sickle Cell Disease)

```
  1  CACCCTGAAGTTCTCAGGATCCACGTGCAGCTTGTCACAGTGCAGCTCAC   50
 51  TCAGTGTGGCAAAGGTGCCCTTGAGGTTGTCCAGGTGAGCCAGGCCATCA  100
101  CTAAAGGCACCGAGCACTTTCTTGCCATGAGCCTTCACCTTAGGGTTGCC  150
151  CATAACAGCATCAGGAGTGGACAGATCCCCAAAGGACTCAAAGAACCTCT  200
201  GGGTCCAAGGGTAGACCACCAGCAGCCTAAGGGTGGGAAAATAGACCAAT  250
251  AGGCAGAGAGAGTCAGTGCCTATCAGAAACCCAAGAGTCTTCTCTGTCTC  300
301  CACATGCCCAGTTTCTATTGGTCTCCTTAAACCTGTCTTGTAACCTTGAT  350
351  ACCAACCTGCCCAGGGCCTCACCACCAACTTCATCCACGTTCACCTTGCC  400
401  CCACAGGGCAGTAACGGCAGACTTCTCCTCAGGAGTCAGATGCACCATGG  450
451  TGTCTGTTTGAGGTTGCTAGTGAACACAGTTGTGTCAGAAGCAAATGTAA  500
501  GCAATAGATGGCTCTGCCCTGACTTTTATGCCCAGCCCTGGCTCCTGCCC  550
551  TCCCTGCTCCTGGGAGTAGATTGGCCAACCCTAGGGTGTGGCTCCACAGG  600
601  GTGAGG                                              606
```

FIG. 9

(SEQ ID NO: 24)

Nucleotide Sequence of Human Bcl11a cDNA (CCDS1862.1)

| | | |
|---|---|---|
| 1 | ATGTCTCGCCGCAAGCAAGGCAAACCCCAGCACTTAAGCAAACGGGAATT | 50 |
| 51 | CTCGCCCGAGCCTCTTGAAGCCATTCTTACAGATGATGAACCAGACCACG | 100 |
| 101 | GCCCGTTGGGAGCTCCAGAAGGGGATCATGACCTCCTCACCTGTGGGCAG | 150 |
| 151 | TGCCAGATGAACTTCCCATTGGGGGACATTCTTATTTTTATCGAGCACAA | 200 |
| 201 | ACGGAAACAATGCAATGGCAGCCTCTGCTTAGAAAAAGCTGTGGATAAGC | 250 |
| 251 | CACCTTCCCCTTCACCAATCGAGATGAAAAAGCATCCAATCCCGTGGAG | 300 |
| 301 | GTTGGCATCCAGGTCACGCCAGAGGATGACGATTGTTTATCAACGTCATC | 350 |
| 351 | TAGAGGAATTTGCCCCAAACAGGAACACATAGCAGATAAACTTCTGCACT | 400 |
| 401 | GGAGGGGCCTCTCCTCCCCTCGTTCTGCACATGGAGCTCTAATCCCCACG | 450 |
| 451 | CCTGGGATGAGTGCAGAATATGCCCCGCAGGGTATTTGTAAAGATGAGCC | 500 |
| 501 | CAGCAGCTACACATGTACAACTTGCAAACAGCCATTCACCAGTGCATGGT | 550 |
| 551 | TTCTCTTGCAACACGCACAGAACACTCATGGATTAAGAATCTACTTAGAA | 600 |
| 601 | AGCGAACACGGAAGTCCCCTGACCCCGCGGGTTGGTATCCCTTCAGGACT | 650 |
| 651 | AGGTGCAGAATGTCCTTCCCAGCCACCTCTCCATGGGATTCATATTGCAG | 700 |
| 701 | ACAATAACCCCTTTAACCTGCTAAGAATACCAGGATCAGTATCGAGAGAG | 750 |
| 751 | GCTTCCGGCCTGGCAGAAGGGCGCTTTCCACCCACTCCCCCCCTGTTTAG | 800 |
| 801 | TCCACCACCGAGACATCACTTGGACCCCCACCGCATAGAGCGCCTGGGGG | 850 |
| 851 | CGGAAGAGATGGCCCTGGCCACCCATCACCCGAGTGCCTTTGACAGGGTG | 900 |
| 901 | CTGCGGTTGAATCCAATGGCTATGGAGCCTCCCGCCATGGATTTCTCTAG | 950 |
| 951 | GAGACTTAGAGAGCTGGCAGGGAACACGTCTAGCCCACCGCTGTCCCCAG | 1000 |
| 1001 | GCCGGCCCAGCCCTATGCAAAGGTTACTGCAACCATTCCAGCCAGGTAGC | 1050 |
| 1051 | AAGCCGCCCTTCCTGGCGACGCCCCCCTCCCTCCTCTGCAATCCGCCCC | 1100 |
| 1101 | TCCTCCCTCCCAGCCCCGGTCAAGTCCAAGTCATGCGAGTTCTGCGGCA | 1150 |
| 1151 | AGACGTTCAAATTTCAGAGCAACCTGGTGGTGCACCGGCGCAGCCACACG | 1200 |
| 1201 | GGCGAGAAGCCCTACAAGTGCAACCTGTGCGACCACGCGTGCACCCAGGC | 1250 |
| 1251 | CAGCAAGCTGAAGCGCCACATGAAGACGCACATGCACAAATCGTCCCCCA | 1300 |
| 1301 | TGACGGTCAAGTCCGACGACGGTCTCTCCACCGCCAGCTCCCCGGAACCC | 1350 |

FIG. 10

```
1351  GGCACCAGCGACTTGGTGGGCAGCGCCAGCAGCGCGCTCAAGTCCGTGGT  1400
1401  GGCCAAGTTCAAGAGCGAGAACGACCCCAACCTGATCCCGGAGAACGGGG  1450
1451  ACGAGGAGGAAGAGGAGGACGACGAGGAAGAGGAAGAAGAGGAGGAAGAG  1500
1501  GAGGAGGAGGAGCTGACGGAGAGCGAGAGGGTGGACTACGGCTTCGGGCT  1550
1551  GAGCCTGGAGGCGGCGCGCCACCACGAGAACAGCTCGCGGGGCGCGGTCG  1600
1601  TGGGCGTGGGCGACGAGAGCCGCGCCCTGCCCGACGTCATGCAGGGCATG  1650
1651  GTGCTCAGCTCCATGCAGCACTTCAGCGAGGCCTTCCACCAGGTCCTGGG  1700
1701  CGAGAAGCATAAGCGCGGCCACCTGGCCGAGGCCGAGGGCCACAGGGACA  1750
1751  CTTGCGACGAAGACTCGGTGGCCGGCGAGTCGGACCGCATAGACGATGGC  1800
1801  ACTGTTAATGGCCGCGGCTGCTCCCCGGGCGAGTCGGCCTCGGGGGGCCT  1850
1851  GTCCAAAAAGCTGCTGCTGGGCAGCCCCAGCTCGCTGAGCCCCTTCTCTA  1900
1901  AGCGCATCAAGCTCGAGAAGGAGTTCGACCTGCCCCCGGCCGCGATGCCC  1950
1951  AACACGGAGAACGTGTACTCGCAGTGGCTCGCCGGCTACGCGGCCTCCAG  2000
2001  GCAGCTCAAAGATCCCTTCCTTAGCTTCGGAGACTCCAGACAATCGCCTT  2050
2051  TTGCCTCCTCGTCGGAGCACTCCTCGGAGAACGGGAGTTTGCGCTTCTCC  2100
2101  ACACCGCCCGGGGAGCTGGACGGAGGGATCTCGGGGCGCAGCGGCACGGG  2150
2151  AAGTGGAGGGAGCACGCCCCATATTAGTGGTCCGGGCCCGGGCAGGCCCA  2200
2201  GCTCAAAAGAGGGCAGACGCAGCGACACTTGTGAGTACTGTGGGAAAGTC  2250
2251  TTCAAGAACTGTAGCAATCTCACTGTCCACAGGAGAAGCCACACGGGCGA  2300
2301  AAGGCCTTATAAATGCGAGCTGTGCAACTATGCCTGTGCCCAGAGTAGCA  2350
2351  AGCTCACCAGGCACATGAAAACGCATGGCCAGGTGGGGAAGGACGTTTAC  2400
2401  AAATGTGAAATTTGTAAGATGCCTTTTAGCGTGTACAGTACCCTGGAGAA  2450
2451  ACACATGAAAAAATGGCACAGTGATCGAGTGTTGAATAATGATATAAAAA  2500
2501  CTGAATAG                                            2508
```

FIG. 10 (Cont.)

(SEQ ID NO: 28)

Nucleotide Sequence of I-HjeMI, Codon
Optimized for Expression in E.coli

| | | |
|---|---|---|
| 1 | ATGGGATCCCACATGGACCTGACCTACGCTTACCTGGTTGGTCTGTTCGA | 50 |
| 51 | AGGTGACGGTTACTTCTCTATCACCAAAAAGGGTAAATACCTGACCTACG | 100 |
| 101 | AACTGGGTATCGAACTGTCTATCAAAGACGTTCAGCTGATCTACAAAATC | 150 |
| 151 | AAAGACATCCTGGGTGTTGGTAAAGTTTCTTTCCGTAAACGTAACGAAAT | 200 |
| 201 | CGAAATGGTTTCTCTGCGTATCCGTGACAAGAATCACCTGAAAAACTTCA | 250 |
| 251 | TCCTGCCGATCTTCGACAAATACCCGATGCTGTCTAACAAGCAGTACGAC | 300 |
| 301 | TACCTGCGTTTCAAAGACGCTCTCCTGTCTAACATTATCTACTCTGACGA | 350 |
| 351 | TCTGCCGGAATACGCTCGTTCTAACGAATCTATCAACTCTGTTGACTCTA | 400 |
| 401 | TTATCAACACCTCTTACTTCTCTGCTTGGCTGGTTGGTTTCATCGAAGCT | 450 |
| 451 | GAAGGTTGCTTCTCTACCTACAAACTGAACAAAGATGACGATTACCTGAT | 500 |
| 501 | CGCTTCTTTCGACATCGCTCAGAAAGACGGTGACATCCTGATCTCTGCTA | 550 |
| 551 | TCCACAAATACCTGTCTTTCACCACGAAAATCTACCTGGACAAAACCAAC | 600 |
| 601 | TGCTCTCGTCTGAAAGTGACCGGTGTACGTTCTGTTAAAAACGTGGTTAA | 650 |
| 651 | ATTCATCCAGGGTGCTCCGGTTAAACTGCTCGGTAACAAGAAACTGCAGT | 700 |
| 701 | ACAAACTGTGGATCAAACAGCTGCGTAAAATCTCTCGTTACTCTGAAAAA | 750 |
| 751 | ATCCAGCTGCCGTCTAACTAC | 771 |

FIG. 14

(SEQ ID NO: 29)

Nucleotide Sequence of I-HjeMI, Codon Optimized for Expression in Mammals

| | | |
|---|---|---|
| 1 | ATGGGCAGCCACATGGACCTGACCTACGCCTATCTGGTCGGCCTGTTCGA | 50 |
| 51 | GGGCGACGGCTATTTTAGCATAACCAAGAAGGGCAAGTATCTGACGTATG | 100 |
| 101 | AACTGGGCATCGAGCTCTCCATCAAGGACGTGCAGCTCATCTACAAGATC | 150 |
| 151 | AAGGACATCCTCGGCGTGGGCAAAGTGTCTTTTAGGAAGAGGAACGAGAT | 200 |
| 201 | CGAGATGGTCAGCCTGCGAATCAGGGACAAAAACCACCTGAAGAACTTCA | 250 |
| 251 | TCCTGCCCATCTTCGACAAGTACCCCATGCTGAGCAACAAGCAGTACGAC | 300 |
| 301 | TATCTCCGATTCAAGGATGCCCTCCTGTCCAACATCATCTATAGCGACGA | 350 |
| 351 | CCTGCCCGAGTACGCCAGGAGCAACGAGTCAATCAATAGCGTGGACAGCA | 400 |
| 401 | TCATCAACACCTCATACTTCAGCGCCTGGCTGGTTGGCTTCATCGAGGCC | 450 |
| 451 | GAGGGCTGCTTCAGCACCTACAAGCTCAACAAGGACGACGATTATTTGAT | 500 |
| 501 | CGCGAGCTTCGATATAGCCCAGAAGGACGGCGACATTCTCATCTCCGCGA | 550 |
| 551 | TCCACAAATACCTGAGCTTCACGACCAAAATCTACCTGGACAAGACCAAC | 600 |
| 601 | TGTAGCAGGCTCAAGGTCACCGGCGTGAGGAGCGTCAAGAACGTGGTTAA | 650 |
| 651 | GTTCATCCAGGGTGCGCCGGTCAAGTTGCTGGGTAACAAGAAGCTGCAGT | 700 |
| 701 | ACAAACTTTGGATAAAGCAGCTGCGCAAGATCTCCCGATACAGCGAGAAA | 750 |
| 751 | ATCCAGCTGCCCAGTAACTAC | 771 |

FIG. 15

(SEQ ID NO: 30)

Amino Acid Sequence of the Homing Endonuclease I-HjeMI

| | | |
|---|---|---|
| 1 | MGDLTYAYLVGLFEGDGYFSITKKGKYLTYELGIELSIKDVQLIYKIKDI | 50 |
| 51 | LGVGKVSFRKRNEIEMVSLRIRDKNHLKNFILPIFDKYPMLSNKQYDYLR | 100 |
| 101 | FKDALLSNIIYSDDLPEYARSNESINSVDSIINTSYFSAWLVGFIEAEGC | 150 |
| 151 | FSTYKLNKDDDYLIASFDIAQKDGDILISAIHKYLSFTTKIYLDKTNCSR | 200 |
| 201 | LKVTGVRSVKNVVKFIQGAPVKLLGNKKLQYKLWIKQLRKISRYSEKIQL | 250 |
| 251 | PSNY | 254 |

FIG. 16

(SEQ ID NO: 31)

Nucleotide Sequence for a BCL11A Gene Targeting Nuclease
Based on the Homing Endonuclease I-HjeMI
(Codon Optimized for Expression in E.coli and Obtained
through Directed Evolution in IVC and in Bacteria)

| | | |
|---|---|---|
| 1 | ATGGGATCCCACATGGACCTGACCTACGCTTACCTGGTTGGTCTGTTCGA | 50 |
| 51 | AGGTGACGGTTACTTCACTATCGCTAAAGCGGGTAAGTACCTGAATTACG | 100 |
| 101 | AGCTGGGTATCACGCTGTCTATCAAAGACGCTCAGCTGATCTACAAAATC | 150 |
| 151 | AAAGACATCCTGGGTGTTGGTAATGTTTATTTCCGGAAATATAGGCAGCA | 200 |
| 201 | TGAAATGGTTTCTCTGCGGATCCAGGACAAGAATCACCTGAAAAACTTCA | 250 |
| 251 | TCCTGCCGATCTTCGACAAATACCCGATGCTGTCTAACAAGCAGTACGAC | 300 |
| 301 | TACCTGCGTTTCAAAGACGCTCTCCTGTCTAACATTATCTACTCTGACGA | 350 |
| 351 | TCTGCCGGAATACGCTCGTTCTAACGAATCTATCAACTCTGTTGACTCTA | 400 |
| 401 | TTATCAACACCTCTTACTTCTCTGCTTGGCTGGTTGGTTTCATCGAAGCT | 450 |
| 451 | GAAGGTTGCTTCACGACCTACAAAGCGAGTAAAGATAAGTACCTGACGGC | 500 |
| 501 | TGGGTTCAGTATCGCTCAGAAAGACGGTGACATCCTGATCTCTGCTATCC | 550 |
| 551 | ACAAATACCTGTCTTTCACCACGAAACCGTACAAGGACAAAACCAACTGC | 600 |
| 601 | TCTCATCTGAAGGTGACCGGTGTACGTTCTGTTAACAACGTGGTTAAATT | 650 |
| 651 | CATCCAGGGTGCTCCGGTTAAACTGCTCGGTAACAAGAAACTGCAGTACA | 700 |
| 701 | AACTGTGGATCAAACAGCTGCGTAAAATCTCTCGTTACTCTGAAAAAATC | 750 |
| 751 | CAGCTGCCGTCTAACTAC | 768 |

FIG. 17

(SEQ ID NO: 32)

Nucleotide Sequence of a BCL11A Gene Targeting Nuclease
Based on the Homing Endonuclease I-HjeMI (Codon Optimized for Expression in Mammals and Obtained
through Directed Evolution in IVC and in Bacteria)

```
  1 ATGGGCAGCCACATGGACCTGACCTACGCCTATCTGGTCGGCCTGTTCGA   50
 51 GGGCGACGGCTATTTTAcaATAgCtAAGgccGGCAAGTATCTGAacTACG  100
101 AGCTGGGCATCacaCTCTCCATCAAGGACGctCAGCTCATCTACAAGATC  150
151 AAGGACATCCTCGGCGTGGGCAAcGTGtaCTTTAGGAAGtacAggcAaca  200
201 tGAGATGGTCAGCCTGCGAATCcaGGACAAAAACCACCTGAAGAACTTCA  250
251 TCCTGCCCATCTTCGACAAGTACCCCATGCTGAGCAACAAGCAGTACGAC  300
301 TACCTGCGATTCAAGGATGCCCTCCTGTCCAACATCATCTATAGCGACGA  350
351 CCTGCCCGAGTACGCCAGGAGCAACGAGTCAATCAATAGCGTGGACAGCA  400
401 TCATCAACACCTCATACTTCAGCGCCTGGCTGGTTGGCTTCATCGAGGCC  450
451 GAGGGCTGCTTCAcCACCTACAAGgcatcCAAGGACaAgTACCTGAcaGC  500
501 GgGCTTCtccATAGCCCAGAAGGACGGCGACATTCTCATCTCCGCGATCC  550
551 ACAAATACCTGAGCTTCACGACCAAAccCTACaaaGACAAGACCAACTGT  600
601 AGCcacCTCAAGGTCACCGGCGTGAGGAGCGTCAAtAACGTGGTTAAGTT  650
651 CATCCAGGGTGCGCCGGTCAAGCTGCTGGGTAACAAGAAGCTGCAGTACA  700
701 AACTTTGGATAAAGCAGCTGCGCAAGATCTCCCGATACAGCGAGAAAATC  750
751 CAGCTGCCCAGTAACTAC                                  768
```

FIG. 18

(SEQ ID NO: 33)

Amino Acid Sequence of a BCL11A Gene Targeting
Nuclease Based on the Homing Endonuclease I-HjeMI

| | | |
|---|---|---|
| 1 | MGSHMDLTYAYLVGLFEGDGYFTIAKAGKYLNYELGITLSIKDAQLIYKI | 50 |
| 51 | KDILGVGNVYFRKYRQHEMVSLRIQDKNHLKNFILPIFDKYPMLSNKQYD | 100 |
| 101 | YLRFKDALLSNIIYSDDLPEYARSNESINSVDSIINTSYFSAWLVGFIEA | 150 |
| 151 | EGCFTTYKASKDKYLTAGFSIAQKDGDILISAIHKYLSFTTKPYKDKTNC | 200 |
| 201 | SHLKVTGVRSVNNVVKFIQGAPVKLLGNKKLQYKLWIKQLRKISRYSEKI | 250 |
| 251 | QLPSNY | 256 |

FIG. 19

Distribution of Amino-acid Residues Different between the BCL11A Gene-targeting Endonuclease and its Parental LHE I-Hj (SEQ ID NO: 34)
Nucleotide Sequence of I-OnuI, Codon Optimized for Expression in *E. coli*
(parental enzyme for HEs targeting the HbF silencing)

```
  1  ATGTCCGCCTACATGTCCCGTCGCGAGTCCATTAACCCGTGGATTCTCAC   50
 51  CGGTTTCGCCGACGCGGAAGGCTCCTTTTTGCTGCGCATCCGCAACAACA  100
101  ACAAGTCCAGCGTCGGCTACTCCACTGAGCTCGGCTTCCAAATTACACTT  150
151  CATAACAAGGACAAGAGCATTCTTGAGAACATCCAGTCAACATGGAAGGT  200
201  GGGCGTGATCGCCAACAGCGGTGACAACGCCGTGTCGCTGAAGGTCACGC  250
251  GTTTTGAGGACCTGAAGGTCATTATCGACCATTTTGAAAAATACCCACTG  300
301  ATTACGCAGAAGCTCGGTGACTACATGCTGTTTAAGCAGGCGTTTTGCGT  350
351  CATGGAGAACAAGGAGCATTTGAAGATTAATGGTATCAAGGAGCTGGTGC  400
401  GCATTAAGGCAAAGCTCAATTGGGGTCTGACGGATGAGCTGAAGAAGGCC  450
451  TTTCCGGAGATCATCTCGAAGGAGCGCTCCCTCATCAACAAGAACATCCC  500
501  TAATTTCAAGTGGCTGGCGGGTTTTACCTCGGGCGAGGGTTGCTTCTTTG  550
551  TTAACCTGATCAAGTCAAAGTCGAAGCTAGGTGTCCAGGTGCAGCTGGTG  600
601  TTCAGCATTACCCAACACATCAAGGATAAGAACCTCATGAACTCTCTGAT  650
651  TACCTACTTGGGCTGCGGCTACATTAAGGAGAAAAACAAGAGTGAGTTCT  700
701  CCTGGCTTGACTTCGTCGTCACGAAATTCTCCGACATCAACGACAAGATC  750
751  ATTCCGGTCTTTCAGGAAAACACGCTCATCGGCGTGAAGCTCGAGGACTT  800
801  CGAGGATTGGTGTAAGGTCGCTAAGCTGATCGAGGAGAAAAAGCACCTGA  850
851  CAGAAAGTGGCCTGGACGAGATCAAGAAGATTAAGCTGAACATGAACAAG  900
901  GGCAGAGTATTC                                        912
```

FIG. 22A

(SEQ ID NO: 15)

Amino Acid Sequence of I-OnuI homing endonuclease.

```
SAYMSRRESI NPWILTGFAD AEGSFLLRIR NNNKSSVGYS TELGFQITLH NKDKSILENI   60
QSTWKVGVIA NSGDNAVSLK VTRFEDLKVI IDHFEKYPLI TQKLGDYMLF KQAFCVMENK  120
EHLKINGIKE LVRIKAKLNW GLTDELKKAF PEIISKERSL INKNIPNFKW LAGFTSGEGC  180
FFVNLIKSKS KLGVQVQLVF SITQHIKDKN LMNSLITYLG CGYIKEKNKS EFSWLDFVVT  240
KFSDINDKII PVFQENTLIG VKLEDFEDWC KVAKLIEEKK HLTESGLDEI KKIKLNMNKG  300
RVF                                                               303
```

FIG. 22B

(SEQ ID NO: 35)

Nucleotide Sequence of MegaTAL:5.5 RVD + Y2 I-AniI

| 1 | gtggatctacgcacgctcggctacagtcagcagcagcaagagaagatcaa | 50 |
| 51 | accgaaggtgcgttcgacagtggcgcagcaccacgaggcactggtgggcc | 100 |
| 101 | atgggtttacacacgcgcacatcgttgcgctcagccaacacccggcagcg | 150 |
| 151 | ttagggaccgtcgctgtcacgtatcagcacataatcacggcgttgccaga | 200 |
| 201 | ggcgacacacgaagacatcgttggcgtcggcaaacagtggtccggcgcac | 250 |
| 251 | gcgccctggaggccttgctcacggatgcggggagttgagaggtccgccg | 300 |
| 301 | ttacagttggacacaggccaacttgtgaagattgcaaaacgtggcggcgt | 350 |
| 351 | gaccgcaatggaggcagtgcatgcatcgcgcaatgcactgacgggtgccc | 400 |
| 401 | ccctgaacctgaccccggaccaagtggtggctatcgccagcaacaatggc | 450 |
| 451 | ggcaagcaagcgctcgaaacggtgcagcggctgttgccggtgctgtgcca | 500 |
| 501 | ggaccatggcctgactccggaccaagtggtggctatcgccagccacgatg | 550 |
| 551 | gcggcaagcaagcgctcgaaacggtgcagcggctgttgccggtgctgtgc | 600 |
| 601 | caggaccatggcctgaccccggaccaagtggtggctatcgccagcaacat | 650 |
| 651 | tggcggcaagcaagcgctcgaaacggtgcagcggctgttgccggtgctgt | 700 |
| 701 | gccaggaccatggcctgaccccggaccaagtggtggctatcgccagcaac | 750 |
| 751 | aatggcggcaagcaagcgctcgaaacggtgcagcggctgttgccggtgct | 800 |
| 801 | gtgccaggaccatggcctgactccggaccaagtggtggctatcgccagcc | 850 |
| 851 | acgatggcggcaagcaagcgctcgaaacggtgcagcggctgttgccggtg | 900 |

FIG. 24

```
 901  ctgtgccaggaccatggcctgaccccggaccaagtggtggctatcgccag  950
 951  caacggtggcggcaagcaagcgctcgaaagcattgtggcccagctgagcc 1000
1001  ggcctgatccggcgttggccgcgttgaccaacgaccacctcgtcgccttg 1050
1051  gcctgcctcggcggacgtcctgccatggatgcagtgaaaaagggattgcc 1100
1101  gcacgcgccggaattgatcagaagagtcaatcgccgtattggcgaacgca 1150
1151  cgtcccatcgcgttgcgatatctagagtgggaggaagcgatcttacgtac 1200
1201  gcgtatttagttggtctctacgaaggggatggatactttagtatcaccaa 1250
1251  gaaaggcaagtacttgacttatgaattaggtattgagctgagcatcaaag 1300
1301  acgtccaattgatttacaagatcaagaaaatcctaggtattggcatcgta 1350
1351  agcttcaggaagagaaacgagattgaaatggttgcattgaggatccgtga 1400
1401  taagaatcatctaaaatctaagatattgcctatatttgagaagtatccaa 1450
1451  tgttttccaacaaacagtacgactatttaagattcaggaatgcattgtta 1500
1501  tctggcattatatacctagaagacttgcctgattacactagaagtgacga 1550
1551  accattgaattctatagaatccattatcaacacatcatacttctccgcct 1600
1601  ggctagttggatttatagaagctgagggctgtttcagtgtgtacaagctg 1650
1651  aacaaagacgatgactacttgattgcttcattcgacattgcccaaagaga 1700
1701  tggtgatatcttgatttcagcaattaggaagtacttaagtttcactacta 1750
1751  aggtttacctagacaagactaattgtagcaaattgaaggtcactagtgtt 1800
1801  agatccgtcgagaacatcattaagtttctgcagaatgctcctgtcaaatt 1850
1851  gttaggcaacaagaaactgcaatacaagttgtggttgaaacaactaagga 1900
1901  agatttctaggtattccgagaagatcaagattccatcaaactacgtcgac 1950
1951  cgagcatcttaccgccatttatacccatatttgttctgttttcttga    1998
```

FIG. 24 (Cont.)

(SEQ ID NO: 36)

Amino Acid Sequence of MegaTAL:5.5 RVD + Y2 I-AniI

```
  1  VDLRTLGYSQQQQEKIKPKVRSTVAQHHEALVGHGFTHAHIVALSQHPAA   50
 51  LGTVAVTYQHIITALPEATHEDIVGVGKQWSGARALEALLTDAGELRGPP  100
101  LQLDTGQLVKIAKRGGVTAMEAVHASRNALTGAPLNLTPDQVVAIASNNG  150
151  GKQALETVQRLLPVLCQDHGLTPDQVVAIASHDGGKQALETVQRLLPVLC  200
201  QDHGLTPDQVVAIASNIGGKQALETVQRLLPVLCQDHGLTPDQVVAIASN  250
251  NGGKQALETVQRLLPVLCQDHGLTPDQVVAIASHDGGKQALETVQRLLPV  300
301  LCQDHGLTPDQVVAIASNGGGKQALESIVAQLSRPDPALAALTNDHLVAL  350
351  ACLGGRPAMDAVKKGLPHAPELIRRVNRRIGERTSHRVAISRVGGSDLTY  400
401  AYLVGLYEGDGYFSITKKGKYLTYELGIELSIKDVQLIYKIKKILGIGIV  450
451  SFRKRNEIEMVALRIRDKNHLKSKILPIFEKYPMFSNKQYDYLRFRNALL  500
501  SGIIYLEDLPDYTRSDEPLNSIESIINTSYFSAWLVGFIEAEGCFSVYKL  550
551  NKDDDYLIASFDIAQRDGDILISAIRKYLSFTTKVYLDKTNCSKLKVTSV  600
601  RSVENIIKFLQNAPVKLLGNKKLQYKLWLKQLRKISRYSEKIKIPSNYVD  650
651  RASYRHLYPYLFCFS                                    665
```

FIG. 25

(SEQ ID NO: 37)

Nucleotide Sequence of Cas9 Endonuclease (from Mali *et al.*, *Science* (2013))

| | | |
|---:|:---|---:|
| 1 | gccaccATGGACAAGAAGTACTCCATTGGGCTCGATATCGGCACAAACAG | 50 |
| 51 | CGTCGGCTGGGCCGTCATTACGGACGAGTACAAGGTGCCGAGCAAAAAAT | 100 |
| 101 | TCAAAGTTCTGGGCAATACCGATCGCCACAGCATAAAGAAGAACCTCATT | 150 |
| 151 | GGCGCCCTCCTGTTCGACTCCGGGGAGACGGCCGAAGCCACGCGGCTCAA | 200 |
| 201 | AAGAACAGCACGGCGCAGATATACCCGCAGAAAGAATCGGATCTGCTACC | 250 |
| 251 | TGCAGGAGATCTTTAGTAATGAGATGGCTAAGGTGGATGACTCTTTCTTC | 300 |
| 301 | CATAGGCTGGAGGAGTCCTTTTTGGTGGAGGAGGATAAAAAGCACGAGCG | 350 |
| 351 | CCACCCAATCTTTGGCAATATCGTGGACGAGGTGGCGTACCATGAAAAGT | 400 |
| 401 | ACCCAACCATATATCATCTGAGGAAGAAGCTTGTAGACAGTACTGATAAG | 450 |
| 451 | GCTGACTTGCGGTTGATCTATCTCGCGCTGGCGCATATGATCAAATTTCG | 500 |
| 501 | GGGACACTTCCTCATCGAGGGGGACCTGAACCCAGACAACAGCGATGTCG | 550 |
| 551 | ACAAACTCTTTATCCAACTGGTTCAGACTTACAATCAGCTTTTCGAAGAG | 600 |
| 601 | AACCCGATCAACGCATCCGGAGTTGACGCCAAAGCAATCCTGAGCGCTAG | 650 |
| 651 | GCTGTCCAAATCCCGGCGGCTCGAAAACCTCATCGCACAGCTCCCTGGGG | 700 |
| 701 | AGAAGAAGAACGGCCTGTTTGGTAATCTTATCGCCCTGTCACTCGGGCTG | 750 |
| 751 | ACCCCCAACTTTAAATCTAACTTCGACCTGGCCGAAGATGCCAAGCTTCA | 800 |
| 801 | ACTGAGCAAAGACACCTACGATGATGATCTCGACAATCTGCTGGCCCAGA | 850 |
| 851 | TCGGCGACCAGTACGCAGACCTTTTTTTGGCGGCAAAGAACCTGTCAGAC | 900 |
| 901 | GCCATTCTGCTGAGTGATATTCTGCGAGTGAACACGGAGATCACCAAAGC | 950 |
| 951 | TCCGCTGAGCGCTAGTATGATCAAGCGCTATGATGAGCACCACCAAGACT | 1000 |
| 1001 | TGACTTTGCTGAAGGCCCTTGTCAGACAGCAACTGCCTGAGAAGTACAAG | 1050 |
| 1051 | GAAATTTTCTTCGATCAGTCTAAAAATGGCTACGCCGGATACATTGACGG | 1100 |
| 1101 | CGGAGCAAGCCAGGAGGAATTTTACAAATTTATTAAGCCCATCTTGGAAA | 1150 |
| 1151 | AAATGGACGGCACCGAGGAGCTGCTGGTAAAGCTTAACAGAGAAGATCTG | 1200 |
| 1201 | TTGCGCAAACAGCGCACTTTCGACAATGGAAGCATCCCCCACCAGATTCA | 1250 |
| 1251 | CCTGGGCGAACTGCACGCTATCCTCAGGCGGCAAGAGGATTTCTACCCCT | 1300 |

FIG. 26

| | | |
|---|---|---|
| 1301 | TTTTGAAAGATAACAGGGAAAAGATTGAGAAAATCCTCACATTTCGGATA | 1350 |
| 1351 | CCCTACTATGTAGGCCCCCTCGCCCGGGGAAATTCCAGATTCGCGTGGAT | 1400 |
| 1401 | GACTCGCAAATCAGAAGAGACCATCACTCCCTGGAACTTCGAGGAAGTCG | 1450 |
| 1451 | TGGATAAGGGGGCCTCTGCCCAGTCCTTCATCGAAAGGATGACTAACTTT | 1500 |
| 1501 | GATAAAAATCTGCCTAACGAAAAGGTGCTTCCTAAACACTCTCTGCTGTA | 1550 |
| 1551 | CGAGTACTTCACAGTTTATAACGAGCTCACCAAGGTCAAATACGTCACAG | 1600 |
| 1601 | AAGGGATGAGAAAGCCAGCATTCCTGTCTGGAGAGCAGAAGAAAGCTATC | 1650 |
| 1651 | GTGGACCTCCTCTTCAAGACGAACCGGAAAGTTACCGTGAAACAGCTCAA | 1700 |
| 1701 | AGAAGACTATTTCAAAAAGATTGAATGTTTCGACTCTGTTGAAATCAGCG | 1750 |
| 1751 | GAGTGGAGGATCGCTTCAACGCATCCCTGGGAACGTATCACGATCTCCTG | 1800 |
| 1801 | AAAATCATTAAAGACAAGGACTTCCTGGACAATGAGGAGAACGAGGACAT | 1850 |
| 1851 | TCTTGAGGACATTGTCCTCACCCTTACGTTGTTTGAAGATAGGGAGATGA | 1900 |
| 1901 | TTGAAGAACGCTTGAAAACTTACGCTCATCTCTTCGACGACAAAGTCATG | 1950 |
| 1951 | AAACAGCTCAAGAGGCGCCGATATACAGGATGGGGGCGGCTGTCAAGAAA | 2000 |
| 2001 | ACTGATCAATGGGATCCGAGACAAGCAGAGTGGAAAGACAATCCTGGATT | 2050 |
| 2051 | TTCTTAAGTCCGATGGATTTGCCAACCGGAACTTCATGCAGTTGATCCAT | 2100 |
| 2101 | GATGACTCTCTCACCTTTAAGGAGGACATCCAGAAAGCACAAGTTTCTGG | 2150 |
| 2151 | CCAGGGGGACAGTCTTCACGAGCACATCGCTAATCTTGCAGGTAGCCCAG | 2200 |
| 2201 | CTATCAAAAGGGAATACTGCAGACCGTTAAGGTCGTGGATGAACTCGTC | 2250 |
| 2251 | AAAGTAATGGGAAGGCATAAGCCCGAGAATATCGTTATCGAGATGGCCCG | 2300 |
| 2301 | AGAGAACCAAACTACCCAGAAGGGACAGAAGAACAGTAGGGAAAGGATGA | 2350 |
| 2351 | AGAGGATTGAAGAGGGTATAAAAGAACTGGGGTCCCAAATCCTTAAGGAA | 2400 |
| 2401 | CACCCAGTTGAAAACACCCAGCTTCAGAATGAGAAGCTCTACCTGTACTA | 2450 |
| 2451 | CCTGCAGAACGGCAGGGACATGTACGTGGATCAGGAACTGGACATCAATC | 2500 |
| 2501 | GGCTCTCCGACTACGACGTGGATCATATCGTGCCCCAGTCTTTTCTCAAA | 2550 |
| 2551 | GATGATTCTATTGATAATAAAGTGTTGACAAGATCCGATAAAAATAGAGG | 2600 |
| 2601 | GAAGAGTGATAACGTCCCCTCAGAAGAAGTTGTCAAGAAAATGAAAAATT | 2650 |
| 2651 | ATTGGCGGCAGCTGCTGAACGCCAAACTGATCACACAACGGAAGTTCGAT | 2700 |
| 2701 | AATCTGACTAAGGCTGAACGAGGTGGCCTGTCTGAGTTGGATAAAGCCGG | 2750 |
| 2751 | CTTCATCAAAAGGCAGCTTGTTGAGACACGCCAGATCACCAAGCACGTGG | 2800 |
| 2801 | CCCAAATTCTCGATTCACGCATGAACACCAAGTACGATGAAAATGACAAA | 2850 |
| 2851 | CTGATTCGAGAGGTGAAAGTTATTACTCTGAAGTCTAAGCTGGTCTCAGA | 2900 |

FIG. 26 (Cont.)

| | | |
|---|---|---|
| 2901 | TTTCAGAAAGGACTTTCAGTTTTATAAGGTGAGAGAGATCAACAATTACC | 2950 |
| 2951 | ACCATGCGCATGATGCCTACCTGAATGCAGTGGTAGGCACTGCACTTATC | 3000 |
| 3001 | AAAAAATATCCCAAGCTTGAATCTGAATTTGTTTACGGAGACTATAAAGT | 3050 |
| 3051 | GTACGATGTTAGGAAAATGATCGCAAAGTCTGAGCAGGAAATAGGCAAGG | 3100 |
| 3101 | CCACCGCTAAGTACTTCTTTTACAGCAATATTATGAATTTTTTCAAGACC | 3150 |
| 3151 | GAGATTACACTGGCCAATGGAGAGATTCGGAAGCGACCACTTATCGAAAC | 3200 |
| 3201 | AAACGGAGAAACAGGAGAAATCGTGTGGGACAAGGGTAGGGATTTCGCGA | 3250 |
| 3251 | CAGTCCGGAAGGTCCTGTCCATGCCGCAGGTGAACATCGTTAAAAAGACC | 3300 |
| 3301 | GAAGTACAGACCGGAGGCTTCTCCAAGGAAAGTATCCTCCCGAAAAGGAA | 3350 |
| 3351 | CAGCGACAAGCTGATCGCACGCAAAAAAGATTGGGACCCCAAGAAATACG | 3400 |
| 3401 | GCGGATTCGATTCTCCTACAGTCGCTTACAGTGTACTGGTTGTGGCCAAA | 3450 |
| 3451 | GTGGAGAAAGGGAAGTCTAAAAAACTCAAAAGCGTCAAGGAACTGCTGGG | 3500 |
| 3501 | CATCACAATCATGGAGCGATCAAGCTTCGAAAAAAACCCCATCGACTTTC | 3550 |
| 3551 | TCGAGGCGAAAGGATATAAAGAGGTCAAAAAAGACCTCATCATTAAGCTT | 3600 |
| 3601 | CCCAAGTACTCTCTCTTTGAGCTTGAAAACGGCCGGAAACGAATGCTCGC | 3650 |
| 3651 | TAGTGCGGGCGAGCTGCAGAAAGGTAACGAGCTGGCACTGCCCTCTAAAT | 3700 |
| 3701 | ACGTTAATTTCTTGTATCTGGCCAGCCACTATGAAAAGCTCAAAGGGTCT | 3750 |
| 3751 | CCCGAAGATAATGAGCAGAAGCAGCTGTTCGTGGAACAACACAAACACTA | 3800 |
| 3801 | CCTTGATGAGATCATCGAGCAAATAAGCGAATTCTCCAAAAGAGTGATCC | 3850 |
| 3851 | TCGCCGACGCTAACCTCGATAAGGTGCTTTCTGCTTACAATAAGCACAGG | 3900 |
| 3901 | GATAAGCCCATCAGGGAGCAGGCAGAAAACATTATCCACTTGTTTACTCT | 3950 |
| 3951 | GACCAACTTGGGCGCGCCTGCAGCCTTCAAGTACTTCGACACCACCATAG | 4000 |
| 4001 | ACAGAAAGCGGTACACCTCTACAAAGGAGGTCCTGGACGCCACACTGATT | 4050 |
| 4051 | CATCAGTCAATTACGGGGCTCTATGAAACAAGAATCGACCTCTCTCAGCT | 4100 |
| 4101 | CGGTGGAGACAGCAGGGCTGACCCCAAGAAGAAGAGGAAGGTGTGA | 4046 |

FIG. 26 (Cont.)

(SEQ ID NO: 38)

Nucleotide Sequence of RNA Guide Strand for use with Cas9 Endonuclease
(from Mali *et al., Science* (2013))

```
  1 TGTACAAAAAAGCAGGCTTTAAAGGAACCAATTCAGTCGACTGGATCCGG  50
 51 TACCAAGGTCGGGCAGGAAGAGGGCCTATTTCCCATGATTCCTTCATATT 100
101 TGCATATACGATACAAGGCTGTTAGAGAGATAATTAGAATTAATTTGACT 150
151 GTAAACACAAAGATATTAGTACAAAATACGTGACGTAGAAAGTAATAATT 200
201 TCTTGGGTAGTTTGCAGTTTTAAAATTATGTTTTAAAATGGACTATCATA 250
251 TGCTTACCGTAACTTGAAAGTATTTCGATTTCTTGGCTTTATATATCTTG 300
301 TGGAAAGGACGAAACACCGNNNNNNNNNNNNNNNNNNNNGTTTTAGAGCTA 350
351 GAAATAGCAAGTTAAAATAAGGCTAGTCCGTTATCAACTTGAAAAAGTGG 400
401 CACCGAGTCGGTGCTTTTTTTCTAGACCCAGCTTTCTTGTACAAAGTTGG 450
451 CATTA                                              455
```

FIG. 27

(SEQ ID NO: 62)

Nucleotide Sequence of a I-CpaMI homing endonuclease (ORF, codon optimized for mammalian expression)

```
ATGAACACCA GCTCTAGCTT CAATCCCTGG TTCCTGACCG GCTTTAGCGA TGCAGAGTGC  60
TCTTTCAGCA TCCTGATACA GGCCAACAGC AAGTACTCCA CCGGTTGGAG GATCAAGCCC 120
GTGTTCGCCA TCGGCTTGCA CAAGAAGGAC CTGGAGCTTC TGAAGAGAAT CCAGAGCTAT 180
CTGGGCGTGG GCAAGATACA CATTCACGGC AAAGACAGCA TTCAGTTCAG GATTGACAGC 240
CCCAAGGAGC TGGAGGTGAT CATCAACCAC TTTGAGAACT ACCCCCTGGT AACCGCCAAG 300
TGGGCCGACT ACACCCTCTT TAAGAAGGCC CTGGACGTAA TTCTGTTGAA GGAGCACCTG 360
AGCCAGAAGG GCCTGCTTAA ACTGGTAGGC ATTAAGGCGA GCCTGAATCT CGGGTTGAAC 420
GGCAGCCTCA AGGAGGCGTT CCCGAACTGG GAAGAACTGC AGATCGACAG GCCGAGCTAC 480
GTGTTCAAGG GCATCCCCGA CCCCAACTGG ATCAGCGGCT TCGCGTCAGG CGATAGCAGC 540
TTTAATGTGA AAATCAGCAA CTCCCCCACG TCACTGCTCA ATAAAAGGGT GCAGCTGAGG 600
TTCGGCATCG GACTGAACAT CAGAGAGAAA GCCCTTATCC AATACCTGGT GGCCTACTTT 660
GACCTGTCAG ACAACCTGAA GAACATCTAC TTCGACCTGA ACAGCGCACG GTTCGAGGTG 720
GTGAAGTTCA GCGACATCAC CGACAAGATC ATCCCCTTCT TCGACAAGTA CAGCATACAA 780
GGCAAGAAGA GCCTGGACTA CATCAACTTC AAGGAAGTGG CCGACATTAT CAAGAGCAAG 840
AACCATCTTA CTAGCGAGGG CTTCCAGGAA ATCTTGGACA TCAAAGCCAG TATGAACAAG 900
```

FIG. 28

(SEQ ID NO: 63)

Amino Acid Sequence of I-CpaMI homing endonuclease

```
MNTSSSFNPW FLTGFSDAEC SFSILIQANS KYSTGWRIKP VFAIGLHKKD LELLKRIQSY  60
LGVGKIHIHG KDSIQFRIDS PKELEVIINH FENYPLVTAK WADYTLFKKA LDVILLKEHL 120
SQKGLLKLVG IKASLNLGLN GSLKEAFPNW EELQIDRPSY VFKGIPDPNW ISGFASGDSS 180
FNVKISNSPT SLLNKRVQLR FGIGLNIREK ALIQYLVAYF DLSDNLKNIY FDLNSARFEV 240
VKFSDITDKI IPFFDKYSIQ GKKSLDYINF KEVADIIKSK NHLTSEGFQE ILDIKASMNK 300
```

FIG. 29

(SEQ ID NO: 64)
Nucleotide sequence of BCL11A gene targeting nuclease-encoding plasmid
(pExodusBCL11Ahje)

```
GACGGATCGGGAGATCTCCCGATCCCCTATGGTGCACTCTCAGTACAATCTGCTCTGATGCCGCATAGTTAAGCCAGTAT
CTGCTCCCTGCTTGTGTGTTGGAGGTCGCTGAGTAGTGCGCGAGCAAAATTTAAGCTACAACAAGGCAAGGCTTGACCGA
CAATTGCATGAAGAATCTGCTTAGGGTTAGGCGTTTTGCGCTGCTTCGCGATGTACGGGCCAGATATACGCGTTGACATT
GATTATTGACTAGTTATTAATAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGCCCACTTGGCAGTACATCAAGTGT
ATCATATGCCAAGTACGCCCCCTATTGACGTCAATGACGGTAAATGGCCCGCCTGGCATTATGCCCAGTACATGACCTTA
TGGGACTTTCCTACTTGGCAGTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAATGGGAGTTTGTTTTGGCACC
AAAATCAACGGGACTTTCCAAAATGTCGTAACAACTCCGCCCCATTGACGCAAATGGGCGGTAGGCGTGTACGGTGGGAG
GTCTATATAAGCAGAGCTCTCTGGCTAACTAGAGAACCCACTGCTTACTGGCTTATCGAAATTAATACGACTCACTATAG
GGAGACCCAAGCTGGCTAGCGTTTAAACTTAAGCTTGGTACCGAGCTCGGATCCACTAGTCCAGTGTGGTGGAATTCTGC
AGGTACGTTGACGCCGCCACCATGGGATATCCATACGATGTCCCAGATTATGCGCCACCTAAGAAGAAACGCAAAGTCCC
CGGGGGCAGCCACATGGACCTGACCTACGCCTATCTGGTCGGCCTGTTCGAGGGCGACGGCTATTTTTAcaATAgCtAAGg
ccGGCAAGTATCTGAAcTACGAGCTGGGCATCacaCTCTCCATCAAGGACGctCAGCTCATCTACAAGATCAAGGACATC
CTCGGCGTGGGCAAcGTGtaCTTTAGGAAGtacAggcAacatGAGATGGTCAGCCTGCGAATCcaGGACAAAAACCACCT
GAAGAACTTCATCCTGCCCATCTTCGACAAGTACCCCATGCTGAGCAACAAGCAGTACGACTACCTGCGATTCAAGGATG
CCCTCCTGTCCAACATCATCTATAGCGACGACCTGCCCGAGTACGCCAGGAGCAACGAGTCAATCAATAGCGTGGACAGC
ATCATCAACACCTCATACTTCAGCGCCTGGCTGGTTGGCTTCATCGAGGCCGAGGGCTGCTTCAcCACCTACAAGgcatc
CAAGGACAaGtACCTGAcaGCGgGCTTCtccATAGCCCAGAAGGACGGCGACATTCTCATCTCCGCGATCCACAAATACC
TGAGCTTCACGACCAAAccCTACAaaGACAAGACCAACTGTAGCcacCTCAAGGTCACCGGCGTGAGGAGCGTCAAtAAC
GTGGTTAAGTTCATCCAGGGGTGCGCCGGTCAAGCTGCTGGGTAACAAGAAGCTGCAGTACAAACTTTGGATAAAGCAGCT
GCGCAAGATCTCCCGATACAGCGAGAAAATCCAGCTGCCCAGTAACTACTAATCTAGAGGGCCCGTTTAAACCCGCTGAT
CAGCCTCGACTGTGCCTTCTAGTTGCCAGCCATCTGTTGTTTGCCCCTCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGATGCGGTGGGCTCTATGGCTTCTG
AGGCGGAAAGAACCAGCTGGGGCTCTAGGGGGTATCCCCACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCCGATTTAGTGCTTTACGGCACCTCGACC
CCAAAAAACTTGATTAGGGTGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGTCTATTCTTTTGATTTATA
AGGGATTTTGCCGATTTCGGCCTATTGGTTAAAAAATGAGCTGATTTAACAAAAATTTAACGCGAATTAATTCTGTGGAA
TGTGTGTCAGTTAGGGTGTGGAAAGTCCCCAGGCTCCCCAGCAGGCAGAAGTATGCAAAGCCTATCAGGACATAGCGTTG
GCTACCCGTGATATTGCTGAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGGTTCGAAATGACCGACCAAGC
GACGCCCAACCTGCCATCACGAGATTTCGATTCCACCGCCGCCTTCTATGAAAGGTTGGGCTTCGGAATCGTTTTCCGGG
ACGCCGGCTGGATGATCCTCCAGCGCGGGGATCTCATGCTGGAGTTCTTCGCCCACCCCAACTTGTTTATTGCAGCTTAT
AATGGTTACAAATAAAGCAATAGCATCACAAATTTCACAAATAAAGCATTTTTTTCACTGCATTCTAGTTGTGGTTTGTC
```

FIG. 32

```
CAAACTCATCAATGTATCTTATCATGTCTGTATACCGTCGACCTCTAGCTAGAGCTTGGCGTAATCATGGTCATAGCTGT
TTCCTGTGTGAAATTGTTATCCGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGGAAACCTGTCGTGCCAGCTGCA
TTAATGAATCGGCCAACGCGCGGGGAGAGGCGGTTTGCGTATTGGGCGCTCTTCCGCTTCCTCGCTCACTGACTCGCTGC
GCTCGGTCGTTCGGCTGCGGCGAGCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCCGCGTTGCTGGCGTTTTTCCATAG
GCTCCGCCCCCTGACGAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTAACTATCGTCTTGAGTCCAACCCGGTAAGAC
ACGACTTATCGCCACTGGCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAGCCAGTTACCTTCGGAAA
AAGAGTTGGTAGCTCTTGATCCGGCAAACAAACCACCGCTGGTAGCGGTTTTTTTGTTTGCAAGCAGCAGATTACGCGCA
GAAAAAAAGGATCTCAAGAAGATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGAAGTTTTAAATCAATCTAAAG
TATATATGAGTAAACTTGGTCTGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACCATCTGGCCCCAGTGCTGCAATG
ATACCGCGAGACCCACGCTCACCGGCTCCAGATTTATCAGCAATAAACCAGCCAGCCGGAAGGGCCGAGCGCAGAAGTGG
TCCTGCAACTTTATCCGCCTCCATCCAGTCTATTAATTGTTGCCGGGAAGCTAGAGTAAGTAGTTCGCCAGTTAATAGTT
TGCGCAACGTTGTTGCCATTGCTACAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCGAGTTGCTCTTGCCCGGCG
TCAATACGGGATAATACCGCGCCACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATAAGGGCGACACGGAAATGTTGA
ATACTCATACTCTTCCTTTTTCAATATTATTGAAGCATTTATCAGGGTTATTGTCTCATGAGCGGATACATATTTGAATG
TATTTAGAAAAATAAACAAATAGGGGTTCCGCGCACATTTCCCCGAAAAGTGCCACCTGACGTC
```

FIG. 32 (Cont.)

(SEQ ID NO: 65)

Nucleotide sequence of TREX2-encoding plasmid (pExodus CMV.Trex2)

gacggatcgggagatctcccgatcccctatggtgcactctcagtacaatctgctctgatgccgcatagtt
aagccagtatctgctccctgcttgtgtgttggaggtcgctgagtagtgcgcgagcaaaatttaagctaca
acaaggcaaggcttgaccgacaattgcatgaagaatctgcttagggttaggcgttttgcgctgcttcgcg
atgtacgggccagatatacgcgttgacattgattattgactagttattaatagtaatcaattacggggtc
attagttcatagcccatatatggagttccgcgttacataacttacggtaaatggcccgcctggctgaccg
cccaacgaccccgcccattgacgtcaataatgacgtatgttcccatagtaacgccaatagggactttcc
attgacgtcaatgggtggagtatttacggtaaactgcccacttggcagtacatcaagtgtatcatatgcc
aagtacgccccctattgacgtcaatgacggtaaatggcccgcctggcattatgcccagtacatgaccta
tgggactttcctacttggcagtacatctacgtattagtcatcgctattaccatggtgatgcggttttggc
agtacatcaatgggcgtggatagcggtttgactcacggggatttccaagtctccaccccattgacgtcaa
tgggagtttgttttggcaccaaaatcaacgggactttccaaaatgtcgtaacaactccgccccattgacg
caaatgggcggtaggcgtgtacggtgggaggtctatataagcagagctctctggctaactagagaaccca
ctgcttactggcttatcgaaattaatacgactcactatagggagacccaagctggctagcatgtctgagc
cacctcgggctgagacctttgtattcctggacctagaagccactgggctcccaaacatggaccctgagat
tgcagagatatcccttttgctgttcaccgctcttccctggagaacccagaacgggatgattctggttcc
ttggtgctgccccgtgttctggacaagctcacactgtgcatgtgcccggagcgccccttactgccaagg
ccagtgagattactggtttgagcagcgaaagcctgatgcactgcgggaaggctggtttcaatggcgctgt
ggtaaggacactgcagggcttcctaagccgccaggagggcccatctgccttgtggcccacaatggcttc
gattatgacttcccactgctgtgcacggagctacaacgtctgggtgcccatctgccccaagacactgtct
gcctggacacactgcctgcattgcggggcctggaccgtgctcacagccacggcaccagggctcaaggccg
caaaagctacagcctggccagtctcttccaccgctacttccaggctgaacccagtgctgcccattcagca
gaaggtgatgtgcacaccctgcttctgatcttcctgcatcgtgctcctgagctgctcgcctgggcagatg

FIG. 33 agcaggcccgcagctgggctcatattgagcccatgtacgtgccacctgatggtccaagcctcgaagcctg
aattctgcagatatccagcacagtggcggccgctcgagtctagagggcccgtttaaacccgctgatcagc
ctcgactgtgccttctagttgccagccatctgttgtttgcccctcccccgtgccttccttgaccctggaa
ggtgccactcccactgtcctttcctaataaaatgaggaaattgcatcgcattgtctgagtaggtgtcatt
ctattctgggggtggggtggggcaggacagcaaggggaggattgggaagacaatagcaggcatgctgg
ggatgcggtgggctctatggcttctgaggcggaaagaaccagctggggctctaggggtatccccacgcg
ccctgtagcggcgcattaagcgcggcgggtgtggtggttacgcgcagcgtgaccgctacacttgccagcg
ccctagcgcccgctcctttcgctttcttcccttcctttctcgccacgttcgccggctttccccgtcaagc
tctaaatcggggctccctttagggttccgatttagtgctttacggcacctcgaccccaaaaaacttgat
tagggtgatggttcacgtagtgggccatcgccctgatagacggttttcgccctttgacgttggagtcca
cgttctttaatagtggactcttgttccaaactggaacaacactcaaccctatctcggtctattcttttga
tttataagggattttgccgatttcggcctattggttaaaaaatgagctgatttaacaaaaatttaacgcg
aattaattctgtggaatgtgtgtcagttagggtgtggaaagtccccaggctccccagcaggcagaagtat
gcaaagcctatcaggacatagcgttggctacccgtgatattgctgaagagcttggcggcgaatgggctga
ccgcttcctcgtgctttacggtatcgccgctcccgattcgcagcgcatcgccttctatcgccttcttgac
gagttcttctgagcgggactctggggttcgaaatgaccgaccaagcgacgcccaacctgccatcacgaga
tttcgattccaccgccgccttctatgaaaggttgggcttcggaatcgttttccgggacgccggctggatg
atcctccagcgcggggatctcatgctggagttcttcgcccaccccaacttgtttattgcagcttataatg
gttacaaataaagcaatagcatcacaaatttcacaaataaagcatttttttcactgcattctagttgtgg
tttgtccaaactcatcaatgtatcttatcatgtctgtataccgtcgacctctagctagagcttggcgtaa
tcatggtcatagctgtttcctgtgtgaaattgttatccgctcacaattccacacaacatacgagccggaa
gcataaagtgtaaagcctggggtgcctaatgagtgagctaactcacattaattgcgttgcgctcactgcc
cgctttccagtcgggaaacctgtcgtgccagctgcattaatgaatcggccaacgcgcggggagaggcggt
ttgcgtattgggcgctcttccgcttcctcgctcactgactcgctgcgctcggtcgttcggctgcggcgag
cggtatcagctcactcaaaggcggtaatacggttatccacagaatcaggggataacgcaggaaagaacat
gtgagcaaaaggccagcaaaaggccaggaaccgtaaaaaggccgcgttgctggcgtttttccataggctc
cgcccccctgacgagcatcacaaaaatcgacgctcaagtcagaggtggcgaaacccgacaggactataaa

```
gataccaggcgtttccccctggaagctccctcgtgcgctctcctgttccgaccctgccgcttaccggata
cctgtccgcctttctcccttcgggaagcgtggcgctttctcatagctcacgctgtaggtatctcagttcg
gtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaa
caggattagcagagcgaggtatgtaggcggtgctacagagttcttgaagtggtggcctaactacggctac
actagaagaacagtatttggtatctgcgctctgctgaagccagttaccttcggaaaaagagttggtagct
cttgatccggcaaacaaaccaccgctggtagcggttttttgtttgcaagcagcagattacgcgcagaaa
aaaaggatctcaagaagatcctttgatcttttctacggggtctgacgctcagtggaacgaaaactcacgt
taagggattttggtcatgagattatcaaaaaggatcttcacctagatccttttaaattaaaaatgaagtt
ttaaatcaatctaaagtatatatgagtaaacttggtctgacagttaccaatgcttaatcagtgaggcacc
tatctcagcgatctgtctatttcgttcatccatagttgcctgactccccgtcgtgtagataactacgata
cgggagggcttaccatctggccccagtgctgcaatgataccgcgagacccacgctcaccggctccagatt
tatcagcaataaaccagccagccggaagggccgagcgcagaagtggtcctgcaactttatccgcctccat
ccagtctattaattgttgccgggaagctagagtaagtagttcgccagttaatagtttgcgcaacgttgtt
gccattgctacaggcatcgtggtgtcacgctcgtcgtttggtatggcttcattcagctccggttcccaac
gatcaaggcgagttacatgatcccccatgttgtgcaaaaaagcggttagctccttcggtcctccgatcgt
tgtcagaagtaagttggccgcagtgttatcactcatggttatggcagcactgcataattctcttactgtc
atgccatccgtaagatgcttttctgtgactggtgagtactcaaccaagtcattctgagaatagtgtatgc
ggcgaccgagttgctcttgcccggcgtcaatacgggataataccgcgccacatagcagaactttaaaagt
gctcatcattggaaaacgttcttcggggcgaaaactctcaaggatcttaccgctgttgagatccagttcg
atgtaacccactcgtgcacccaactgatcttcagcatcttttactttcaccagcgtttctgggtgagcaa
aaacaggaaggcaaaatgccgcaaaaaagggaataagggcgacacggaaatgttgaatactcatactctt
cctttttcaatattattgaagcatttatcagggttattgtctcatgagcggatacatatttgaatgtatt
tagaaaaataaacaaataggggttccgcgcacatttccccgaaaagtgccacctgacgtc
```

FIG. 33 (Cont.)

COMPOSITIONS AND METHODS FOR THE TREATMENT OF HEMOGLOBINOPATHIES

CROSS REFERENCE TO RELATED APPLICATIONS

This application is a divisional of U.S. Non-Provisional application Ser. No. 14/380,935 filed on Aug. 25, 2014, which is a 317 National Phase Application of PCT Patent Application No. PCT/US2013/027459 filed on Feb. 22, 2013, which claims priority to U.S. Provisional Patent Application No. 61/603,231, filed Feb. 24, 2012. The content of each of these patent applications is incorporated by reference in its entirety.

FEDERAL SUPPORT

This invention was made with government support under DK044746 awarded by the National Institutes of Health. The government has certain rights in the invention.

SEQUENCE LISTING

The Sequence Listing associated with this application is provided in text format in lieu of a paper copy, and is hereby incorporated by reference into the specification. The name of the text file containing the Sequence Listing is FHCR_030_02US_ST25.txt. The text file is 69 KB, was created on Mar. 16, 2017, and is being submitted electronically via EFS-Web, concurrent with the filing of the specification.

BACKGROUND OF THE DISCLOSURE

Technical Field of the Disclosure

The present disclosure relates, generally, to the treatment of genetic diseases. More specifically, the present disclosure provides endonuclease-based compositions and methods, including homing endonuclease- and Cas9 endonuclease-based compositions and methods, for altering the expression of globin genes, which compositions and methods are useful for the treatment of thalassemias, sickle cell disease, and other hemoglobinopathies.

Description of the Related Art

Hemoglobinopathies, such as thalassemias and sickle cell disease, are highly prevalent genetic red blood cell disorders that cause a significant health burden worldwide. Over 1,300,000 people with severe hemoglobin disorders are born each year. While 5% of people worldwide are carriers, the birth rates are 0.44 and 1.96 per thousand for clinically significant forms of thalassemia and sickle cell disease (SCD), respectively.

In the normal state, hemoglobins found in mammalian erythroid cells predominantly consist of heterotetramers of two α-like chains (polypeptides) and two β-like chains. The five genes of the β-globin locus reside in a cluster on chromosome 11. The genes are expressed in an erythroid, and developmentally stage specific manor; the ε, $A_\gamma$ and $G_\gamma$, and δ and β genes being expressed primarily during the embryonic, fetal and post-natal periods respectively. At birth 95% of β-like chains are γ, with the rest being β. This ratio gradually inverts during the first year of life, explaining why phenotypes limited to the β-globin gene such as sickle cell and most β-thalassemias do not manifest until several months of age. Expression of the chromosome 16 based α-like genes differs; the embryonic ζ-gene parallels the expression of ε, but the twin α-genes are expressed from the fetal period onward. Thus α abnormalities manifest in utero, potentially with devastating consequences (e.g. hydrops fetalis). The resultant α-, β-heterotetramers are developmentally expressed; embryonic: Hb Gower1 ($\zeta_2,\varepsilon_2$), Hb Gower2 ($\alpha_2,\varepsilon_2$) and Hb Portland ($\zeta_2,\gamma_2$); fetal: HbF (Fetal) ($\alpha_2,\gamma_2$) and Adult: HbA2 ($\alpha_2,\delta_2$) and HbA (Adult) ($\alpha_2,\beta_2$).

β-thalassemia is caused by an abnormality in the adult β-globin locus, which results in an abnormal stoichiometry of β-like globin chains to α-like chains, resulting in the precipitation of the unpaired α-like chains. The severity of thalassemia is directly related to the degree of this globin chain imbalance. The ensuing damage meditated through several pathways including oxidation of cellular and membrane proteins culminates in ineffective erythropoiesis, apoptosis, and decreased red cell survival. Over 200 mutations have been described that are responsible for β-thalassemia.

Sickle cell disease is caused by a single nucleotide substitution within the β-globin gene, which results in glutamic acid being substituted by valine at amino acid position 6 of the peptide resulting in $\beta^S$. Hemoglobin S ($\alpha_2,\beta^S_2$), which carries this mutation, is referred to as HbS, as opposed to the normal adult hemoglobin (HbA). Under conditions of low oxygen concentration HbS undergoes an allosteric change at which point it can polymerize. The deoxy-form of hemoglobin exposes a hydrophobic patch on the protein between the E and F helices. The hydrophobic valine at position 6 of the hemoglobin β-chain forms a hydrophobic patch which can associate with the hydrophobic patch of other hemoglobin S molecules causing hemoglobin S molecules to aggregate and form fibrous precipitates which, in turn, cause the red blood cells to adopt a sickle-shape and leads to alterations in numerous pathways that result in tissue damage via vaso-occlusion and hemolyis.

Although β-thalassemia and sickle cell disease (SCD) are quantitative and qualitative disorders, respectively, of the β-globin locus, the expression of normal β-like globin genes can ameliorate both diseases. In thalassemia, any improvement in the globin chain imbalance provides a selective advantage for each cell and results in clinical benefit. In sickle cell disease the presence of normal or certain mutant β-like chains can ameliorate the clinical phenotype by competing for α-like chains more effectively than the mutant sickle cell chains thus reducing the amount of HbS, by forming hemoglobins that block the polymerization of Hbs (e.g. HbF) and increasing the amount of non-sickling hemoglobin per cell. For example, in sickle cell disease, fetal hemoglobin (HbF) levels of only 8% inhibit polymerization of HbS, which results in increased survival, while HbF levels of 20% provide nearly complete phenotypic correction. Critically, the progeny of donor erythroid cells containing normal HbA have a strong selective advantage following hematopoietic stem cell transplantation (HSCT) over endogenous derived cells containing HbS. A patient with 11% donor cells in the marrow had 35% donor BFUe and 73% donor erythrocytes, which resulted in transfusion independence. Thus, correction in a relatively small fraction of transplanted HSCs provides clinical benefit.

Severe forms of thalassemia require chronic transfusions, resulting in iron overload. Survival directly correlates with the efficacy of chelation, though cost, side effects, and compliance severely limit efficacy. The only FDA approved drug for SCD is hydroxyurea, which can attenuate morbidity and mortality. This treatment, however, is under-prescribed, compliance is poor, and it does not adequately protect health.

Hematopoietic cell transplantation (HCT) is an important therapeutic option for thousands of patients each year with hematologic malignancies and related disorders. According to the Center for International Blood and Marrow Transplant Research (CIBMTR), approximately 60,000 transplants were performed in 2009, an increase of over 15,000 transplants per year compared to a decade earlier. The effectiveness of transplantation is also increasing, with more recent outcomes demonstrating a significant reduction in the risk of relapse, non-relapse mortality, and overall mortality. Gooley et al., *N. Engl. J. Med.* 363:2091-101 (2011).

Allogeneic hematopoietic cell transplantation (HCT) from HLA-matched sibling or unrelated donors offers a cure for patients with hemoglobinopathies, but is limited by the need for a suitably matched related or unrelated donor and is complicated by graft versus host disease (GVHD) and infections. In addition, a major barrier is a high rate of graft failures, which is higher than observed for HCT for malignancies. Alternative approaches include performing HCT with donor cord blood cells, as cord blood donors can be identified for nearly all patients. Additional experimental approaches are focused on using a patient's own hematopoietic stem cells (HSCs) and inducing expression of the endogenous globin genes, or adding an exogenous β-like globin gene.

For many patients who are unable to find a donor, particularly those of ethnic minority or mixed race background, umbilical cord blood (CB) transplantation may offer the best hope for cure. A source of donor stem cells (easily collected at the time of birth without risk to the mother or infant), CB also has the advantage of being readily available and safely used in an HLA-mismatched setting without increasing the risk of GVHD.

Unfortunately, several factors, including the low cell dose available in many cord blood units lead to slow engraftment and an increase in transplant related mortality in adults and larger children. Significantly delayed hematopoietic recovery of both neutrophils and platelets is a known risk factor for cord blood transplant (CBT) recipients and is associated with the low total nucleated cell (TNC) and $CD34^+$ cell doses provided in a single or double CB transplant. Similarly, these low cell numbers correlate with higher rates of graft failure, thus a particular concern in hemoglobinopathies where there is already high risk of graft failure. In fact, a recent analysis of adult single CBT recipients demonstrated that infused $CD34^+$ cell dose is the most important predictor of myeloid engraftment.

Non-relapse mortality (NRM) is highest in double CBT (dCBT) recipients when compared to matched and mismatched unrelated donor recipients. Brunstein et al., *Blood* 116:4693-9 (2010). The majority of the NRM occurs within the first 100 days post transplant with infection being the most common cause of death. Importantly, an analysis of the risk factors for NRM among dCBT recipients revealed a higher risk in patients with delayed myeloid recovery (time to absolute neutrophil count (ANC)>500/ml) if the recovery was ≥26 days, the median time to engraftment in dCBT recipients. When, however, the analysis of risk factors for NRM was restricted to include only those dCBT recipients engrafting before day 26, no difference was found between the donor sources, emphasizing the important contribution of delayed engraftment to increased risk of NRM.

Moreover, an ANC of >100 on any given day post stem cell transplant has been previously shown to be a critical threshold for a decreased risk of mortality before day 100 post transplant (Offner et al., *Blood* 88:4058-62 (1996)). Thus, the significant delay in myeloid recovery that is observed in CBT recipients remains a critical barrier to successful outcomes in the CBT setting. The ability to increase not only the absolute number of CB progenitor cells available for transplantation, but also cells that can reliably result in more rapid myeloid recovery post-transplant, should improve overall survival for patients undergoing CBT. Strategies utilizing ex vivo expansion of cord blood stem/progenitor cells are being developed to overcome the low cell dose available in a cord blood graft with the goal of enhancing hematopoietic recovery and overall survival in CBT.

With the goal of overcoming the significant delay in neutrophil recovery that occurs following transplantation with umbilical cord blood (CB), the role of the Notch signaling pathway in regulating ex vivo expansion of hematopoietic stem/progenitor cells has been investigated to generate increased numbers of progenitor cells capable of rapid repopulation in vivo. A clinically feasible methodology utilizing an engineered Notch ligand (Delta1) has been developed, which results in a multi-log increase in the absolute numbers of $CD34^+$ cells and a cellular therapy capable of rapid repopulation in vivo.

Infusion of expanded, partially HLA-matched cells results in a significant reduction in the median time to achieve an initial absolute neutrophil count (ANC) of 500/ml to just 11 days as compared to a median time of 25 days (p<0.0001) in a concurrent cohort of 29 patients undergoing identical treatment but with two non-manipulated CB units. Although the number of patients treated was small (i.e. n=14), a significant effect on time to myeloid recovery was demonstrated, as was the safety and clinical feasibility of this approach.

Despite tremendous investment of resources by many laboratories for over 30 years, there has been little progress in the development of therapeutic regimens for hemoglobinopathies, in large part due to the lack of identified drugable targets and the requirement for gene therapy vectors to persistently express at extremely high levels, while not leading to insertional mutagenesis. While increased expression of fetal hemoglobin (HbF) ameliorates both hemoglobinopathies, extensive research has not yielded viable new agents based on that observation. Hematopoietic stem cell (HSC) gene therapy with integrating lentiviral vectors is being pursued by several investigators. HSC gene therapy, however, requires high-level persistent expression and carries a substantial risk of insertional mutagenesis and leukemia.

What is critically needed in the art are compositions and methods, which exhibit improved efficacy for the treatment of hemoglobinopathies, including thalassemias and sickle cell disease while overcoming the safety concerns of existing therapeutic modalities.

SUMMARY OF THE DISCLOSURE

The present disclosure addresses these and other related needs in the art by providing, inter alia, compositions and methods for the treatment of hemoglobinopathies. Compositions and methods disclosed herein employ one or more polynucleotide that encodes one or more endonuclease(s) or endonuclease fusion protein(s), including one or more homing endonuclease(s) and/or homing endonuclease fusion protein(s) and/or one or more CRISPR endonucleases (i.e. Cas9 endonucleases in combination with one or more RNA guide strands) and/or CRISPR endonuclease fusion protein(s) (i.e. Cas9 endonuclease fusion protein(s) in combination with one or more RNA guide strands): (a) to disrupt a Bcl11a coding region or a Bcl11a gene regulatory region; (b) to disrupt a HbF silencing DNA regulatory element or pathway, such as a Bcl11a-regulated HbF silencing region; (c) to mutate one or more γ-globin gene promoter(s) to achieve increased expression of a γ-globin gene; (d) to mutate one or more δ-globin gene promoter(s) to achieve increased expression of a δ-globin gene; and/or (e) to correct one or more β-globin gene mutation(s).

Within a first embodiment, the present disclosure provides compositions and methods that comprise a polynucleotide that encodes one or more endonuclease(s), such as a homing endonuclease (HE) and/or a CRISPR endonucleases (i.e. Cas9 endonucleases in combination with one or more RNA guide strands) to achieve the targeted disruption of a sequence within a Bcl11a coding region or a Bcl11a gene regulatory region, thereby increasing to therapeutic levels the expression of an endogenous gene such as a γ- or a ε-globin gene. Within related aspects, the compositions of these embodiments comprise a polynucleotide that encodes one or more TALEN, one or more TALE-HE fusion protein, and/or one or more TREX2 protein.

Within a second embodiment, the present disclosure provides compositions and methods that comprise a polynucleotide that encodes one or more endonuclease(s), such as a homing endonuclease (HE) or a CRISPR endonucleases (i.e. Cas9 endonucleases in combination with one or more RNA guide strands) to achieve the targeted disruption of a key regulatory sequence within a β-globin gene locus, thereby increasing to therapeutic levels the expression of an endogenous gene such as a γ- or δ-globin gene. Within related aspects, the compositions of these embodiments comprise a polynucleotide that encodes one or more TALEN, one or more TALE-HE fusion protein, and/or one or more TREX2 protein.

Within certain aspects of this embodiment are provided HEs and CRISPR endonucleases that target a 3.6 kb region (SEQ ID NO: 1) within a β-globin gene locus (chr11: 5212342-5215944 in HG18) that contains a binding site for the regulatory protein Bcl11a.

The homing endonucleases and CRISPR endonucleases described herein exhibit unique advantages over conventional gene targeting nucleases. Because they are broadly efficacious regardless of genotype, the homing and Cas9 endonucleases in combination with one or more RNA guide strands described herein are not patient specific, they provide clinical benefit in the heterozygotic state, and avoid the insertion of vector sequences.

Within a third embodiment, the present disclosure provides compositions and methods for recapitulating, via genome editing, one or more naturally-occurring mutation(s) within a patient's genome thereby providing clinical benefits including, for example, deletional or non-deletional forms of hereditary persistence of fetal hemoglobin (HPFH). More specifically, the present disclosure provides compositions and methods for achieving the direct correction of a thalassemia and/or a sickle cell disease (SCD) mutation through genome editing.

Within certain aspects of this embodiment, one or more homing endonuclease(s) is/are employed in combination with a normal or wild-type polynucleotide sequence (correction template) to permit the editing and/or repair of one or more genetic sequence, such as a β-like globin gene(s). These homing endonucleases permit the modification of key regulatory and/or coding sequences within a gene locus, exemplified herein by the human β-globin gene locus, through the transient expression of a polynucleotide that includes one or more naturally occurring mutation(s). Within related aspects, the compositions of these embodiments comprise a polynucleotide that encodes one or more TALEN, one or more TALE-HE fusion protein, and/or one or more TREX2 protein.

More specifically, the present disclosure provides compositions and methods for genome editing, comprising one or more polynucleotides, each encoding a HE and a correction template, which may be employed to generate naturally-occurring mutations within stem cells, including, for example, hematopoietic stem cells (HSCs), embryonic stem (ES) cells, and induced pluripotent stem cells (iPSCs). Genome edited HSCs, ESs, and iPSCs, including autologous HSCs and iPSCs, may be transplanted into a patient to treat one or more hemoglobinopathies, such as a thalassemia and/or sickle cell disease.

The compositions and methods disclosed herein permit the efficient modification of HSCs, ESs, and iPSCs, through the transient expression of a polynucleotide encoding a HE with or without a targeting template, a Cas9 endonuclease, and/or an RNA guide strand, without the need for the persistent expression or insertion of an exogenous gene to achieve the amelioration of hemoglobinopathies in mature erythroid cells and in patient cells in vivo. Because these therapeutic methods do not require the integration and/or persistent expression of a transgene, the safety concerns associated with currently available gene therapy technologies are obviated.

Within a fourth embodiment, the present disclosure provides compositions and methods for the delivery of one or more homing endonuclease(s) and/or one or more Cas9 endonuclease(s) in combination with one or more RNA guide strands, each of which may be transiently expressed in targeted regions shown to have clinical benefit in humans. The endonuclease coding sequences described herein may be expressed in combination with, or fused to, a TAL effector nuclease (TALEN) coding sequence. Exemplified herein are TAL effector-HE (TALE-HE) fusion proteins and polynucleotides that encode those TALE-HE fusion proteins, which target critical genomic regions that influence fetal hemoglobin production.

Within certain aspects of these embodiments, a polynucleotide encoding one or more HE with or without a targeting template, one or more Cas9 endonuclease, one or more RNA guide strands, one or more TALEN, one or more TALE-HE fusion protein, and/or one or more TREX2 protein are operably linked to a promoter sequence within a viral vector to achieve the delivery and transient expression of a HE, a Cas9, an RNA guide strand, a TALEN, a TALE-HE fusion protein, and/or a TREX2 protein. Suitable viral vectors that may be satisfactorily employed for the delivery of HE, TALEN, TALE-HE fusion protein, and/or TREX2 protein may be selected from the group consisting of a cocal pseudotyped lentiviral vector, a foamy virus vector, an adenoviral vector, and an adeno-associated viral (AAV) vector.

Within a fifth embodiment, the present disclosure provides compositions and methods comprising ex-vivo expanded modified hematopoietic stem cells (HSCs), which allow for efficient engraftment of corrected cells and the use of induced pluripotent stem cells (iPSCs) for screening and clinical application. Within certain aspects of these embodiments are provided compositions and methods for the efficient expansion of autologous HSCs, autologous gene-modified HSCs, iPSC-derived HSCs, and ES cells. Cord blood expansion methodology may be employed, which methodology utilizes Delta1 in serum free media supplemented with hematopoietic growth factors using mobilized peripheral blood CD34+ cells obtained from normal donors. These compositions and methods may be used in combination with one or more additional reagent to enhance the survival and proliferation of hematopoietic stem/progenitor cells. Within other aspects, these compositions and methods may employ endothelial cell co-cultures for the enhanced expansion of long-term repopulating cells, including corrected iPSC-derived HSCs.

Within a sixth embodiment, the present disclosure provides compositions and methods for providing supportive care, which compositions and methods comprise off-the-shelf cellular therapies that abrogate post-transplant neutropenia and improve outcome following transplantation of gene-corrected autologous HSCs. Ex vivo expanded, cryopreserved cord blood (CB) stem/progenitor cells may, for example, be administered as a means of supportive care to patients with thalassemia and/or sickle cell disease who are undergoing myeloablative HCT with autologous CD34+ gene corrected cells.

BRIEF DESCRIPTION OF THE DRAWINGS

Certain aspects of the present disclosure will be better understood in view of the following figures:

FIG. 6 (SEQ ID NO: 1) is the sequence of the 3.6 kb region for which the HbF silencing region falls, which spans chr11:5212342-5215944 in HG18.

FIG. 7 (SEQ ID NO: 2) is the 350 base pair region spanning from a repeat element (chr11:5,213,912-5,214,261 in HG18), through the upstream French HPFH breakpoint known to disrupt the Bcl111a occupancy region within the HbF silencing region and that includes a GATA-1 binding motif, and from which exemplary homing endonucleases (HEs) of the present disclosure were designed.

FIG. 8 (SEQ ID NO: 13) is the human beta-globin gene from 1 kb upstream of the cap through the polyA site, which spans from chr11:5203272-5205877 in HG18 (reverse strand).

FIG. 9 (SEQ ID NO: 14) is a 606 bp region of the human beta-globin spanning from the promoter into Intron 2 (chr11: 5204380-5204985 in HG18). This relatively small region contains the majority of mutations leading to severe thalassemia as well as the mutation causing sickle cell disease. This small region is readily amenable to homologous recombination resulting in gene correction.

FIG. 10 (SEQ ID NO: 24) is the cDNA sequence for human Bcl11a cDNA (CCDS1862.1).

FIG. 14 (SEQ ID NO: 28) is the nucleotide sequence of I-HjeMI (the parental enzyme for the BCL11A gene targeting nuclease), which is codon optimized for expression in *E. coli*.

FIG. 15 (SEQ ID NO: 29) is the nucleotide sequence of I-HjeMI (the parental enzyme for the BCL11A gene targeting nuclease), which is codon optimized for mammalian expression.

FIG. 16 (SEQ ID NO: 30) is the amino acid sequence of the homing endonuclease I-HjeMI.

FIG. 17 (SEQ ID NO: 31) is the nucleotide sequence of a BCL11A gene targeting nuclease (Bcl11Ahje), which is based on the homing endonuclease I-HjeMI (obtained through directed evolution in IVC and in bacteria), which is codon optimized for expression in *E. coli*.

FIG. 18 (SEQ ID NO: 32) is the nucleotide sequence of a BCL11A gene targeting nuclease based on the homing endonuclease I-HjeMI (obtained through directed evolution in IVC and in bacteria), which is codon optimized for mammalian expression.

FIG. 19 (SEQ ID NO: 33) is the amino acid sequence of a BCL11A gene targeting nuclease based on the homing endonuclease I-HjeMI (obtained through directed evolution in IVC and in bacteria).

FIG. 22A (SEQ ID NO: 34) nucleotide sequence of I-OnuI homing endonuclease (the parental enzyme for homing endonucleases targeting the HbF silencing region), codon optimized for expression in *E. coli*.

FIG. 22B (SEQ ID NO: 15) is an amino acid sequence of I-OnuI homing endonuclease.

FIG. 24 (SEQ ID NO: 35) is the nucleotide sequence of MegaTAL:5.5 RVD+Y2 I-AniI.

FIG. 25 (SEQ ID NO: 36) is an amino acid sequence of MegaTAL:5.5 RVD+Y2 I-AniI.

FIG. 26 (SEQ ID NO: 37) nucleotide sequence of Cas9 endonuclease (from Mali et al., *Science* (2013)).

FIG. 27 (SEQ ID NO: 38) is the nucleotide sequence of an RNA Guide Strand for use with Cas9 endonuclease (from Mali et al., *Science* (2013)).

FIG. 28 (SEQ ID NO: 62) is a nucleotide sequence of I-CpaMI homing endonuclease (ORF, codon optimized for mammalian expression).

FIG. 29 (SEQ ID NO: 63) is an amino acid sequence of I-CpaMI homing endonuclease.

FIG. 32 (SEQ ID NO: 64) is a nucleotide sequence of a BCL11A gene targeting nuclease-encoding plasmid (pExodusBCL11Ahje).

FIG. 33 (SEQ ID NO: 65) is a nucleotide sequence of TREX2-encoding plasmid (pExodus CMV.Trex2).

DETAILED DESCRIPTION OF THE DISCLOSURE

Figure 1:
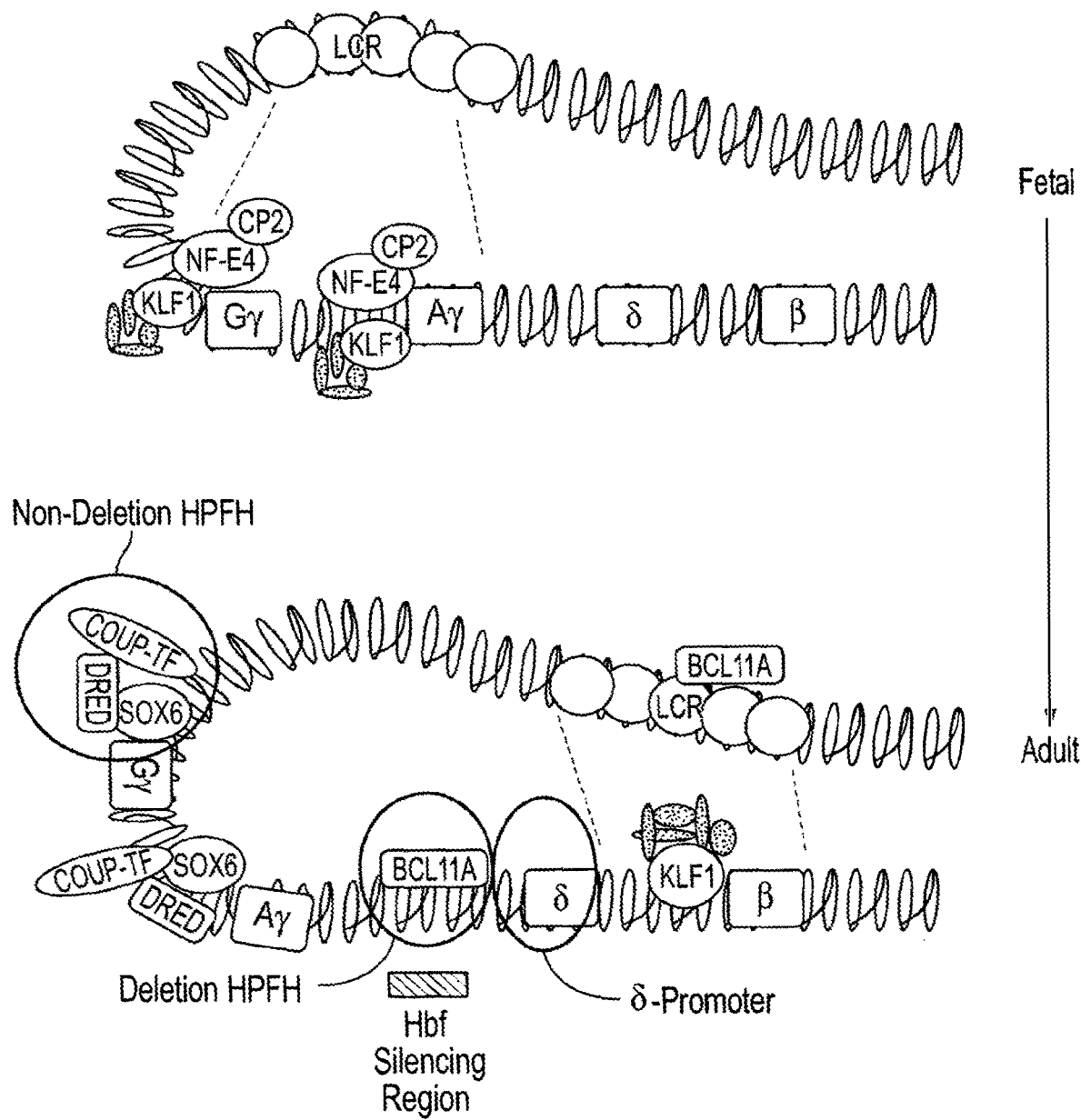
FIG. 1 shows targets to increase expression of β-globin-like genes in adult erythroid tissues. Factors that are implicated in regulating the switch from a fetal expression pattern (two γ genes) to an adult program (δ and β) are displayed. (Adapted from Wilber et al., *Blood* 117(15):3945-3953 (2011)).
Figure 2:
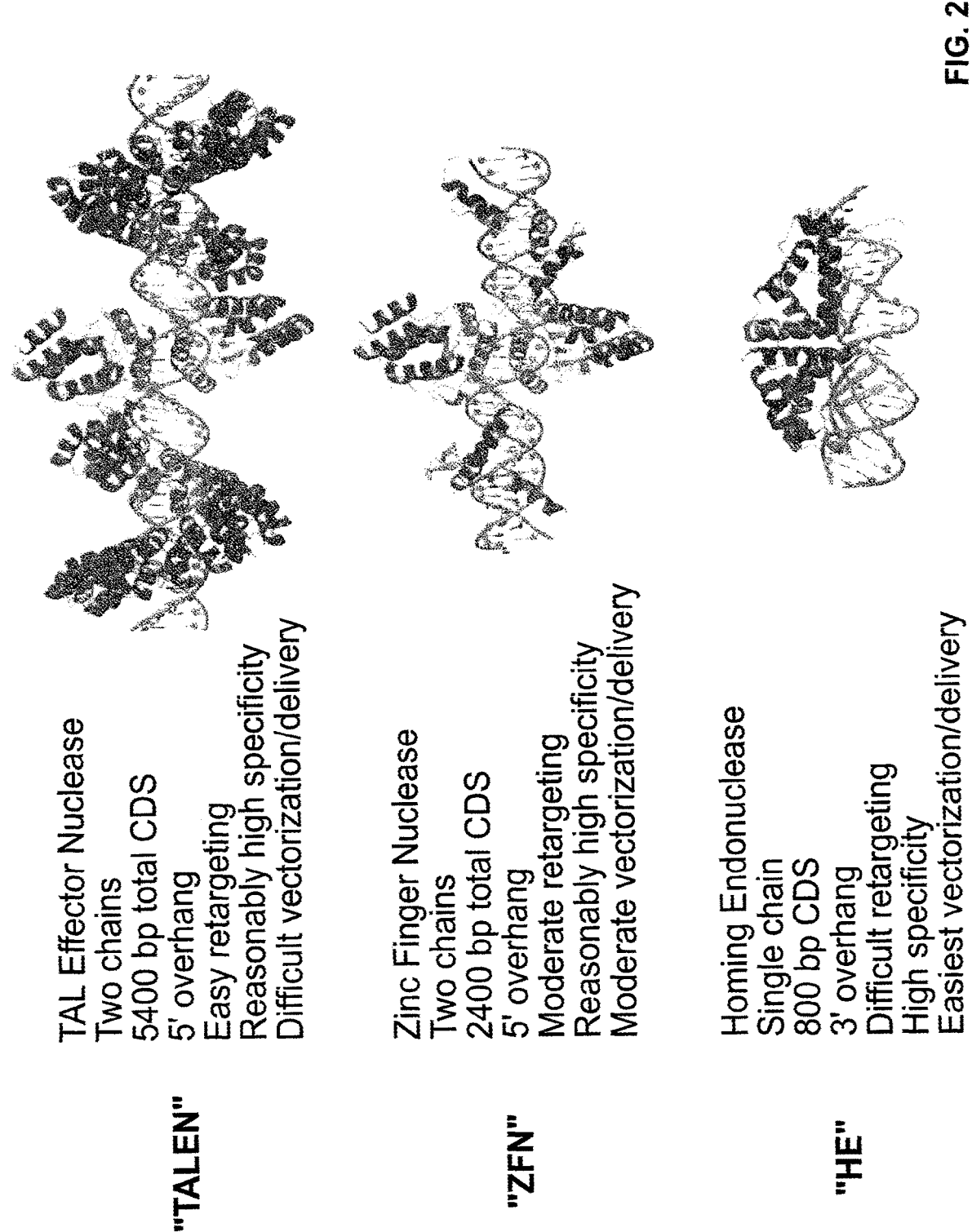
FIG. 2 depicts three exemplary rare cleaving nuclease technologies.
Figure 3:
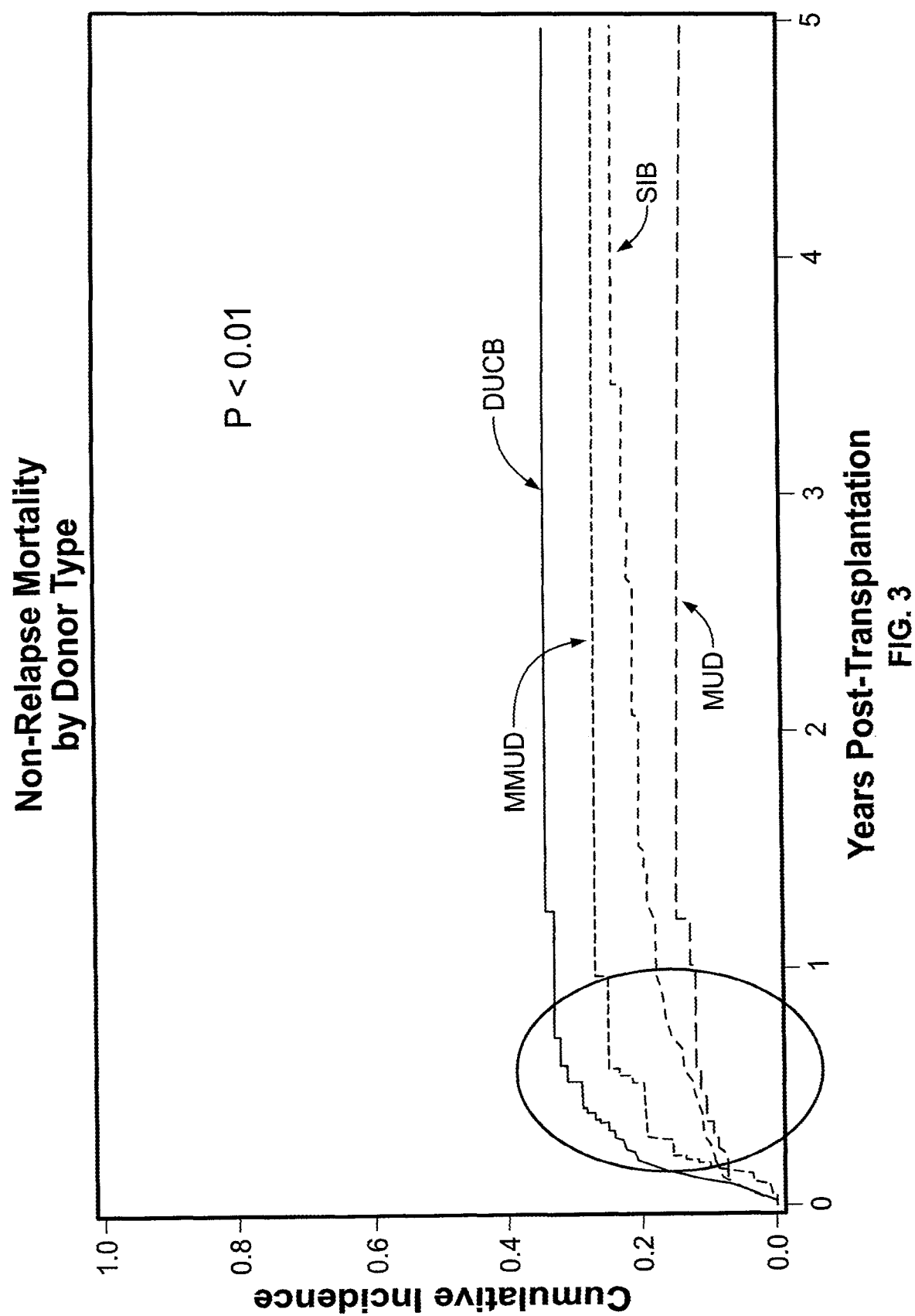
FIG. 3 is a graph showing that the risk of non-relapse mortality is highest among double CBT recipients. Non-relapse mortality after double CBT (DUCB), matched unrelated donor (MUD), mismatched unrelated donor (MMUD), and matched related donor (SIB) transplant.
Figure 4:
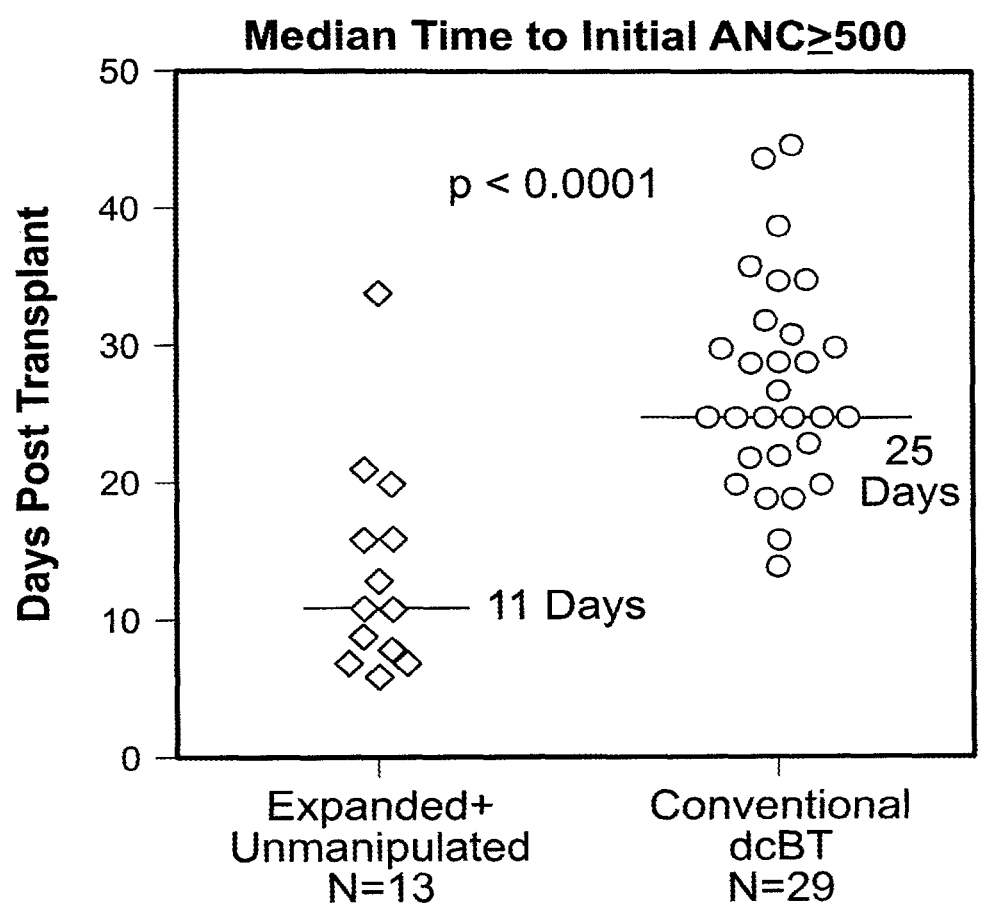
FIG. 4 shows that a culture of CB progenitors with Delta1$^{ext-IgG}$ results in more rapid neutrophil recovery in a myeloablative double CBT setting. The individual and median times (solid line) to ANC of ≥500/μl for patients receiving double unit CBT with two non-manipulated units ("conventional") versus with one ex vivo expanded unit and one non-manipulated unit ("expanded") is presented.
Figure 5:
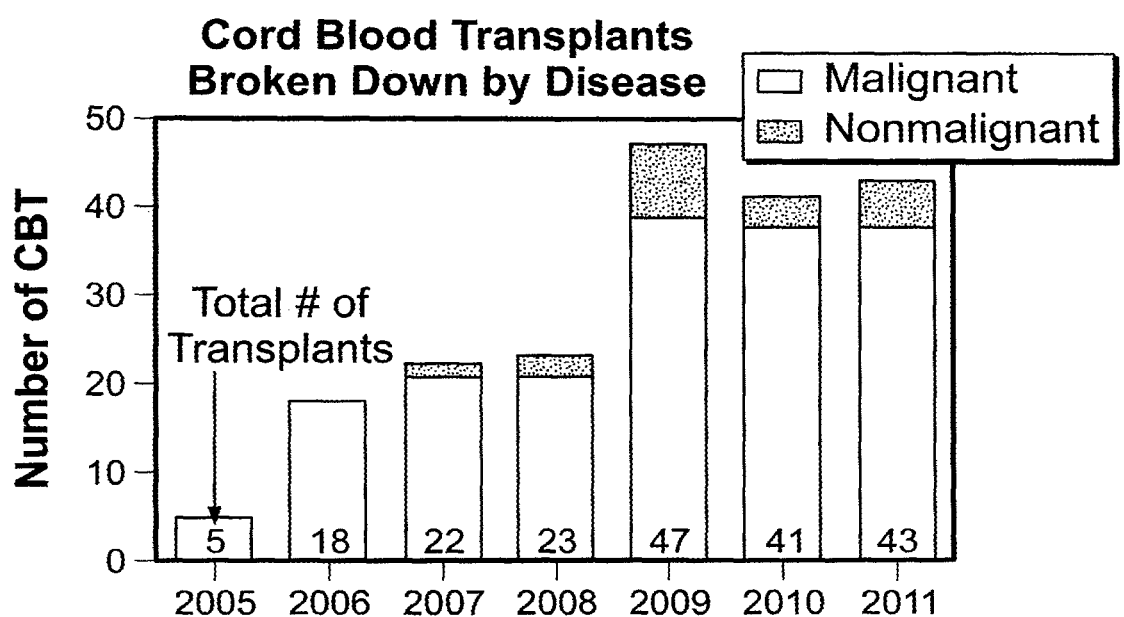
FIG. 5 is a bar graph depicting the number of cord blood transplantations performed annually by disease indication.

The present disclosure is directed, generally, to compositions and methods for the treatment of a genetic disease, such as a hemoglobinopathy, by the transient or persistent expression of a polynucleotide that encodes one or more endonuclease(s) or endonuclease fusion protein(s), including one or more homing endonuclease(s) and/or homing endonuclease fusion protein(s) and/or one or more Cas9 endonuclease(s) and/or Cas9 endonuclease fusion protein(s) in combination with one or more RNA guide strands: (a) to disrupt a Bcl11a coding region; (b) to disrupt a HbF silencing DNA regulatory element or pathway, such as a Bcl11a-regulated HbF silencing region; (c) to mutate one or more γ-globin gene promoter(s) to achieve increased expression of a γ-globin gene; (d) to mutate one or more δ-globin gene promoter(s) to achieve increased expression of a δ-globin gene; and/or (e) to correct one or more β-globin gene mutation(s). The compositions and methods disclosed herein find utility in the treatment of hemoglobinopathies, including β-thalassemia and sickle cell disease. The compositions and methods described herein may, optionally, comprise a polynucleotide that encodes one or more TALEN, one or more TALE-HE fusion protein, and/or one or more TREX2 protein.

The present disclosure will be better understood in view of the following definitions:

Definitions

As used herein, the term "hemoglobinopathy" refers to a class of genetic defects that result in an abnormal structure, abnormal function or altered expression of one or more of the globin chains of the hemoglobin molecule. Hemoglobinopathies are inherited single-gene disorders. Common hemoglobinopathies include thalassemias and sickle-cell disease.

As used herein, the term "thalassemia" refers to a hemoglobinopathy that results from an altered ratio of α-like to β-like globin polypeptide chains resulting in the underproduction of normal hemoglobin tetrameric proteins and the accrual of free or unpaired α- or β-chains.

As used herein, the term "sickle-cell disease" refers to a group of autosomal recessive genetic blood disorders, which results from mutations in a globin gene and which is characterized by red blood cells that assume an abnormal, rigid, sickle shape. They are defined by the presence of $β^S$-gene coding for a β-globin chain variant in which glutamic acid is substituted by valine at amino acid position 6 of the peptide, and second β-gene that has a mutation that allows for the crystallization of HbS leading to a clinical phenotype. The term "sickle-cell anaemia" refers to a specific form of sickle-cell disease in patients who are homozygous for the mutation that causes HbS. Other common forms of sickle cell disease include HbS/β-thalassemia, HbS/HbC and HbS/HbD. Table 1 discloses the nucleotide sequences encoding the initial amino acids of a wild-type and sickle cell β-globin chains

TABLE 1

| β-globin chain | Sequence | Sequence Identifier |
|---|---|---|
| Wild-type | GTGCACCTCACTCCAGAGGAG | SEQ ID NO: 3 |
| Sickle | GTGCACCTCACTCCAGTGGAG | SEQ ID NO: 4 |

As used herein, the term "hereditary persistence of fetal hemoglobin" or "HPFH" refers to, a benign condition in which significant fetal hemoglobin (hemoglobin F) production continues well into adulthood, disregarding the normal shutoff point.

As used herein, the term "globin" refers to a family of heme-containing proteins that are involved in the binding and transport of oxygen.

As used herein, the term "homing endonuclease" or "HE" refers to a class of restriction endonucleases that are characterized by recognition sequences that are long enough to occur only once in a genome and randomly with a very low probability (e.g., once every $7 \times 10^{10}$ bp).

As used herein, the term "Transcription Activator-Like Effector Nuclease" or "TAL effector nuclease" or "TALEN" refers to a class of artificial restriction endonucleases that are generated by fusing a TAL effector DNA binding domain to a DNA cleavage domain.

As used herein, the term "three prime repair exonuclease 2" or "TREX2" refers to a nuclease having 3' exonuclease activity, which is typically involved in DNA replication, repair, and recombination.

As used herein, the term "Cas9 endonuclease" refers to an endonuclease that uses an RNA guide strand to target the site of endonuclease cleavage. The term "CRISPR endonuclease" refers to a Cas9 endonuclease in combination with an RNA guide strand. See, Jinek et al., *Science* 337:816-821 (2013); Cong et al., *Science* (Jan. 3, 2013) (Epub ahead of print); and Mali et al., *Science* (Jan. 3, 2013) (Epub ahead of print).

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

All references cited herein, whether supra or infra, including, but not limited to, patents, patent applications, and patent publications, whether U.S., PCT, or non-U.S. foreign, and all technical and/or scientific publications are hereby incorporated by reference in their entirety.

While various embodiments have been disclosed herein, other embodiments will be apparent to those skilled in the art. The various embodiments disclosed herein are for purposes of illustration and are not intended to be limiting, with the true scope and spirit being indicated by the claims.

Homing Endonucleases for Achieving
High-Efficiency, Multiplex Gene Disruption and
Gene Editing Functions As discussed above and exemplified below, the present disclosure provides compositions and methods comprising a polynucleotide that encodes one or more endonuclease(s), including one or more homing endonuclease(s) (HE(s)), such as one or more I-HjeMI homing endonuclease(s), I-CpaMI homing endonuclease(s), and/or I-OnuI homing endonuclease(s), and/or one or more Cas9 endonuclease in combination with one or more RNA guide strands, which may be transiently or persistently expressed in targeted cells shown to have clinical benefit in humans. Exemplary endonucleases target critical genomic regions that influence fetal hemoglobin production by: (a) disrupting a Bcl11a coding region or a Bcl11a gene regulatory region; (b) disrupting a HbF silencing DNA regulatory element or pathway, such as a Bcl11a-regulated HbF silencing region; (c) mutating one or more γ-globin gene promoter(s) to achieve increased expression of a γ-globin gene; (d) mutating one or more δ-globin gene promoter(s) to achieve increased expression of a δ-globin gene; and/or (e) correcting one or more β-globin gene mutation(s). The compositions and methods disclosed herein find utility in the treatment of hemoglobinopathies, including β-thalassemia and sickle cell disease.

The endonuclease coding sequences described herein may be expressed in combination with, or fused to, a DNA binding domain coding sequence, such as a TAL effector (TALE) coding sequence or a nuclease coding sequence such as a three prime repair exonuclease 2 (TREX2) coding sequence. Exemplified herein are TALE-HE fusion proteins and polynucleotides that encode one or more TALE-HE fusion protein(s).

Four protein scaffolds are known in the art for achieving targeted gene modification and disruption in eukaryotes: zinc finger nucleases (ZFNs), TAL effector nucleases (TALENs), homing endonucleases (HEs), and Cas9 endonucleases in combination with a RNA guide strand. The present disclosure employs TAL effector nucleases, homing endonucleases, and/or Cas9 endonucleases either alone or in combination. TAL nucleases offer more straightforward modular design and higher DNA recognition specificity than zinc finger nucleases while homing endonucleases, such as LAGLIDADG homing endonucleases (LHEs), offer highly specific cleavage profiles, compact structures, and, because they are compact monomeric proteins that do not require dimerization as do ZFNs and TALENs, the ability to be used in multiplex combinations. Accordingly, HEs and CRISPR endonucleases (i.e. Cas9 endonucleases in combination with one or more RNA guide strands) are extremely efficient in mediating gene disruption. Stoddard, supra and Mali et al., Science (2013), supra.

As part of the present disclosure, a critical region within the β-globin locus that suppresses HbF function has been identified. This region provides multiple targets for HE- and Cas9-mediated cleavage. Specifically-designed nucleases may be tested for activity against a cognate target site and for off-target activity against any closely related genomic targets. These HEs and Cas9 endonucleases in combination with one or more RNA guide strands may be engineered to avoid off-target genomic cleavage using the methods described in Stoddard, Structure 19:7-15 (2011) and Mali et al., Science (2013). HEs and Cas9 endonucleases in combination with one or more RNA guide strands that are disclosed herein are capable of directly targeting the γ- and δ-promoters and replacing a 606 bp region (SEQ ID NO: 14) that spans the majority of thalassemia mutations as well as the HbS mutation.

To facilitate the generation of large deletions spanning the HbF silencing region or subsets thereof one or more HEs and/or one or more Cas9 endonucleases in combination with one or more RNA guide strands may be co-transduced with a bridging oligonucleotide, which spans from the endonuclease cleavage site to the end of the target region. Chen et al., Nat. Methods 8(9):753-5 (2011). Higher frequency genome editing may be achieved by employing one or more HEs that bind to and cleave a sequence that flanks each side of the target region. Similarly, a HE and a mutagenizing oligonucleotide may be used to introduce promoter region mutations, which leads to elevated expression of a gamma or delta gene.

The presently disclosed HEs may be first evaluated in an erythroid cell line and in human CD34+ cells that are induced to differentiate to erythroid cells, thereby confirming the ability to alter globin gene expression. Depending upon the precise application contemplated, one, two, three, or more HEs may be delivered to facilitate the generation of larger deletions. The suitability of individual HEs can be assessed in additional culture and animal model assays to confirm their ability to target HSCs without compromising pluripotency and expansion potential, and to assess clinical benefit in hemoglobinopathy models. One or more HEs and one or more exonuclease, such as a TREX2 exonuclease or a TAL effector exonuclease, may be delivered to CD34+ HSC for the induction of targeted genetic deletions in critical regions for HbF.

Individual nucleases may be tested against a series of targets in a 350 bp region (SEQ ID NO: 2) defined by a region initiating at the edge of a repeat element and spanning through the upstream French HPFH breakpoint known to disrupt the Bcl11a occupancy region within the HbF silencing region and that includes a GATA-1 binding motif. Initial analyses have identified seven targets, evenly distributed throughout the region, which comprise DNA sequence modules for which pools of highly active endonuclease variants have been isolated and sequenced. Notably, one target overlaps with a potential Bcl11a binding motif and is adjacent to the GATA-1 motif. Successively larger deletions of a target region may be achieved by transducing two, three, or more HEs. Alternatively, multiple targets for disrupting the Bcl11a gene have been identified on the 5'-end of the gene to ensure the elimination of gene function. Similarly, multiple optimal targets for Cas9/RNA guide mediated disruption have been identified through the area that can be used singly, or in combination leading to larger deletions.

Individual HEs may be tested in transfected human cell lines using integrated genomic reporters, and may further employ additional selection steps to further optimize cleavage and gene conversion activities using protocols as described in Stoddard, supra. The validation and delivery of individual targeted HEs that are active against targets in the globin locus may be followed by vectorization of the nucleases in expression systems. For example, an expression system may be employed that links each HE to the coexpression of a nuclease, such as a TALEN and/or a TREX exonuclease, to achieve greatly enhanced gene disruption efficiency in transduced cells.

The present disclosure also provides TALE-HE fusion proteins, and polynucleotides that encode TALE-HE fusion proteins, which exhibit the desired feature of restricting the recruitment and activity of engineered HEs to the desired target site, such as within a globin locus, through the synergistic recognition of adjacent DNA targets by the TALE and HE scaffolds. Such TALE-HE fusions combine the most favorable properties of each scaffold (i.e., modular assembly of TALEs and nuclease specificity of HEs) while reducing nonspecific nuclease activity that is associated with traditional TALENs or zinc finger nucleases (ZFNs).

The high-resolution crystal structures have been determined for ten separate LAGLIDADG homing endonucleases (LHEs) in complex with their cognate DNA target sites. Stoddard, *Structure* 19:7-15 (2011) and Takeuchi et al., *Proc. Natl. Acad. Sci. U.S.A.* 108:13077-13082 (2011). Chimeric 'hybrids' of those LHEs have been constructed that, collectively, provide a broad range of LHE targeting proteins for gene-specific applications. Baxter et al., *Nucl. Acids Res.* 40(16):7985-8000 (2012).

HEs having suitable target sequence specificity may be identified by a yeast surface display strategy, combined with high-throughput cell sorting for desirable DNA cleavage specificity. A series of protein-DNA 'modules', which correspond to sequential pockets of contacts that extend across the entire target site, may be systematically randomized in separate libraries. Each library may then be systematically sorted for populations of enzymes that can specifically cleave each possible DNA variant within each module, and each sorted population deep-sequenced and archived for subsequent enzyme assembly and design. HEs that may be suitably employed in the compositions and methods of the present disclosure are commercially available (Pregenen, Seattle, Wash.).

Within certain aspects, the compositions and methods described herein may employ the co-expression of one or more HE, including, for example, one or more LHE, with a TREX2 3' exonuclease. In contrast to the 5' overhangs left by current versions of ZFNs and TALENs, HEs generate 3' overhangs at the site of targeted double-strand breaks, which results in an enhanced rate of end processing following HE cleavage. Near complete modification of a double strand break site in primary cells can be achieved through HE/TREX2 co-expression. Because of the way HE/TREX2 co-expression influences break processing, this combination achieves multiple targeted deletions in one region and increases the safety of nuclease-induced targeted gene disruption by diminishing break persistence and reducing the potential for large scale translocations mediated through alternative end joining pathways.

The crystal structure of a TAL effector (PthXo1) bound to its DNA target site has recently been determined. Mak et al., *Science* 335(6069):716-9 2012; e-pub 5 Jan. 2012 PubMed PMID: 22223736. These crystal structure data permit the precise definition of the boundaries of DNA recognition region and facilitates strategies for the creation of well-behaved TALEN-HE, or other TALEN-nuclease fusion construct, which may be applied to achieve a variety of complex genomic manipulations.

Genome Disruption to Bcl11a Gene Expression

Knockout of Bcl11a in a sickle cell mouse model ameliorates disease, supporting the clinical relevance of this pathway. Xu et al., *Science* 334:993-6 (2011). In addition, mice containing a YAC transgene spanning the human β-globin locus are used to model perturbations in Bcl11a mediated silencing of HbF. Heterozygous and homozygous knockout of the endogenous Bcl11a gene in these mice results in γ-globin mRNA comprising 20 and 76% of total β-like mRNA respectively, compared to 0.24% in controls. Sankaran et al., *Nature* 460:1093-7 (2009). This suggests Bcl11a acts as rheostat, modulating the degree of HbF suppression. Consistent with this, decrease of function mutations in Bcl11a result in elevated levels of HbF and a lessening of the clinical thalassemia and/or sickle cell disease phenotype. Galanello et al., *Blood* 114:3935-7 (2009).

Within certain embodiments, the present disclosure provides compositions and methods that comprise one or more endonuclease(s), including one or more homing endonuclease(s) (HE(s)), such as one or more I-HjeMI homing endonuclease(s), I-CpaMI homing endonuclease(s), and/or I-OnuI homing endonuclease(s), and/or one or more Cas9 endonuclease(s) to achieve the disruption of a sequence that encodes Bcl11a or its key regulatory sequences. As described in greater detail and exemplified herein, compositions and methods comprising one or more Cas9 endonucleases further comprise one or more Bcl11a gene-specific RNA guide strands to mediate the targeting of the Cas9 endonuclease to a Bcl11a gene sequence.

The Bcl11a gene has multiple exons spanning over 100 kb and results in several splice variants that lead to proteins associated with different activities. As part of the present disclosure, several DNA targets have been identified that are transcribed into multiple Bcl11a splice variants. All disrupt the long (L) and extra-long (XL) forms, which are associated with the greatest HbF silencing activity, while one disrupts all forms of Bcl11a. These targets comprise DNA sequence modules for which pools of highly active endonuclease variants have been isolated and sequenced. The human Bcl11a cDNA sequence (CCDS1862.1) is presented herein as SEQ ID NO: 24 (FIG. 10).

Thus, within certain aspects, the present disclosure provides compositions for achieving therapeutic levels of HbF, which compositions comprise a polynucleotide encoding one or more homing endonuclease (HE), which is capable of mediating the disruption of the nucleotide sequence within this 1.3 kb region, thereby preventing the binding of Bcl11a, and the formation of the corresponding repressive complex, and de-repressing γ-globin expression.

Genome Disruption to Block Bcl11a-Mediated Silencing of HbF

As summarized above, within certain embodiments, the present disclosure provides compositions and methods for treating and/or ameliorating a genetic disease, such as a hemoglobinopathy, including a thalassemia and/or sickle cell disease. Certain aspects of these embodiments include the transient expression of a polynucleotide encoding one or more homing endonuclease(s) to disrupt a HbF silencing element or pathway within a β-globin gene locus or a δ-globin gene locus thereby increasing to therapeutic levels the expression of an endogenous gene such as a γ- or δ-globin gene.

The compositions disclosed herein comprise a polynucleotide encoding one or more homing endonuclease(s) (HE(s))

and or one or more Cas9 endonuclease in combination with one or more RNA guide strands and, optionally, one or more transcription activator-like (TAL) effector(s), to achieve the targeted disruption of key regulatory sequences within the β-globin gene locus. More specifically, the compositions and methods disclosed herein achieve an increase in γ-globin gene expression, and consequent HbF protein production, by removing essential elements for Bcl11a binding to the HbF silencing region(s) within the β-globin gene locus.

During normal development, expression of an embryonic β-like gene (ε-globin) is sequentially replaced by a pair of γ-globin genes in the fetus and the δ- and β-globin genes in the adult. In adult erythroid tissues, the zinc finger protein Bcl11a binds to a region between the γ-globin and δ-globin genes within the β-globin gene locus thereby silencing the production of HbF. The importance of Bcl11a-mediated silencing of HbF is supported by knockdown of Bcl11a mRNA in human CD34 cells, which increases HbF levels to 24-36% of total β-like proteins. Sankaran et al., *Science* 322:1839-42 (2008). Removal of this region in the deletion form of HPFH, as well as the knockdown of Bcl11a, blocks Bcl11a-mediated HbF silencing and results in an elevated level of γ-globin gene expression and HbF protein production in adult erythroid tissues (Sankaran et al., *N. Engl. J. Med.* 365:807-14 (2011)).

While multiple mechanisms contribute to an elevation in HbF protein levels, it has been shown that a 3.6 kb region is key for HbF silencing (SEQ ID NO: 1). Sankaran et al., *N. Engl. J. Med.* 365:807-14 (2011). While there are several peaks of Bcl11a enrichment in the β-globin locus, the single peak in the 3.6 kb HbF silencing region stands out as proteins known to form a repressive complex with Bcl11a are bound in this region (GATA-1 and HDAC-1) and the chromatin is enriched for the repressive histone mark trimethylation of histone H3 on lysine27.

Notably this 3.6 kb region contains a single peak of Bcl11a binding downstream of the γ-gene. Multiple point mutations have been identified in the γ-globin promoters that result in HbF levels of 20-30% as a heterozygote, ameliorating thalassemia and SCD. These point mutations cluster to three regions all within 200 bp of the γ-cap sites: (1) -200, a GC-rich region bound by SP1 and a stage specific protein complex; (2) -175, bound by GATA-1; and (3) Oct1 and a CCAAT motif at −117 bound by several addition factors. Forget, *Ann. NY Acad. Sci.* 850:38-44 (1998).

Mutations within these three regions block the binding of a repressive complex in adult erythroid cells. Consequently, these regions are suitable targets for HE-mediated disruption and targeted mutation by the compositions and methods disclosed herein. The disruption of these regions leads to a decrease in repressive complexes, which results in an elevated level of γ-globin gene expression, and a corresponding increase in HbF protein production to levels that are sufficient to achieve therapeutic efficacy in methods for the treatment of hemoglobinopathies, including β-thalassemia and sickle cell disease.

A single peak of Bcl11a occupancy is present within the 3.6 kb HbF silencing region (Sankaran et al., *N. Engl. J. Med.* 365:807-14 (2011)) ((SEQ ID NO: 1). This region of Bcl11a occupancy is disrupted by the upstream breakpoint of French HPFH Sankaran et al., *N. Engl. J. Med.* 365:807-14 (2011). Described herein is a 350 bp region initiating at the edge of a repeat element and spanning through the upstream French HPFH breakpoint known to disrupt the Bcl11a occupancy region within the HbF silencing region and that includes a GATA-1 binding motif (SEQ ID NO: 2). The base before the upstream French HPFH deletion is HG18 chr11:5,214,023. The GATA-1 motif spans chr11:5,214,200-5,214,206 Without being limited by theory, it is believed that GATA-1 and HDAC-1 form a repressive complex with Bcl11a when Bcl11a is bound within this 350 bp region and this leads to the formation of a repressive complex that inhibits the expression of the γ-globin genes and, thereby, reduces cellular levels of HbF protein.

The HE-mediated disruption, which is achieved by the compositions and methods disclosed herein, occurs at high efficiency. Unlike shRNA knockdown approaches that are known in the art, the highly sequence specific disruption of the HbF silencing region, which is mediated by the homing endonucleases disclosed herein, avoids off target effects at other Bcl11a binding sites in the genome, and in other cell types, especially within B-cells where Bcl11a binding is required for normal development.

Thus, the homing endonucleases described herein exhibit unique advantages over conventional gene targeting nucleases. Because they are broadly efficacious regardless of genotype, the homing endonucleases described herein are not patient specific and provide clinical benefit in the heterozygotic state.

Recapitulation of Genetic Modifications for Correcting a Thalassemia or Sickle Cell Disease Mutation Within other embodiments, the present disclosure provides compositions and methods for recapitulating, via genome editing, one or more naturally-occurring mutation(s) within a patient's genome to provide clinical benefits. More specifically, the present disclosure provides compositions and methods for achieving the direct correction of a thalassemia and/or sickle cell disease (SCD) mutation through genome editing.

The compositions and methods disclosed herein employ a correction template to achieve gene editing and correction to ameliorate hemoglobinopathies, including thalassemias and sickle cell disease, by enhancing the rate of homologous recombination (HR) between the correction template and the corresponding mutated sequence within a patient's genome. Exemplified herein are compositions and methods for correcting an underlying β-globin mutation, which provide clinical benefit in the heterozygotic state while avoiding the insertion of vector sequences. These compositions and methods may be used independently from or in combination with the compositions and methods described above for the disruption of Bcl11a-mediated gene silencing.

The present disclosure provides a robust set of technologies for genome editing that exploits the advantages of HEs, as compared to alternative platforms that are available in the art. These HEs can be combined with a TAL effector modular DNA binding platform to achieve additional therapeutic advantages.

While homologous recombination (HR) to edit genomes is powerful, it is inefficient. Introduction of a double stranded break at the region to be modified results in a tremendous increase in HR efficiency. Simultaneous introduction of a polynucleotide encoding a HE and a correction template, wherein the correction template comprises as little as 100 bp of flanking homology, allows an increased frequency of HR, thereby permitting genome editing as the corrective template is introduced.

The transduction of cells with a short synthesized correction template may also be employed for the efficient introduction of defined single base-pair mutations. Such approaches typically exploit a single HE. Alternatively HEs may be transduced that flank the region targeted for modification. Correction templates may be transduced by optimized methods as described herein. The design, transduction, and evaluation of HEs may be performed, as discussed in detail below, according to the methodology described in Certo et al., *Nat Methods* 8:671-6 (2011) and Jarjour et al., *Nucleic Acids Res* 37:6871-80 (2009).

Within certain aspects of these embodiments, one or more homing endonuclease(s) is/are employed in combination with a normal or wild-type polynucleotide sequence to permit the editing and/or repair of one or more β-like globin gene(s). For example, the present disclosure provides compositions and methods for the treatment of hemoglobinopathies, which compositions and methods permit the modification of key regulatory and/or coding sequences within a gene locus, exemplified herein by the human β-globin gene locus, through the transient expression of a polynucleotide that includes one or more naturally occurring mutation(s).

More specifically, the present disclosure provides compositions and methods for genome editing, which may be employed to generate mutations that recapitulate naturally-occurring mutations within stem cells, including, for example, hematopoietic stem cells (HSCs), embryonic stem (ES) cells, and induced pluripotent stem cells (iPSCs). Genome edited HSCs, ESs, and iPSCs, including autologous HSCs and iPSCs, may be transplanted into a patient to treat one or more hemoglobinopathies, such as a thalassemia and/or sickle cell disease. The compositions and methods disclosed herein permit the efficient modification of HSCs, ESs, and iPSCs, without the need for the persistent expression or insertion of an exogenous gene to achieve the amelioration of hemoglobinopathies in mature erythroid cells and in patient cells in vivo.

Because these therapeutic methods do not require the integration and/or persistent expression of a transgene, the safety concerns associated with currently available gene therapy technologies are obviated. Within certain aspects of these embodiments, the compositions and methods employ one or more polynucleotide for the targeted disruption of Bcl11a-mediated silencing of HbF.

Exemplified herein are compositions and methods that permit the recapitulation of genetic modifications within one or more HbF silencing region(s) that is/are responsible for hereditary persistence of HbF (HPFH). Because such genetic modifications lead to increased expression of a therapeutically effective gene, the recapitulated genetic modifications need only be present as a heterozygote to achieve therapeutic efficacy.

The compositions and methods for ameliorating thalassemia and sickle cell disease that are disclosed herein achieve therapeutic efficacy by introducing one or more mutation that result in increased HbF and/or HbA$_2$ and/or HbA protein production. Exemplified herein are compositions and methods for recapitulating one or more naturally-occurring deletion(s) of the β-globin gene and/or regions, which activate γ-globin gene expression thereby increasing levels of fetal hemoglobin. Because a modest increase in HbF and/or HbA$_2$ protein production is sufficient to ameliorate these disease phenotypes, heterozygotic mutations are sufficient to achieve substantial therapeutic benefit.

Within certain aspects, the delivery of a correction template may be done in conjunction with the delivery of a selectable marker gene thereby permitting the selection of corrected cells ex vivo and in vivo, although such an approach requires long-term expression via integration of the selectable marker gene. Beard et al., *J. Clin. Invest.* 120:2345-54 (2010) and Munoz et al., *Nucleic Acids Res.* 39(2):729-743 (2011).

Activation of β-globin expression in adult tissues depends upon binding of KLF-1 at a CACCC box in its promoter. The δ-globin promoter lacks an intact CACCC box, KLF-1 is not bound and expression is limited to 2% of β-globin. Mutations of the δ-promoter that recapitulate the β-globin promoter by, for example, introducing an intact CACCC box, allow KLF-1 binding, and result in a therapeutically efficacious increase in δ-globin expression.

Within certain aspects of these embodiments, a non-deletion HPFH γ-globin promoter mutation may be generated. Only a single base pair must be modified to achieve efficacy. For example, a −175 T→C mutation (SEQ ID NO: 21) may be recapitulated to maximize the levels of HbF. Mutation of any of the four γ-globin genes will provide benefit, thus increasing potential targets.

Delivery of Homing Endonucleases, Cas9 Endonuclease, TAL Effector Nucleases, and TREX2 Exonucleases Within further embodiments, the present disclosure provides systems, in particular non-integrating vector systems, for the delivery of one or more HE, Cas9, TALEN, and/or TREX2 nuclease described herein. There are three major challenges to the therapeutic gene editing of hematopoietic stem cells (HSCs): (1) nuclease reagents must be transiently delivered to HSCs; (2) gene editing efficiency in cells receiving a nuclease must be high; and (3) gene-edited HSCs must engraft to a level sufficient for therapeutic effect. These challenges may be overcome by employing various vectorization approaches.

Exemplified herein are cocal pseudotyped lentiviral vectors and foamy virus vectors for the efficient gene transfer to HSCs. Trobridge et al., *Mol Ther* 18:725-33 (2008). Alternatively, adenoviral vectors may be modified as previously described for use in gene transfer to HSCs. Wang et al., *Exp. Hematol.* 36:823-31 (2008) and Wang et al., *Nat. Med.* 17:96-104 (2011). Within other aspects of these embodiments, AAV-based vector systems may also be employed for the delivery of HEs, Cas9 (and/or RNA guide strands), TALE-HE, TALENs, and/or TREX2 nucleases.

AAV6-serotype recombinant AAV vectors provide a 4.5 kb payload, sufficient to deliver a promoter-HE-exonuclease or a promoter-TAL-HE fusion-exonuclease cassette in addition to a small recombination template. Alternatively, it can carry the small Cas9 polypeptide and guide RNAs. AAV6 provides efficient transduction of human CD34+ umbilical cord blood cells of all known AAV capsids and is able to mediate significant levels of transient gene expression in HSC. Self-complementary and single stranded AAV6 vectors may be employed for both gene knockout and recombination-based gene editing in HSC in cell lines and in primary CD34+ cells.

Adenoviral vectors with hybrid capsids are capable of efficiently transducing many types of hematopoietic cells including CD34+ cells. Improved transduction may be achieved with a chimeric adenoviral vector using the serotype 35 fiber (Ad5-F35) and the serotype 11 fiber (Ad5-F11) for efficient transduction of hematopoietic cells. Helper-dependent adenoviral vectors offer up to a 30 kb payload, along with transient gene expression in HSC, and can be used to deliver multiple HE/exonuclease cassettes, HE-TAL fusions, as well as very large recombination templates. Alternatively it can carry the small Cas9 polypeptide and guide RNAs. These modified chimeric adenovirus vectors may, therefore, be employed for both gene knockout and recombination-based gene editing in HSC.

Integration-deficient lentiviral and foamyviral vectors (IDLV and IDFV) provide 6 kb (IDLV) to 9 kb (IDFV) payloads, and have well documented capabilities to transduce human HSCs. Within certain aspects, both IDLV and IDFV vectors may be employed for gene knockout and recombination-based gene editing in HSC. IDLV with alternative promoter GFP cassettes provide efficient and high level expression in CD34+ HSC. High titer stocks may be achieved using a TFF purification step. Vectors with a set of promoter/GFP cassettes may be used to provide efficient and high level HE expression in CD34+ HSC and may be generated to express individual HEs, HE/Trex2, multiplex-HE (i.e., two, three, or four HEs that are co-expressed), and multiplex-HE/TREX2 combinations. Multiplex HE expression permits multiple cleavage events in a critical region, which depending upon the precise application, may be desired to create increased HbF de-repression. Such multiplex strategies are feasible with LHEs, because they function autonomously, and may be satisfactorily employed in combination with TREX2 co-expression to permit highly efficient and synchronous processing of closely-targeted double strand breaks. Alternatively it can carry the small Cas9 polypeptide and guide RNAs.

The efficiency of gene targeting, levels of globin gene expression in individual targeted cells as well as populations of cells and of their progeny, the effect of targeting on erythropoiesis and on stem cell function, and on hematologic parameters and organ function may be confirmed in model organisms.

Transductions may be followed by single-cell and bulk population assessments of modification efficiency and expression of β-like genes at the RNA and protein levels. Alterations in factor binding and chromatin structure may be assessed, as well as morphology, the extent of ineffective erythropoiesis and apoptosis. Candidates that score well in initial screens may be further assessed for effects on HSC pluripotency as well as the ability to ameliorate disease specific phenotypes in vitro and in vivo.

Initial screening of HE candidates and delivery systems may be performed in a mouse erythroleukemia cell line containing a single intact human chromosome 11 (N-MEL) and clinical grade CD34+ normal human HSCs with endpoints of assessing targeted mutation efficiency and globin gene expression. Both cell types can be induced to differentiate along an erythroid path during which expression of β-like genes is highly induced with high β- to γ- and δ-ratios allowing a quantitative assessment of effects globin gene regulation at a single-cell and population level. Second level assessments may include an analysis of the pluripotency of transduced CD34+ cells and erythropoiesis. Suitable assay systems may include culturing to assess long-term proliferative potential, analysis of myeloid and erythroid colonies for clonal analysis and transplant into NOD SCID gamma (NSG) mice followed by assessment of multilineage engraftment of primary and secondary recipients. Clinical effectiveness may be assessed simultaneously in vitro and in vivo.

Knockout of murine Bcl11a leads to a dramatic dose-dependent increase in γ-globin in mice containing a human β-globin locus and ameliorates the sickle phenotype in humanized mouse models. While both systems allow the analysis of globin gene expression, the sickle mice allow for the assessment of the improvement of phenotype in these mice with special attention to the hematologic parameters, liver and lung pathology, renal function and spleen size. Phenotypic improvement may be correlated to the number of HbF containing cells, the HbF/HbS ratio and expression patterns in single cell assays.

In addition, erythrocyte lifespan and morphology may be assessed by transducing human CD34+ HSCs from hemoglobinopathy patients. Cultured thalassemic cells show minimal expansion, a lack of hemoglobinization, evidence of ineffective erythropoiesis and increased apoptosis compared to normals. These features permit the quantitative assessment of expression levels and degree of erythropoiesis post-targeting. The degree of sickling of erythroid progeny of CD34+ cells under hypoxic conditions may also be assessed. CD34+ cells from patients may be transplanted into NSG mice, after which several features of abnormal erythropoiesis are be recapitulated, allowing assessment of the effect of targeted mutagenesis.

Expansion of Autologous HSCs, ESs, and iPSC-Derived HSCs

Within further embodiments, the present disclosure provides compositions and methods for the ex-vivo expansion of modified hematopoietic stem cells (HSCs) to allow for efficient engraftment of corrected cells and the use of induced pluripotent stem cells (iPSCs) for screening and clinical application. Within certain aspects of these embodiments are provided compositions and methods for the efficient expansion of autologous HSCs, autologous gene-modified HSCs, ESs, and iPSC-derived HSCs. Cord blood expansion methodology may be employed, which methodology utilizes Delta1 in serum free media supplemented with hematopoietic growth factors using mobilized peripheral blood CD34+ obtained from normal donors. These compositions and methods may be used in combination with one or more additional reagent to enhance the survival and proliferation of hematopoietic stem/progenitor cells. Within other aspects, these compositions and methods may employ endothelial cell co-cultures for the enhanced expansion of long-term repopulating cells, including corrected iPSC-derived HSCs.

For effective clinical translation of the presently disclosed gene correction strategies, the present disclosure provides methods for the ex vivo expansion of the absolute number of corrected autologous HSCs. Gene correction procedures are generally more efficient if done in a smaller scale and often only limited numbers of HSCs are available for correction. Thus, it is contemplated by the present disclosure that expansion methods may be employed to permit clinically feasible ex vivo expansion of corrected HSCs, ESs, and/or HSCs derived from induced pluripotent stem cells (iPSCs). Within certain aspects, the present disclosure provides methods for expanding hematopoietic stem/progenitor cells for therapeutic application by exploiting the role of Notch signaling in determining stem cell fate. Dahlberg et al., *Blood* 117:6083-90 (2010); Delaney et al., *Nat Med* 16:232-6 (2010); and Varnum-Finney et al., *Nat Med* 6:1278-81 (2000).

These methods permit the clinically relevant ex vivo expansion of cord blood stem/progenitor cells, and an expanded cellular therapy for treatment of myelosuppression in patients undergoing cord blood transplantation, by first using a partially HLA-matched fresh product (harvested post-culture and infused directly) and/or by using a previously expanded and cryopreserved product as an off-the-shelf non-HLA matched cellular therapy.

Ex vivo expansion of gene-corrected autologous HSCs enhances the safety and effectiveness of HSC-based gene therapy by permitting the transplantation of greater numbers of appropriately corrected repopulating cells to allow for rapid repopulation and ensures predominance of gene-corrected cells in vivo. Accordingly, the present disclosure provides compositions and methods for the supportive care via a third-party, non HLA-matched, donor ex vivo expanded stem/progenitor cell, which is capable of providing rapid but transient myeloid recovery, essential to reduce the risk of early transplant related mortality secondary to infections that is observed after myeloablative T cell depleted autologous transplants. Delaney et al., *Nat Med* 16:232-6 (2010).

Agents that inhibit differentiation (e.g., the Notch ligand) may be combined with compositions and methods that enhance the proliferation and survival of early stem/progenitor cells thereby achieving improved Notch-mediated ex vivo expansion. Enhanced proliferation of cord blood stem/progenitor cells may be achieved by combining the Notch ligand, Delta1, with the aryl hydrocarbon receptor inhibitor (SR1) (Boitano et al., *Science* 329:1345-8 (2011)) or HoxB4 (Watts et al., *Blood* 116:5859-66 (2010) and Zhang et al., *PLoS Med* 3:e173 (2006)) to enhance proliferation and self-renewal of hematopoietic precursors, and with angiopoietin-like 5 to enhance their survival. Essential to the clinical application of gene therapy is the ability to expand long-term repopulating cells, assuring longevity of the corrected cell graft.

Akt-activated endothelial cells may be employed in co-culture systems to confirm expansion of gene-corrected cells. Butler et al., *Cell Stem Cell* 6:251-64 (2011). Expansion of gene-corrected cells depends upon endothelial cell-induced activation of Notch signaling in the hematopoietic precursors. A second critical aspect for clinical application is the genetic and epigenetic fidelity of the derived cells as compared to their normal counterparts to ensure appropriate behavior and lack of oncogenic potential in vivo. Importantly, genome-wide assessment of expanded cord blood stem/progenitor cells exhibit fidelity of the transcriptome, chromatin structure, and the DNA methylome in comparison with primary isolated CD34+ cells.

Expansion strategies in normal CD34+ cells may be employed in conjunction with defined methods that utilize CD34+ cells from patients with hemoglobinopathies. Cord blood expansion methodology may utilize Delta1 in serum free media supplemented with hematopoietic growth factors using mobilized peripheral blood CD34+ obtained from normal donors. Optimized ex vivo expansion conditions using established in vitro assays (immunophenotyping, growth, etc) and in vivo repopulating ability may be assessed using the NSG mouse model. Optimized conditions may be used in combination with compositions that include SRI (aryl hydrocarbon receptor inhibitor), Hox proteins, or angiopoietins to enhance the proliferation and survival of early stem/progenitor cells. Promising combinations may be evaluated in progenitor cell in vitro assays and in the immunodeficient mouse model (NSG mice) and then extended from expansion of CD34+ from normal individuals to evaluate these methods for expansion of CD34+ cells from patients with thalassemia (and other hemoglobinopathies).

The transcriptional, genetic, and epigenetic fidelity of expanded cells with their normal counterpart HSCs may be assessed using genome wide approaches to assess the oncogenic potential of the generated cells. Following growth in vivo (after infusion), cells may be used to determine whether there are functionally significant aberrations that enhance in vivo growth of any affected clone(s), thereby allowing selective expansion and detection of rare cells.

Cellular Therapies to Abrogate Post-Transplant Neutropenia and to Improve Outcome Following Transplantation of Gene-Corrected Autologous HSCs Within another embodiment, the present disclosure provides compositions and methods for providing supportive care, which compositions and methods comprise off-the-shelf cellular therapies that abrogate post-transplant neutropenia and improve outcome following transplantation of gene-corrected autologous HSCs. Ex vivo expanded, cryopreserved cord blood (CB) stem/progenitor cells may, for example, be administered as a means of supportive care to patients with thalassemia and/or sickle cell disease who are undergoing myeloablative HCT with autologous CD34+ gene corrected cells.

In studies aimed at developing an economically feasible "off-the-shelf" source of progenitor cells capable of providing rapid neutrophil recovery, a bank of pre-expanded, cryopreserved hematopoietic stem/progenitor cell products was generated—each being derived from a single CB unit that can be held for future clinical use.

The safety of administering this "off-the-shelf" non-HLA matched product to adults was demonstrated immediately following first salvage chemotherapy for relapsed/refractory AML, as well as in the myeloablative CBT setting in pediatric and adult patients with hematologic malignancy.

It has been hypothesized that this expanded cell product, which is devoid of T cells, can be infused as an off-the-shelf cellular therapy to provide rapid but temporary myeloid engraftment and to potentially facilitate autologous hematopoietic recovery in patients undergoing myeloablative HCT with autologous gene-corrected stem cell grafts, thereby reducing the infectious complications and risk of mortality.

Critical is the question of whether HLA-matching is required for safe infusion of an "off-the-shelf" non-HLA matched product, which is devoid of T cells. Without the need for HLA matching, fresh CB units can be collected for immediate ex vivo expansion and the final product cryopreserved for future on demand use. Patient access to an off-the-shelf expanded CB product is dramatically enhanced as all of the expanded products banked would be potentially available for any given patient, regardless of HLA typing, race/ethnicity or location of the patient.

Moreover, the ability to create an off-the-shelf universal donor expanded cell therapy is not only promising to shorten the duration of severe neutropenia post HCT, it is also likely to enhance more broad areas of investigation outside of stem cell transplantation, e.g., as a way of providing temporary myeloid engraftment for treatment of chemotherapy induced severe neutropenia, any acquired severe neutropenia or accidental radiation exposure.

Ex vivo expansion abrogates the risks of CBT by overcoming delayed hematopoietic recovery and a significant improvement in overall survival will result. A reduced risk of relapse has been observed in patients undergoing double CBT, and chronic GVHD is lower despite highly mismatched grafts. If the risk of early transplant related mortality can be reduced by infusion of ex vivo expanded cord blood progenitors to enhance hematopoietic recovery, overall survival is likely to exceed that seen with conventional unrelated donors.

Within further embodiments, the present disclosure provides cellular therapies to abrogate post-transplant neutropenia and to improve outcome following transplantation of gene-corrected autologous HSCs. Patients with thalassemia who undergo myeloablative HCT with autologous gene corrected cells are at increased risk of infections and mortality secondary to limiting numbers of CD34+ cells in the infused graft (until ex vivo expansion of these gene corrected cells to clinically feasible numbers are achieved). Infusion of a previously expanded and cryopreserved cord blood progenitor cell product as an off-the-shelf supportive care measure can be employed to reduce the risk of mortality by contributing to early, but transient, myeloid recovery until the long term graft contributes to hematopoietic recovery.

Patients who undergo myeloablative HCT experience severe pancytopenia as a direct consequence of the conditioning regimen, and all patients are at increased risk of infection and bleeding during this time. The time to hematopoietic recovery (of neutrophil and platelets) is directly influenced by the CD34+ cell dose, and thus, for those patients undergoing myeloablative HCT with umbilical cord blood where the stem cell dose is $\frac{1}{10}^{th}$ of a conventional donor graft or with autologous CD34 enriched low cell dose grafts, the risk of transplant related mortality due to delayed hematopoietic recovery is even greater.

To overcome these risks and to increase the safety of these HCT approaches, there is a great need for novel therapies that can abrogate prolonged pancytopenia and facilitate more rapid hematopoietic recovery. As discussed above, such a strategy has been developed wherein the absolute number of marrow repopulating cord blood (CB) hematopoietic stem/progenitor cells (HSPC) can be increased by culture with the Notch ligand Delta1. Infusion of these partially HLA-matched ex vivo expanded CB cells into children or adults undergoing cord blood transplantation (CBT) has been demonstrated to be safe and can significantly shorten the time to reach an initial absolute neutrophil count of 500 from 26 to 11 days, as a result of rapid myeloid engraftment contributed by the expanded cells.

In more recent studies aimed at developing an economically feasible "off-the-shelf" source of progenitor cells capable of providing rapid neutrophil recovery, we have generated a bank of pre-expanded cryopreserved hematopoietic stem/progenitor cell products, each derived from a single CB unit that can be held for future clinical use. We have now also demonstrated the safety of administering this "off-the-shelf" non-HLA matched product to adults immediately following first salvage chemotherapy for relapsed/refractory AML, as well as in the myeloablative CBT setting in pediatric and adult patients with hematologic malignancy. We hypothesize that this expanded cell product which is devoid of T cells can be infused as an off-the-shelf cellular therapy to provide rapid but temporary myeloid engraftment and to potentially facilitate autologous hematopoietic recovery in patients undergoing myeloablative HCT with autologous gene-corrected stem cell grafts, thereby reducing the infectious complications and risk of mortality.

Using the defined optimal methods for generation of ex vivo expanded cord blood stem/progenitor cells, a bank of off-the-shelf expanded cell products may be employed to determine the safety of infusing these cells as supportive care in an autologous gene-corrected HCT.

The present disclosure will be best understood in view of the following non-limiting Examples.

EXAMPLES

Example 1

Selection of Bcl11a Gene Targeting Homing Endonucleases Based on I-HjeMI, I-CpaMI, and I-OnuI Using In Vitro Compartmentalization (IVC)

Figure 11:
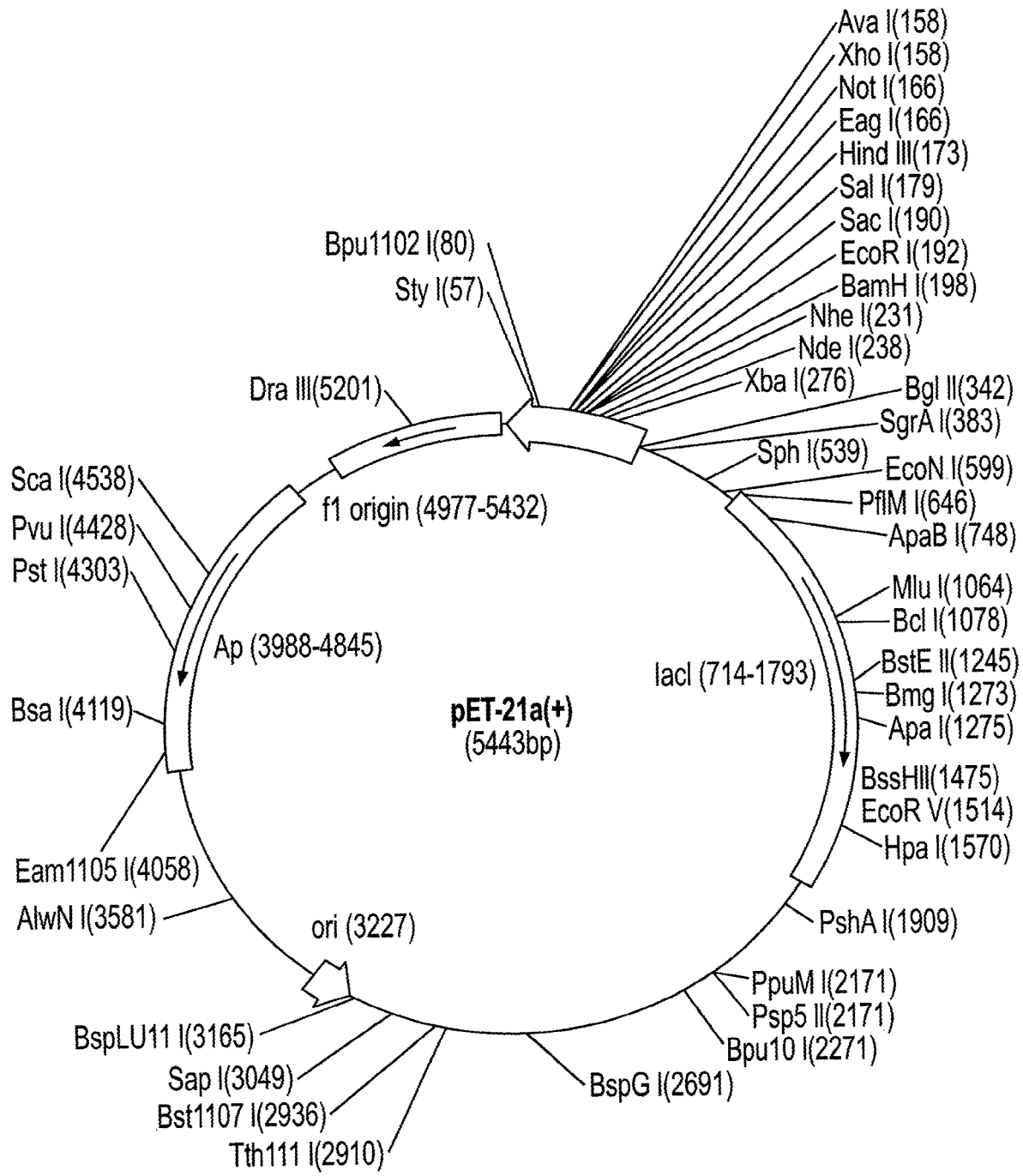
FIG. 11 is a restriction map for the plasmid pET-21a(+).

The open reading frame (ORF) of a parental LAGLIDADG homing endonuclease (LHE), I-HjeMI (FIG. 14; SEQ ID NO: 28; Jacoby et al., *Nucl. Acids Res.* 40(11): 4954-4964 (2012); Taylor et al., *Nucl. Acids Res.* 40(Web Server issue):W110-6 (2012)), codon optimized for expression in *E. coli*, was cloned between the NcoI and NotI restriction sites of pET21-a(+) (FIG. 11; EMD Millipore (Novagen) division of Merck KGaA. To introduce site-directed saturation mutagenesis into the ORF of I-HjeMI, DNA fragments containing its partial ORF with approximately 20 base pairs of a region overlapped with flanking fragments on both sides were PCR-amplified using primers that contained degenerate codon 5'-NNK-3'(coding all 20 amino acids). Amino-acid residues mutated using such PCR primers are shown in Table 2. PCR products were purified by extraction from an agarose gel, and assembled in a subsequent round of PCR with a sequence containing 2 copies of target sites for variant endonucleases to be selected. Successfully assembled DNA fragment was again purified by gel extraction, and used as a library in in vitro compartmentalization (IVC).

Three rounds of IVC were conducted after each round of site-directed saturation mutagenesis in order to enrich variant nuclease genes with altered specificity. The oil-surfactant mixture (2% ABIL EM 90 (Evonik Industries AG Personal Care, Essen, North Rhine-Westphalia, Germany), 0.05% Triton X-100 in light mineral oil) was thoroughly mixed with the saturation buffer (100 mM potassium glutamate (pH 7.5), 10 mM magnesium acetate (pH 7.5), 1 mM dithiothreitol and 5 mg/ml bovine serum albumin), incubated at 37° C. for 20 minutes, and centrifuged at 16,000× g for 15 minutes at 4° C. Five hundred microliters of the upper phase was used to emulsify 30 µl of the in vitro protein synthesis mixture (25 µl of PURExpress (New England Biolabs, Ipswich, Mass.), 20 units of RNase inhibitor, 1 mg/ml bovine serum albumin, and 8 ng of a DNA library) by constant stirring at 1,400 r.p.m. for three and a half minutes on ice. The emulsion was incubated at 30° C. for 4 hours, and then heated at 75° C. for 15 minutes. Emulsified droplets were collected by centrifugation at 16,000×g for 15 min at 4° C., and broken by an addition of phenol/chloroform/isoamyl alcohol. Nucleic acids were recovered by ethanol precipitation, and treated with RNase cocktail (Life Technologies Corporation (Invitrogen), Grand Island, N.Y.). After purification using QIAquick PCR purification kit (Qiagen, Hilden, Germany), a DNA library was ligated with a DNA adaptor with a 4-base 3' overhang sequence complementary to the cohesive end of a target site generated by endonuclease variants expressed in emulsified droplets, and added to PCR mixture containing a pair of primers, one of which was specific for the ligated DNA adaptor in order to enrich genes of variant endonucleases linked to a cleaved target site. A PCR amplicon was gel-purified and the ORF of variant genes was further PCR-amplified to prepare a DNA library to be used in the subsequent round of IVC.

In the second round of IVC, an emulsion was made with 1 ng of a reconstructed library, and incubated at 42° C. for 75 minutes before quenching in vitro transcription/translation reaction by heating at 75° C. The DNA library was recovered and active endonuclease genes were specifically enriched by PCR following ligation with a DNA adaptor as described above.

In the third round of IVC, an in vitro protein synthesis mixture containing 0.5 ng of a library fragment was emulsified in 4.5% Span 80/0.5% Triton X-100/light mineral oil. The reaction ran at 42° C. for 45 minutes and was heat-inactivated at 75° C. After extraction from emulsion, cleaved target site-associated endonuclease genes were PCR-amplified and subjected to the subsequent round of site-directed mutagenesis.

Figure 13:
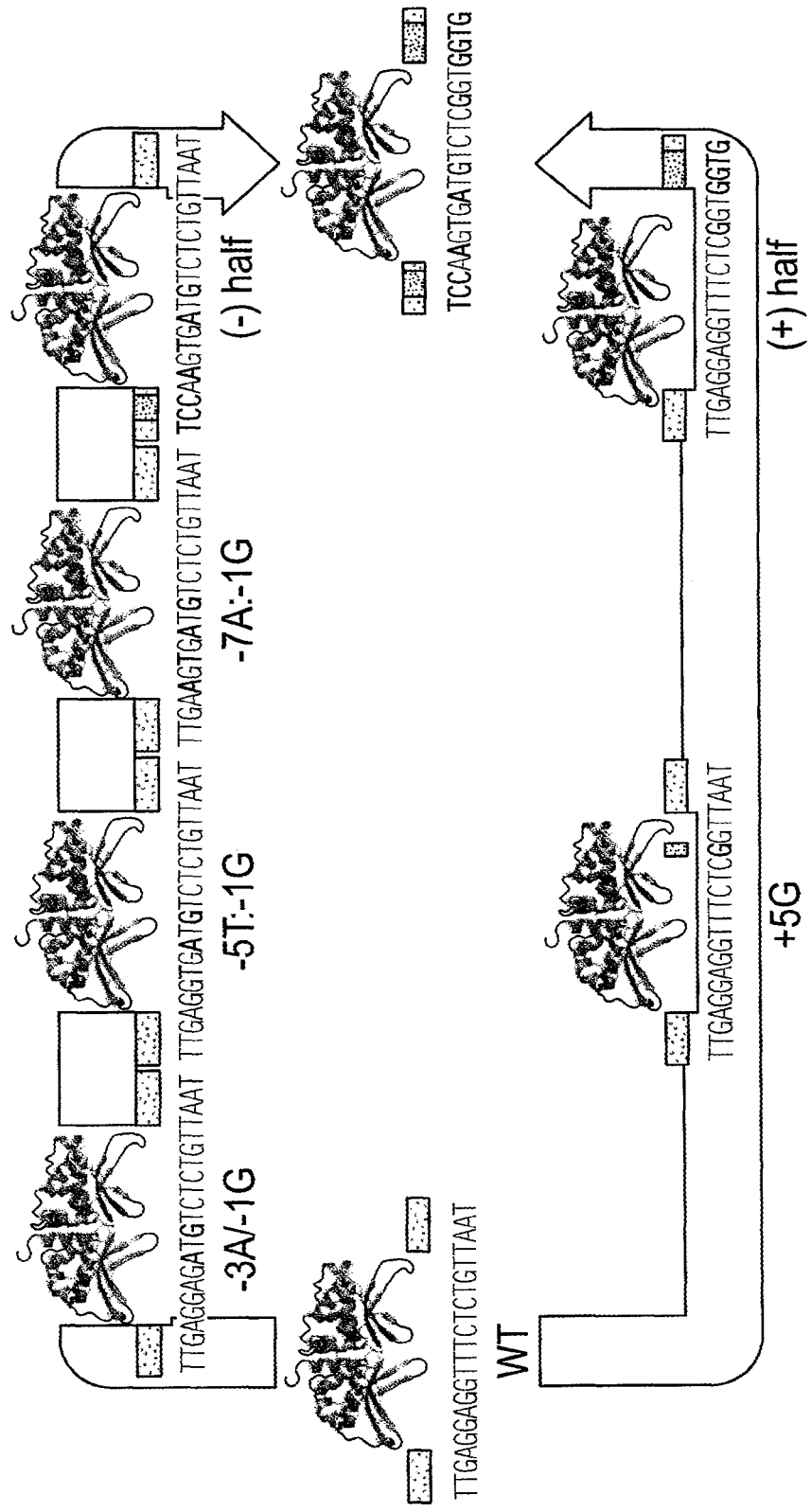
FIG. 13 is a schematic diagram of directed evolution for creating the BCL11A gene-targeting endonuclease. A constructed library was subjected to selection in IVC against a target site, a portion of which was replaced with the BCL11A gene target.
Figure 20:
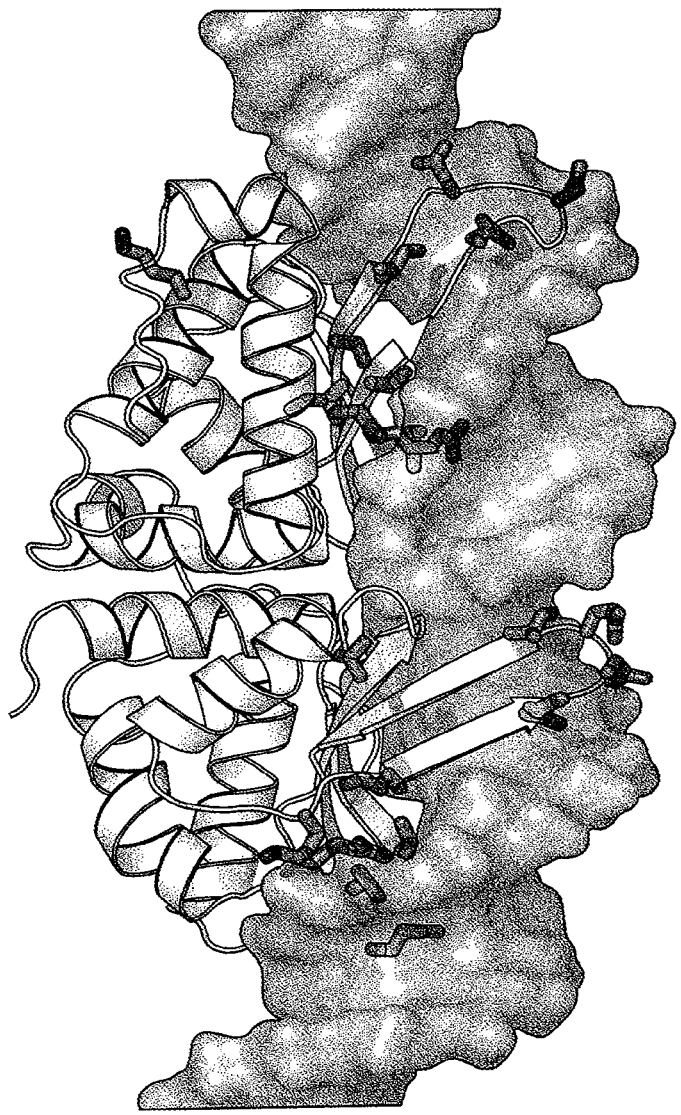
FIG. 20 is a protein model showing the distribution of amino-acid residues different between the BCL11A gene-targeting endonuclease and its parental LHE I-HjeMI. Substituted residues of the BCL11A gene-targeting endonuclease are mapped on the crystal structure of I-HjeMI bound to its target site (PDB ID: 3UVF). D161 is deleted in the variant endonuclease.
Figure 21:
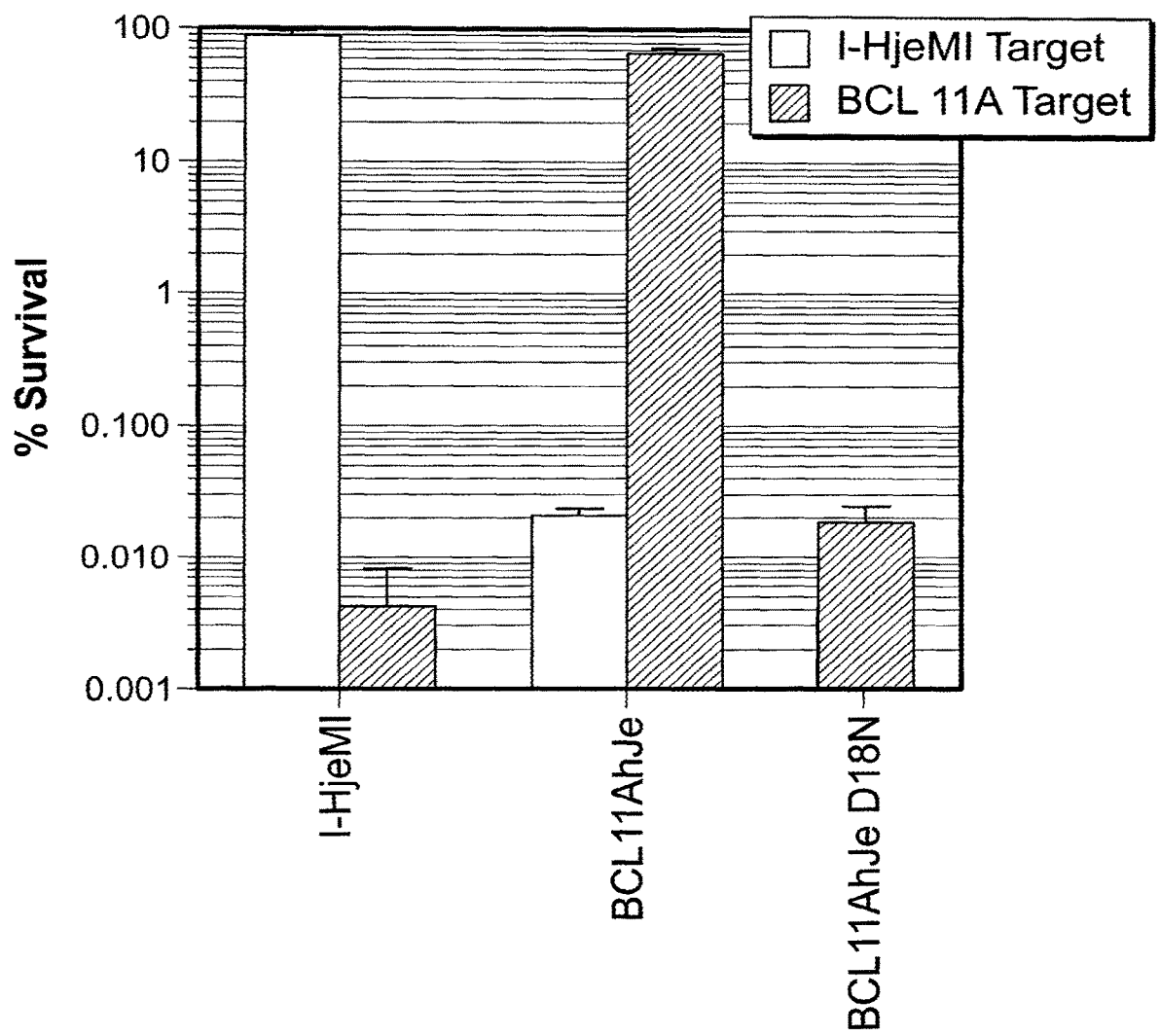
FIG. 21 is a bar graph showing the activity of a BCL11A gene-targeting endonuclease in a two-plasmid cleavage assay.

To redesign I-HjeMI variants that recognized the (−) and (+) half sites of the BCL11A gene target, 4 and 2 rounds of site-directed saturation mutagenesis were carried out, respectively (FIG. 13). A pool of variant nucleases targeting the former half-site was subjected to an additional (fifth) round of mutagenesis on the surface opposite to the protein-DNA interface, followed by 3 rounds of IVC (Table 2).

TABLE 2

Amino-acid Positions Subjected to Saturation Mutagenesis in IVC

| Round | Target Site* | Sequence Identifier | Amino Acid Residues |
|---|---|---|---|
| 1 | TTGAGGAG<u>A</u>T<u>G</u>TCTCTGTTAAT | SEQ ID NO: 55 | R61, R63, N64, E65, I66, M68, S70 |
| 2 | TTGAGG<u>T</u>G<u>A</u>T<u>G</u>TCTCTGTTAAT | SEQ ID NO: 56 | Y20, S22, E33, G35, E37, S59, R61, R70, R72 |
| 3 | TTGA<u>A</u>G<u>T</u>G<u>A</u>T<u>G</u>TCTCTGTTAAT | SEQ ID NO: 57 | Y20, S22, T24, T31, E33, G35, R72, R74 |
| 4 | T<u>CC</u>A<u>A</u>G<u>T</u>G<u>A</u>T<u>G</u>TCTCTGTTAAT | SEQ ID NO: 58 | Y20, S22, T24, K26, G27, K28, T31, E33 |
| 5 | T<u>CC</u>A<u>A</u>G<u>T</u>G<u>A</u>T<u>G</u>TCTCTGTTAAT | SEQ ID NO: 59 | S109, N110, A121, S123, N124, N135, S137 |
| 1 | TTGAGGAGGTTTCT<u>G</u>TGTTAAT | SEQ ID NO: 60 | S154, S168, D170, I193, L195, R202, K204 |
| 2 | TTGAGGAGGTTTCTC<u>GGTGGTG</u> | SEQ ID NO: 61 | S154, L158, N159, D162, D163, I166, I168, K204, T206 |

*Underlined nucleotides differ from those in the target site for the parental LHE I-HjeMI.

DNA fragments that encoded the N-terminal and the C-terminal half-domains of I-HjeMI variant endonucleases responsible for the (−) and (+) half sites of the BCL11A gene target were assembled, and a pool of nucleases that cleaved the full BCL11A gene target site were selected through 3 rounds of IVC (FIG. 13).

Table 3 presents exemplary BCL11a target sequences, which comprise DNA sequence modules for which pools of highly active endonuclease variants (based upon homing endonucleases I-CpaMI and I-OnuI) have been isolated and their sequences determined.

TABLE 3

Base Homing Endonuclease I-CpaMI

| f 683/2508<br>chr2: 60,542,847-<br>60,542,868<br>Disrupts Bcl 11a-X<br>and XL forms | ATGGGATTCATATTGCAGACAA | SEQ ID NO: 25 |

Base Homing Endonuclease I-OnuI

| r 1588/2508<br>chr2: 60,542,630-<br>60,542,651<br>Disrupts Bcl 11a-X<br>and XL forms | AGCCATTGGATTCAACCGCAGC | SEQ ID NO: 26 |
| f 525/2508<br>chr2: 60,543,005-<br>60,543,026<br>Disrupts all Bcl 11a forms | caaaCAgccATTCAcCagTgcA | SEQ ID NO: 27 |

Example 2

Figure 12:
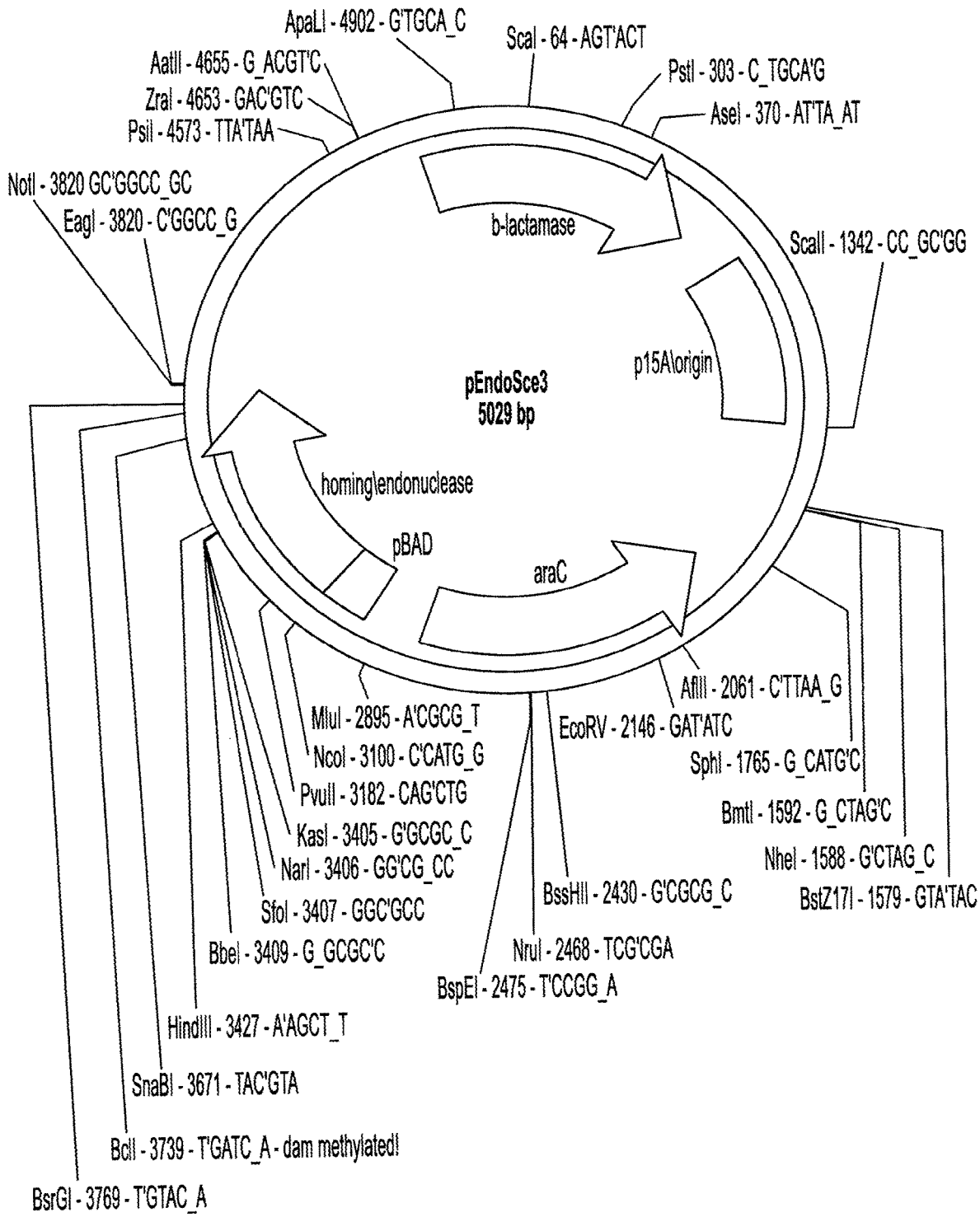
FIG. 12 is a restriction map for the plasmid pEndo (Doyon et al., *J. Am. Chem. Soc.* 128(7):2477-2484 (2006).
Figure 31:
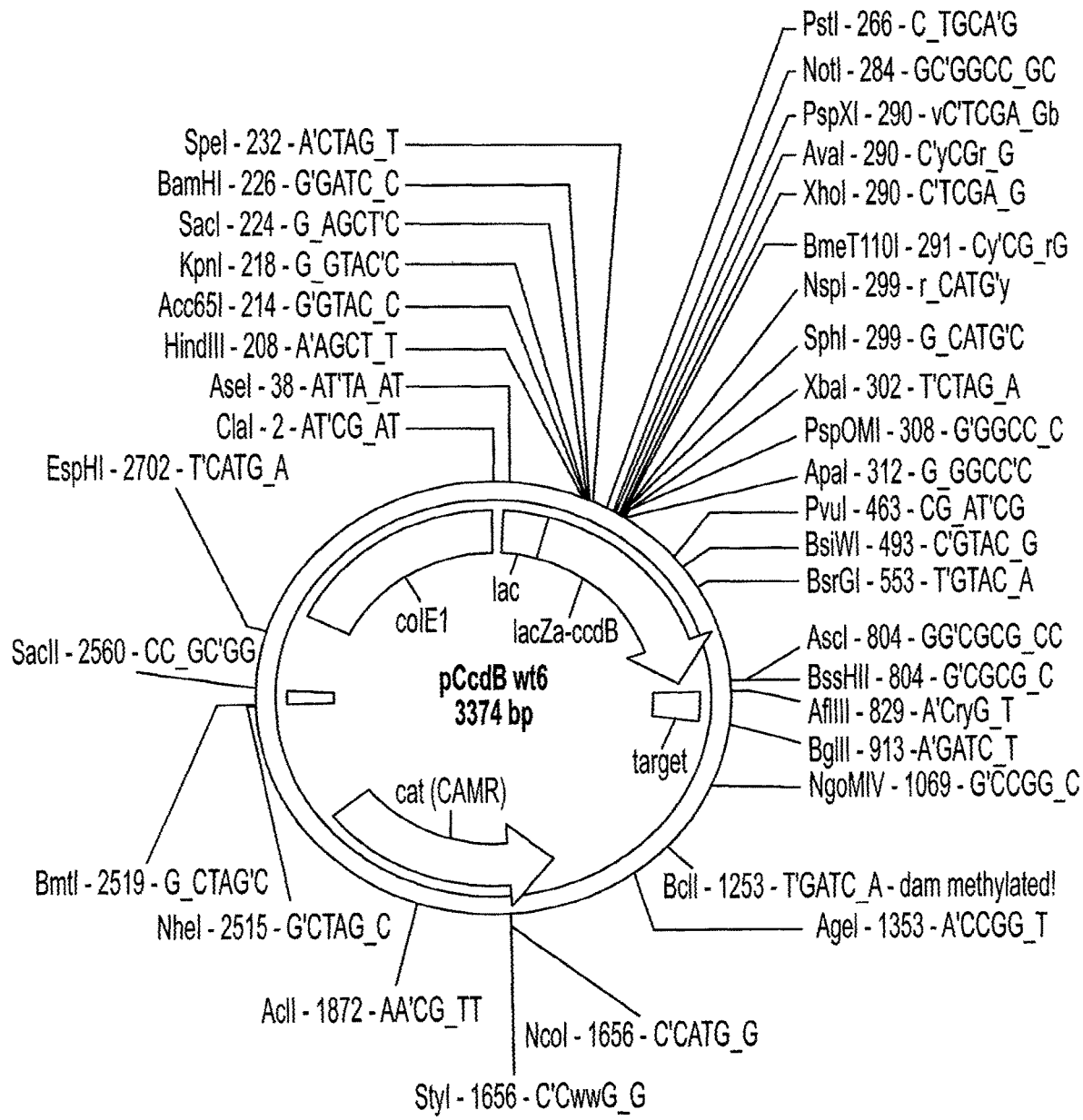
FIG. 31 is a restriction map for the plasmid pCcdB wt6 (Doyon et al., *J. Am. Chem. Soc.* 128(7):2477-2484 (2006).
Figure 34:
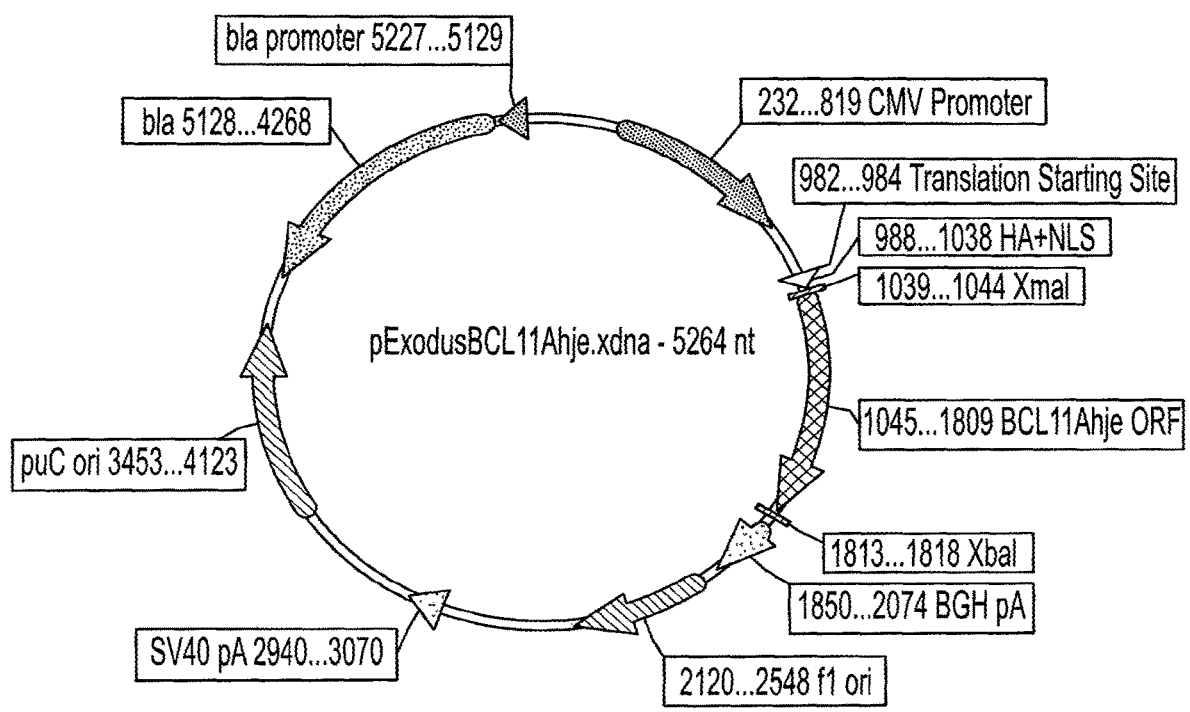
FIG. 34 is a restriction map for the plasmid pExodusBCL11Ahje.
Figure 35:
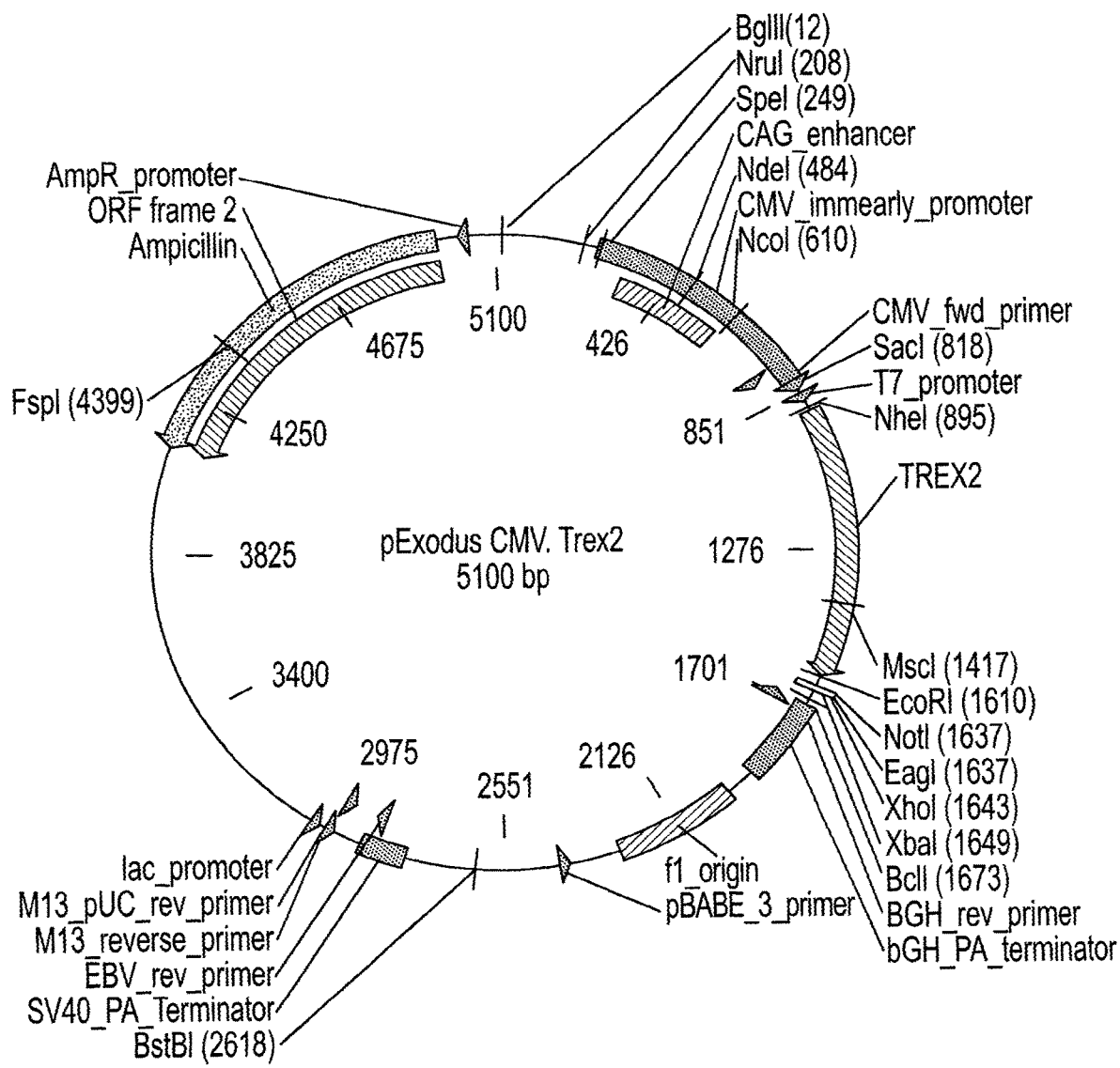
FIG. 35 is a restriction map for the plasmid pExodus CMV.Trex2.

Optimization of Activity of BCL11A Gene-Targeting I-HjeMI Variants Using Two Plasmid Gene Elimination Cleavage Assay in Bacteria The activity of I-HjeMI variants obtained in selection using IVC display selections (disclosed in Example 1, above) was optimized using a two-plasmid selection system in bacterial cells according to the methodology of Doyon et al., *J. Am. Chem. Soc.* 128(7):2477-2484 (2006). The ORF of the endonuclease genes was inserted between NcoI and NotI sites of the pENDO (FIG. 12, Doyon et al., *J. Am. Chem. Soc.* 128(7):2477-2484 (2006))expression plasmid. NovaXGF (EMD Millipore (Novagen)) competent cells harboring the pCcdB reporter plasmid (FIG. 31, Doyon et al., *J. Am. Chem. Soc.* 128(7):2477-2484 (2006); Takeuchi et al., *Nucl. Acids Res.* 37(3):877-890 (2009); and Takeuchi et al., *Proc. Natl. Acad. Sci. U.S.A.* 10.1073/pnas.1107719108 (2011)) containing 4 copies of the BCL11A gene target were transformed with a pool of the pEndo plasmid encoding I-HjeMI variants. The transformants were grown in 2×YT medium (16 g/L tryptone, 10 g/L yeast extract, and 5 g/L NaCl) at 37° C. for 30 min and then diluted 10-fold with 2×YT medium supplemented with 100 µg/mL carbenicillin and 0.02% L-arabinose (in order to preinduce expression of I-HjeMI variants). After the culture was grown at 30° C. for 15 hours, the cells were harvested, resuspended in sterile water and spread on both nonselective (1×M9 salt, 1% glycerol, 0.8% tryptone, 1 mM MgSO$_4$, 1 mM CaCl$_2$, 2 µg/mL thiamine, and 100 µg/mL carbenicillin) and selective plates (i.e. nonselective plates supplemented with 0.02% L-arabinose and 0.4 mM IPTG to induce expression of the toxic CcdB protein). After incubation at 30° C. for 30-40 hours, the pEndo plasmid was extracted from the surviving colonies on the selective plates.

The ORFs encoding active I-HjeMI variants were amplified via error-prone PCR using the Gene Morph II Random Mutagenesis Kit (Agilent Technologies, Santa Clara, Calif.). After digestion with NcoI, NotI, and DpnI, the resulting fragments were recloned into the pEndo vector. The plasmid was subjected to 2 rounds of selection under the conditions where variant endonucleases were expressed at 30° C. for 4 hours before plating. The N-terminal half and C-terminal half domains of the selected genes were shuffled using overlapping PCR, and again cloned into the pEndo vector. Transformed cells carrying both the pEndo plasmid and the pCcdB reporter were grown in 2×YT medium containing 0.02% L-arabonise at 37° C. for an hour and then spread on selective plates at 37° C. for 16-20 hours. After 2 rounds of selection at the same level of stringency, the pEndo plasmid was extracted from surviving colonies on the selective plates, and ORFs of the variant genes carried on the plasmid were sequenced.

Example 3

Activity of BCL11A Gene-Targeting Endonucleases Tested in a Two Plasmid Cleavage Assay Activity of an exemplary BCL11A gene-targeting endonuclease (BCL11Ahje; FIG. 17, SEQ ID NO: 31), its catalytically inactive variant (BCL11Ahje D18N), and its parental LHE I-HjeMI (FIG. 14, SEQ ID NO: 28) was measured in bacterial cells that harbor the pCcdB reporter plasmid (Doyon et al., J. Am. Chem. Soc. 128(7):2477-2484 (2006)) containing 4 copies of either the target site for I-HjeMI (I-HjeMI target) or the BCL gene target (TCCAAGTGAT GTCTCGGTGGTG (SEQ ID NO: 39; underlined nucleotides differ from those in the target site for the parental LHE I-HjeMI). The pCcdB reporter plasmid encodes "control of cell death B" ("ccdB", a toxic protein in bacteria, which is inducible by an addition of IPTG). Cleavage of the target sites in the reporter plasmid leads to RecBCD-mediated degradation of the reporter plasmid and corresponding cell survival on the selective medium containing IPTG. The survival rate was determined by dividing the number of colonies on the selective plates by that on the nonselective plates. Error bars refer ±S.D. of 3 independent experiments.

Example 4

Detection of Targeted Mutagenesis at the Endogenous Human BCL11A Gene

Figure 30:
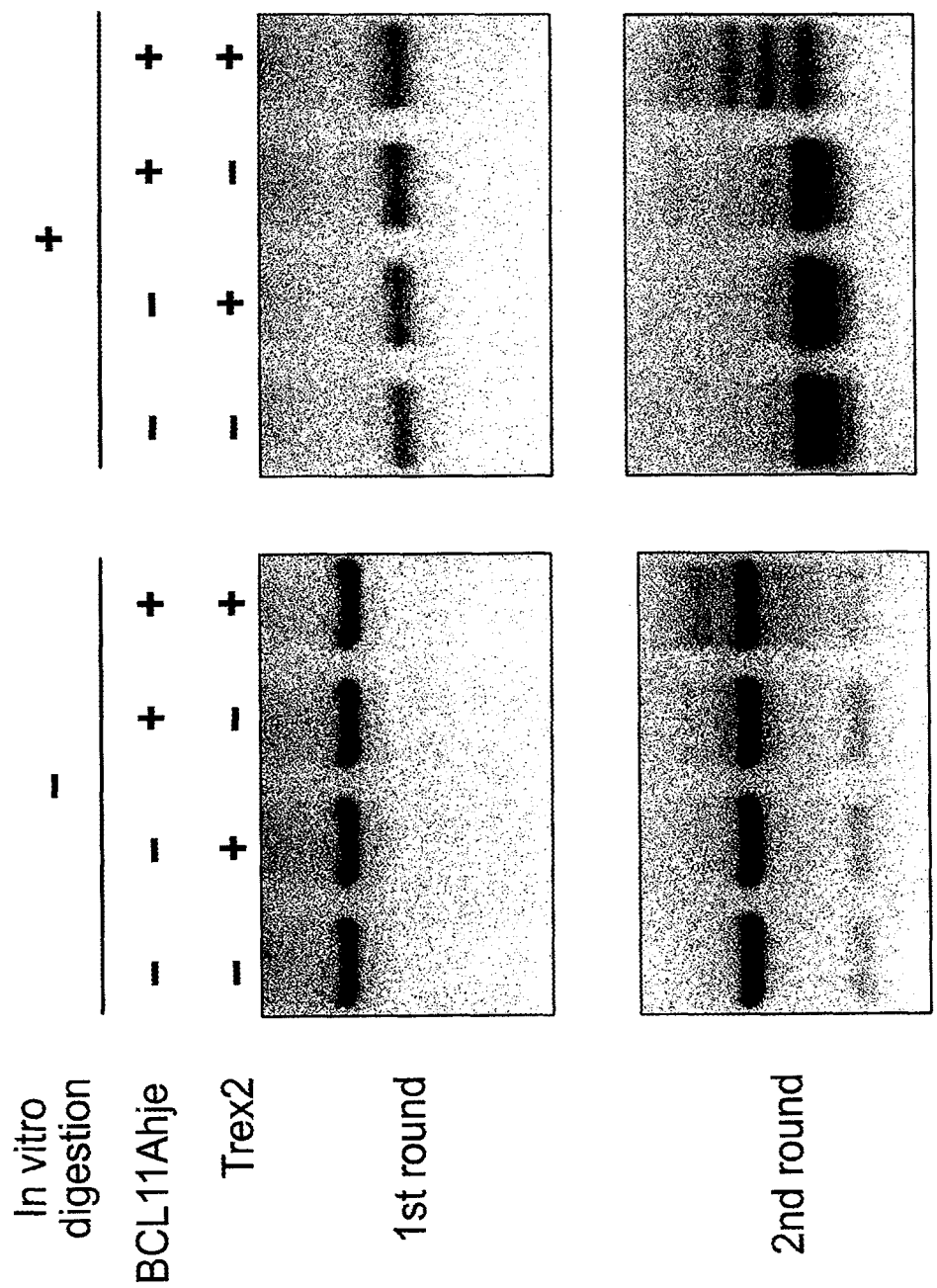
FIG. 30 is an agarose gel showing the detection of targeted mutagenesis at the endogenous human BCL11A gene as described in Example 4.

HEK 293T cells (1.6×10$^5$) were seeded 24 hours prior to transfection in 12-well plates, and transfected with 0.5 ug each of expression plasmids for the BCL11A gene targeting nuclease and TREX2. At 48 hours post transfection, transfected cells were lysed and genomic DNA was extracted using Quick-gDNA MiniPrep kit (Zymo Research). Approximately 500-bp fragment spanning the BCL11A gene target was PCR-amplified from 50 ng of the extracted genomes using a pair of the following primers: Bcl11A_up1, 5'-GCT GGA ATG GTT GCA GTA AC-3' (SEQ ID NO: 66); Bcl11A_down1, 5'-CAA ACA GCC ATT CAC CAG TG-3' (SEQ ID NO: 67). The PCR amplicon was incubated in 1×NEB buffer 4 plus 1×BSA (New England Biolabs) with or without 0.5 uM of the BCL11A gene targeting nuclease that was purified from E. coli overexpressing the recombinant protein at 37° C. for 2 hours. The reaction was terminated by adding 5× Stop solution (50 mM Tris-HCl (pH7.5), 5 mM EDTA, 0.5% SDS, 25% glycerol, 0.1 orange G and 0.5 mg/mL proteinase K). After incubation at room temperature for 15 minutes, a half of each sample was separated on a 1.6% agarose gel containing ethidium bromide in TAE (upper panels). The rest of each sample was purified using DNA Clean & Concentrator-5 kit (Zymo Research), and used as a template in the second round of PCR with a pair of the following primers: Bcl11A_up2, 5'-CTG CCA GCT CTC TAA GTC TCC-3' (SEQ ID NO: 68); Bcl11A_down2, 5'-TGC AAC ACG CAC AGA ACA CT-3' (SEQ ID NO: 69). The PCR product was again digested with the BCL11A gene targeting nuclease under the conditions described above, and analyzed on a 1.6% agarose gel (lower panels) (See FIG. 30).

Example 5

Selection of Fetal Hemoglobin Silencing Region Targeting Endonucleases Based on I-OnuI Using In Vitro Compartmentalization Exemplary homing endonuclease (HE) target sequences, which are evenly distributed throughout the 350 bp region (SEQ ID NO: 2) that includes the region of Bcl11a occupancy within the HbF silencing region in adult erythroid cells that is disrupted in the French HPFH deletion, are presented in Table 4. These target sequences comprise DNA sequence modules for which pools of highly active endonuclease variants have been isolated and sequenced.

TABLE 4

| Position | Chromosomal Location | Sequence | Sequence Identifier |
|---|---|---|---|
| Wild Type | N/A | TTTCCACTTATTCAACCTTTTA | SEQ ID NO: 5 |
| f 13/303 | chr11: 5,214,235-5,214,256 | TGTGGCCCTATTCTTGTGTTCA | SEQ ID NO: 6 |
| f 79/303 | chr11: 5,214,169-5,214,190 | CATTGTCACTTTCTTCCCTACT | SEQ ID NO: 7 |
| f 143/303 | chr11: 5,214,105-5,214,126 | TAAAATACATTTCTTCACTAAG | SEQ ID NO: 8 |
| f 124/303 | chr11: 5,214,089-5,214,110 | ACTAAGTGAGAATAATCTTTTA | SEQ ID NO: 9 |
| f 200/303 | chr11: 5,214,048-5,214,069 | GCCACCACCTTTCTTGAATTAT | SEQ ID NO: 10 |
| f 211/303 | chr11: 5,214,037-5,214,058 | TCTTGAATTATTCAATATCTTT | SEQ ID NO: 11 |
| f 274/303 | chr11: 5,213,974-5,213,995 | TTAAAGGTCATTCATGGCTCCT | SEQ ID NO: 12 |

Table 5 presents a region from −100 bp to 210 bp upstream of globin genes, which is identical for both Aγ- and Gγ-globin genes and which contains many of the non-deletion HPFH mutations. Gene editing resulting in these mutations leads to decreased repression, thus activation, of a gamma gene and results in increased HbF.

TABLE 5

| Sequence | Sequence Identifier |
|---|---|
| Wild-type | TGGGGGCCCCTTCCCCACACTATCTCAATGCAAATAT CTGTCTGAAACGGTCCCTGGCTAAACTCCACCCATGG GTTGGCCAGCCTTGCCTTGACCAATAGCCTTGACAA | SEQ ID NO: 16 |

TABLE 5-continued

| Sequence | | | Sequence Identifier |
|---|---|---|---|
| G-gamma-202 C→G | TGGGGGC<u>G</u>CCTTCCCCACACTATCTCAATGCAAATAT | CTGTCTGAAACGGTCCCTGGCTAAACTCCACCCATGG | SEQ ID NO: 17 |
| | GTTGGCCAGCCTTGCCTTGACCAATAGCCTTGACAA | | |
| G-gamma-175 T→C | TGGGGGCCCCTTCCCCACACTATCTCAATGCAAA<u>C</u>AT | CTGTCTGAAACGGTCCCTGGCTAAACTCCACCCATGG | SEQ ID NO: 18 |
| | GTTGGCCAGCCTTGCCTTGACCAATAGCCTTGACAA | | |
| G-gamma-114 C→T | TGGGGGCCCCTTCCCCACACTATCTCAATGCAAATAT | CTGTCTGAAACGGTCCCTGGCTAAACTCCACCCATGG | SEQ ID NO: 19 |
| | GTTGGCCAGCCTTGCCTTGAC<u>T</u>AATAGCCTTGACAA | | |
| A-gamma-196 C→T | TGGGGGCCCTTC<u>T</u>CCACACTATCTCAATGCAAATAT | CTGTCTGAAACGGTCCCTGGCTAAACTCCACCCATGG | SEQ ID NO: 20 |
| | GTTGGCCAGCCTTGCCTTGACCAATAGCCTTGACAA | | |
| A-gamma-175 T→C | TGGGGGCCCCTTCCCCACACTATCTCAATGCAAA<u>C</u>AT | CTGTCTGAAACGGTCCCTGGCTAAACTCCACCCATGG | SEQ ID NO: 21 |
| | GTTGGCCAGCCTTGCCTTGACCAATAGCCTTGACAA | | |
| A-gamma-117 G→A | TGGGGGCCCCTTCCCCACACTATCTCAATGCAAATAT | CTGTCTGAAACGGTCCCTGGCTAAACTCCACCCATGG | SEQ ID NO: 22 |
| | GTTGGCCAGCCTTGCCTT<u>A</u>ACCAATAGCCTTGACAA | | |
| A-gamma-114→-102 deleted (deleted bases in bold) | TGGGGGCCCCTTCCCCACACTATCTCAATGCAAATAT | CTGTCTGAAACGGTCCCTGGCTAAACTCCACCCATGG | SEQ ID NO: 23 |
| | GTTGGCCAGCCTTGCCTTGACCAATAGCCTTGACAA | | |

Table 6 presents amino acid positions within a parental LHE I-OnuI homing endonuclease (FIG. 22A, SEQ ID NO: 34) that were subjected to saturation mutagenesis in IVC (as described in Example 1, above) to create homing endonucleases that are targeted against a human fetal globin silencing region.

TABLE 6

Amino-acid Positions Subjected to Saturation Mutagenesis in IVC to Create Targeted Homing Endonucleases against a Human Fetal Globin Silencing Region

| Round | Target site* | Sequence Identifier | Amino-acid residues |
|---|---|---|---|
| 1 | TTTCCA<u>A</u>TTATTCAACCTTTA | SEQ ID NO: 40 | L26, G44, Q46, A70, S72, S78, K80 |
| 2 | TC<u>TTGA</u>ATTATTCAACCTTTTA | SEQ ID NO: 41 | L26, R28, R30, N32, S40, E42, G44, K80, T82 |
| 1 | TTTCCATTTATTCAA<u>TAT</u>TTA | SEQ ID NO: 42 | F182, N184, V199, S201, K225, K227, D236, V238 |
| 2 | TTTCCATTTATTCAA<u>TATCTTT</u> | SEQ ID NO: 43 | F182, N184, I186, S190, K191, Q197, V199, V238, T240 |

*Underlined nucleotides differ from those in the target site for the parental LHE I-OnuI.

Figure 23:
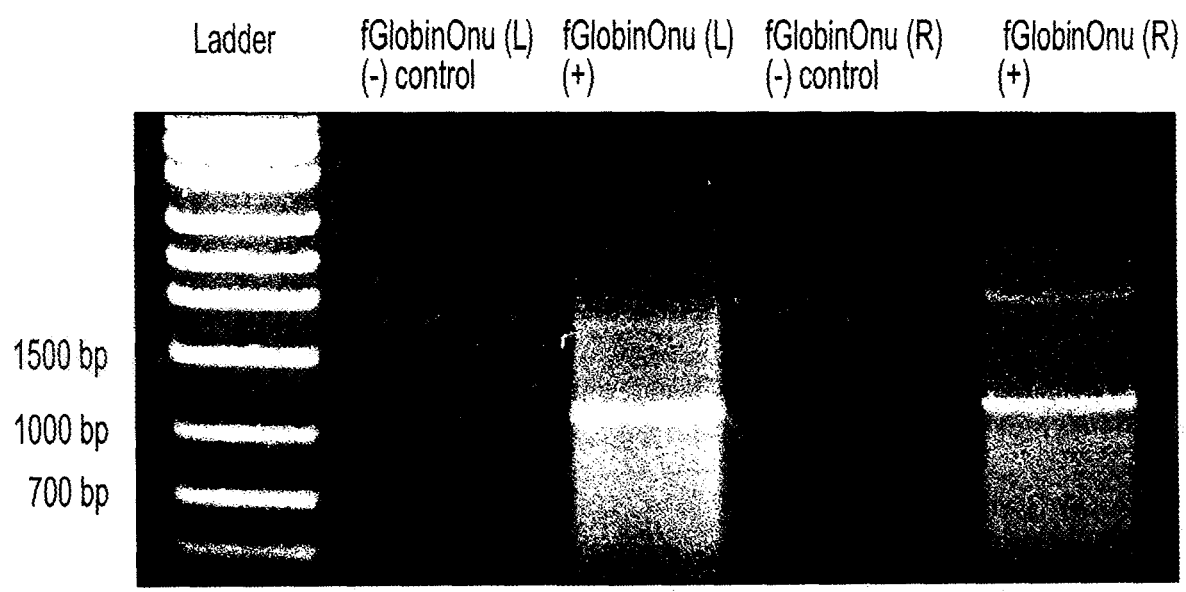
FIG. 23 is an agarose gel showing the activity of an I-OnuI homing endonuclease targeting the HbF silencing region.

FIG. 23 presents the results of a of a cleavage assay with 'half-targets' from a human fetal globin silencing region. The amplified bands contain both the cleaved half-sites (captured by ligation with complementary duplex oligonucleotides and corresponding overhanging ssDNA) and the sequences of the enzyme variants that are responsible for generation of cleaved DNA products. The final step upon completion of enrichment of the 'half-site' endonuclease libraries includes the assembly of DNA fragments that encode the N-terminal and C-terminal half domains of I-OnuI homing endonuclease, which are responsible for the left (L) and right (R) half sites of the gGlobin silencing region target. Active I-OnuI endonucleases are selected from a pool that cleaves the full-length human fetal globin silencing region target.

Example 6

MegaTALs Homing Endonucleases with N-terminal Fusions of TAL Anchors to Increase Specificity and Activity of a Gene-targeted Endonuclease N-terminal fusions of TAL anchors can be employed to increase the specificity and activity of a gene-targeted endonuclease, including one or more homing endonucleases such as one or more of the I-HjeMI, I-CpaMI, and I-OnuI homing endonucleases. MegaTALs are constructed using the Golden Gate assembly strategy described by Cermak et al., *Nucl. Acids Res.* 39:e82-e82 (2011), using an RVD plasmid library and destination vector (see, FIG. 24, SEQ ID NO: 35 and FIG. 25, SEQ ID NO: 36 for the nucleotide and amino acid sequences of MegaTAL:5.5 RVD+Y21-AniI).

Plasmids are modified to allow the assembly of TAL effector containing 1.5 to 10.5 TAL repeats and their corresponding RVDs ('Repeat Variable Diresidues,' which contact consecutive DNA bases in the 5' region of the target site and thereby define the cognate DNA sequence in that region). The pthX01 destination vector was modified to include a hemagglutinin (HA) tag immediately downstream of the NLS and to yield a TALEN scaffold that begins at residue 154 (relative to wild-type PthXo1 TAL effector) and ends 63 residues beyond the final 'half TAL repeat' sequence.

TAL effectors are built using the following RVDs to target each specific nucleotide: A-NI, C-HD, G-NN and T-NG. Following cloning of the TAL effector repeats into the destination vector, an individual protein linker ('Zn4'; VGGS) and the engineered homing endonuclease variants are cloned in place of the FokI nuclease catalytic domain, between engineered Xba-I and Sal-I restriction sites.

This is a 'model test case' MegaTAL (a fusion of a TAL effector at the N-terminal end of a single protein chain, fused via a flexible linker to the wild-type Y2 I-AniI homing endonuclease, which was originally described in Takeuchi et al., *Nucl. Acids Res.* 37(3): 877-890 (2009).

Example 7

A Cas9-Based Endonuclease System for Disrupting a Bcl11a-Regulated Fetal Hemoglobin (HbF) Silencing Region The recent mechanistic understanding of the clustered regularly interspaced short palindromic repeat (CRISPR) system that bacteria use for adaptive immunity has led to the development of a powerful tool that allows for genome editing of mammalian cells, which can be employed in the compositions and methods for the treatment of hemoglobinopathies that are disclosed herein: (a) to disrupt a Bcl11a coding region; (b) to disrupt a HbF silencing DNA regulatory element or pathway, such as a Bcl11a-regulated HbF silencing region; (c) to mutate one or more γ-globin gene promoter(s) to achieve increased expression of a γ-globin gene; (d) to mutate one or more δ-globin gene promoter(s) to achieve increased expression of a δ-globin gene; and/or (e) to correct one or more β-globin gene mutation(s). The bacterial CRISPR system is described in Jinek et al., *Science* 337:816-821 (2013); Cong et al., *Science* (Jan. 3, 2013) (Epub ahead of print); and Mali et al., *Science* (Jan. 3, 2013) (Epub ahead of print).

The Cas9 protein generates a double stranded break at a specific site the location of which is determined by an RNA-guide sequence. All guide RNAs contain the same scaffold sequence that binds Cas9, as well as a variable targeting sequence having the structure $G-N_{20}-GG$, which provides Cas9-RNA complex cleavage specificity. Co-expression of the Cas9 protein and a guide RNA results in the efficient cleavage and disruption at a sequence-specific location within the human genome, which sequence-specific cleavage is defined by the guide RNA sequence. Co-expression of Cas9 and guide RNAs that are specific to multiple targets leads to efficient deletion of the intervening region between target sites.

Thus, within certain aspects of the present disclosure, Cas9-meditated genome editing is employed: (1) to disrupt the Bcl11a binding site within the HbF silencing region, (2) to disrupt Bcl11a gene function, and (3) to delete the entire HbF silencing region. Target regions are identified and guide RNAs are designed and generated based on consideration of the optimal guide RNA target sequences. Exemplified herein are guide RNAs that target the Bcl11a binding region within the HbF silencing region as well as the single GATA-1 binding motif. These guide RNAs are used singly or in combination to achieve the targeted disruption of the HbF silencing region. Cas9 with guide RNAs to additional regions within the HbF silencing regions that correspond to Bcl11a peaks of occupancy are also used singly and in combination. Several pairs of guide RNAs flanking the Bcl11a binding site and GATA-1 motif, as well as the entire footprint, can also be co-expressed with Cas9 in order to generate deletions within the HbF silencing region.

The sequence of a human codon optimized Cas9 from Mali et al., *Science* (Jan. 3, 2013) is presented in FIG. 26, SEQ ID NO: 37. The generic sequence of a guide RNA (Mali et al.) is presented in FIG. 27, SEQ ID NO: 38, the key sequence elements of which are presented in Table 7. Exemplary Cas9 Guide RNAs sequences of target-specific binding to and cleavage of the human fetal hemoglobin (HbF) silencing region (FIG. 6, SEQ ID NO: 1 and FIG. 7, SEQ ID NO: 2) are presented in Table 8.

TABLE 7

Sequence Elements of a Generic Cas9 Guide RNA

| Description | Sequence Identifier | Nucleotide Sequence |
|---|---|---|
| U6 Promoter Sequence | SEQ ID NO: 44 | GGACGAAACACC |
| Generic Target-specific Sequence | SEQ ID NO: 45 | GNNNNNNNNNNNNNNNNNNNN |
| Guide RNA Scaffold Sequence | SEQ ID NO: 46 | GTTTTAGAGCTAGAAATAGC AAGTTAAAATAAGGCTAGTC CGTTATCAACTTGAAAAAGT GGCACCGAGTCGGTGCT |
| Poly T Tail | SEQ ID NO: 47 | NNNNTTTTT |

TABLE 8

Target-specific Sequences for Exemplary Cas9 Guide RNAs

| Designation | Description | Use | Sequence Identifier | Nucleotide Sequence |
|---|---|---|---|---|
| GGN20GG-B | Targets the GATA-1 recognition motif | Used singly, with #C to delete the putative Bcl 11a and GATA-1 motifs jointly, or with #E, #F or #G to delete the entire Bcl 11a ChIP peak and surrounding sequences | SEQ ID NO: 48 | GCCATTTCTA TTATCAGACT TGG |
| GGN20GG-C | Targets the putative Bcl 11a recognition motif | Used singly, with #B to delete the putative Bcl 11a and GATA-1 motifs jointly | SEQ ID NO: 49 | GCTGGGCTTC TGTTGCAGTA GGG |
| GGN20GG-D | Targets immediately adjacent to the | Used singly, with #B to delete the putative Bcl 11a and | SEQ ID NO: 50 | GAAAATGGG AGACAAATA GCTGG |

TABLE 8-continued

Target-specific Sequences for Exemplary Cas9 Guide RNAs

| Designation | Description | Use | Sequence Identifier | Nucleotide Sequence |
|---|---|---|---|---|
| | putative Bcl 11a recognition motif | GATA-1 motifs jointly | | |
| GGN20GG-E | Targets downstream of the Bcl 11a binding peak | Used with #B and/or #H to delete the entire Bcl 11a ChIP peak and surrounding sequences | SEQ ID NO: 51 | GAATAATTCA AGAAAGGTG GTGG |
| GGN20GG-F | Targets downstream of the Bcl 11a binding peak | Used with #B and/or #H to delete the entire Bcl 11a ChIP peak and surrounding sequences | SEQ ID NO: 52 | GATATTGAAT AATTCAAGA AAGG |
| GGN20GG-G | Targets downstream of the Bcl 11a binding peak | Used with #B and/or #H to delete the entire Bcl 11a ChIP peak and surrounding sequences | SEQ ID NO: 53 | GCCTGAGATT CTGATCACAA GGG |
| GGN20GG-H | Targets upstream of the Bcl 11a binding peak | Used with #E, #F or #G to delete the entire Bcl 11a ChIP peak and surrounding sequences | SEQ ID NO: 54 | GGTAAATTCT TAAGGCCATG AGG |

Example 8

Vector Systems for Expressing Endonucleases

For NSG, sickle cell and thalassemia mouse models, human CD34 cells or mouse bone marrow nucleated cells are transduced along with a fluorescent marker allowing flow cytometry-based enrichment of cells prior to transplantation. Suitable transduction methods include the following:

Aav6 Vectors.

AAV6-serotype recombinant AAV vectors provide a 4.5 kb payload, sufficient to deliver a promoter-HE-exonuclease or promoter-TAL-HE fusion-exonuclease cassettes in addition to a small recombination template. Alternatively they can carry Cas9 and a guide RNA. In addition, we have preliminary data that show AAV6 provides the most efficient transduction of human CD34+ umbilical cord blood cells of all known AAV capsids, and is able to mediate significant levels of transient gene expression in HSC.

Modified Adenovirus Vectors.

Adenoviral vectors with hybrid capsids are capable of efficiently transducing many types of hematopoietic cells including CD34+ cells. Improved transduction with the chimeric vector using the serotype 35 fiber (Ad5-F35) was demonstrated by Dr. Rawlings (SCH) and more recent data suggest that the serotype 11 fiber (Ad5-F11) may be even more efficient in hematopoietic cells. Helper-dependent adenoviral vectors offer up to a 30 kb payload, along with transient gene expression in HSC, and can be used to deliver multiple HE/exonuclease cassettes, HE-TAL fusions, as well as very large recombination templates or a Cas9 expression cassette and multiple guide RNAs.

Integration-Deficient Lentiviral and Foamyviral Vectors (IDLV and IDFV).

These vectors provide 6 kb (IDLV) to 9 kb (IDFV) payloads, and have well documented capabilities to transduce human HSCs. Both IDLV and IDFV vectors can be used for gene knockout and recombination-based gene editing in HSC. Drs. Rawlings (SCH) and Kiem (FHCRC) have generated and evaluated a series of IDLV with alternative promoter GFP cassettes and have determined constructs that provide efficient and high level expression in CD34+ HSC.

Direct Nucleofection of Plasmid and mRNA.

Conditions for efficient transduction of N-MEL and CD34 cells have been defined using the Amaxa nucleofection system. Benefits include the lack of integration, and the ability to transduce multiple expression plasmids or RNA species simultaneously.

In parallel, sorted and un-sorted cells will be transplanted into separate mice. While the later transplants may contain low numbers of modified cells, human studies of post-transplant chimeras suggest that these cells will have a selective survival advantage and be enriched in the periphery. Regardless, single reticulocyte RNA and F-Cell analysis will allow assessment of gene disruption in cells even if present in low abundance.

Second level assessments will focus on the pluripotency of transduced CD34+ cells and erythropoiesis. Assays will include culturing to assess long-term proliferative potential, analysis of myeloid and erythroid colonies for clonal analysis and transplant into NOD scid gamma (NSG) mice followed by assessment of multi-lineage engraftment of primary and secondary recipients.

Typically stem cells are infused via tail vein injection after total body irradiation (275 rads for NSG mice or 1000 rads for C57 mice). Though efficient, this is effective, for most studies we will inject stem cells directly into the mouse femur as 50 fold fewer cells are required, ideal or assaying a potentially limited number of flow cytometry sorted and/or modified cells. After anesthesia and local analgesia are provided and anatomic landmarks defined, 0.5-1 million cells are directly injected into the femurs marrow space.

Example 9

Characterization of Homing and Cas9 Endonucleases for Efficient Gene Targeting

For clinical impact efficient gene targeting is demonstrated by assessing levels of globin gene expression in individual targeted cells and in populations of cells, the effect of targeting on erythropoiesis and on stem cell function, and impact hematologic parameters and organ function in model organisms.

Transductions are followed by single cell and bulk population assessments of gene targeting efficiency and expression of all β-like genes at the RNA and protein levels. Alterations in factor binding and chromatin structure are assessed, as cell morphology and the extent of ineffective erythropoiesis and apoptosis. Candidate endonucleases that score well in initial screens are further assessed for effects on HSC pluripotency as well as the ability to ameliorate disease specific phenotypes in vitro and in vivo.

Initial screening of endonuclease candidates and delivery systems is performed in a mouse erythroleukemia cell line containing a single intact human chromosome 11 (N-MEL) and clinical grade CD34+ normal human HSCs with endpoints of assessing targeted mutation efficiency and globin gene expression. Both cell types can be induced to differentiate along an erythroid path during which expression of β-like genes is highly induced with a low γ-globin/γ-+β-globin RNA ratio. Using a HbF specific antibody, the percent of "F-cells" can be quantified. These low ratios are ideal as the systems are sensitive for detecting and quantifying even small increases in γ-globin mRNA as well as HbF expression at the single cell and population level.

N-MEL cells are a derivative of murine erythroleukemia cells that contain a single intact human chromosome 11 that contains the β-globin locus. This erythroid cell line normally expresses low levels of mouse and human β-like globin genes, but can be induced to differentiate at which time globin expression is greatly increased.

N-MEL cells are efficiently transduced using the Amaxa nucleofection system. Using 2 μg of plasmid DNA, Kit "L" and program A20 25% of cells are transduced. Infection at multiplicity of infection (MOI) of 20 with a RSCS-MCS-PG-WZ based lentiviral vector containing a homing endonuclease designed to disrupt the Bcl11a gene yields approximately 40% of N-MEL cells being transduced.

The efficiency of targeted disruption is assayed using the Cel-1 assay. The target region is amplified by PCR, heat-denatured, re-annealed and exposed to the enzyme Cel-1 that efficiently cleaves bubbles from mismatched regions as small as one base pair. If the targeted region has been mutated in any way, heteroduplexes of wild type and mutant strands are cleaved and detected by gel electrophoresis. This assay can be used on bulk populations of cells to estimate the efficiency of mutation, or on flow cytometry sorted individual cells in which case analysis of multiple cells provides an accurate assessment of mutation frequency.

Using routine quantitative Taqman RT-PCR (qRT-PCR) assays for RNA from a bulk population of cells, β-globin expression is induced 11-fold with differentiation and with a γ-globin/γ-+β-globin ratio of 0.1%. After infection with a Bcl11a knockdown vector a 30-fold increase in this ratio can be obtained, thus demonstrating that this cell culture system provides an accurate readout of disruption of the BCl11a mediated HbF silencing pathway.

Due to concerns that altering Bcl11a pathways may lead to a relative increase in γ-globin RNA but a decrease in globin gene expression, flow cytometry can be used to sort 1000 cell pools of cells that are lysed and the above qRT-PCR assays can be performed. Because RNA is directly compared from the same number of cells, any diminution in the amount of globin RNA is reflected by an increase in the Ct, providing a direct measure of both the level of β- and γ-expression, as well as the ratio of γ-globin/γ-+β-globin.

To determine the percent of cells that show an altered γ-globin/γ-+β-globin ratio after manipulation and to determine the range of change in expression observed, single cell assays are performed. Flow cytometry sorted individual cells are subjected to routine RT-PCR of γ- and β-globin RNA simultaneously for several cycles and once adequate material is present to allow for accurate splitting of the sample, γ- and β-globin are assessed by qRT-PCR as above.

Ultimately it is levels of HbF protein, not RNA that are therapeutic, thus single cell and bulk cell HbF assays are performed. Bulk populations of cells are assayed using HPLC after cell lysis and elution on a hemoglobin-dedicated column and the ratios of HbF to HbA and HbA2 are determined. The number of cells expressing HbF are compared pre- and post-transduction using gluteraldehyde fixing cells, permeabilizing with detergent and adding an HbF specific antibody followed by quantitation by flow cytometry.

Effects of mutations are assessed in modified cloned cells after isolation of single cells by flow cytometry. The above assays are performed. In addition, to show that targeted mutations disrupt binding of the Bcl11a repressive complex, cells are fixed in formaldehyde, chromatin isolated and sheared by sonication. Chromatin immune-precipitation (ChIP) is performed using commercially available antibodies to Bcl11a, GATA-1 and HDAC-1. Binding of these proteins to a target region in N-MEL cells, as well as erythroid-differentiated CD34 cells is described below. A lack of binding is assessed after targeted disruption.

Example 10

Clinical Grade CD34+ Hematopoietic Stem Cells

CD34+ cells from normal human donors are adhered to culture dishes with fibronectin peptide CH-296 and infected at an MOI of 20 twice, 8 hours apart, in media containing G-CSF, SCF, IL-3, IL-6, FLT-3, and TPO, with RSCS-MCS-PG-WZ based lentiviral vectors described above. This results in ~80% of cells being infected. Transduced cells are differentiated to erythroid cells using the protocol of Douy. Giarratana et al., *Nat. Biotechnol.* 23(1):69-74 (2005). The qRT-PCR assays above reveal a γ-globin/γ-+β-globin ratio of 4%. This low ratio allows for the sensitive detection of increases that are secondary to genome editing.

To assess alterations in differentiation state, flow cytometry using multiple cell surface markers including CD34, CD71, and glycophorin are performed, as well as assessment of cell growth and morphology of cytospins after Wright-Giemsa staining. Disruption efficiency is assessed by Cel-1 assays on bulk populations and single cells as above. Additional assessment of globin gene expression and HbF is performed as above using qRT-PCR on 1000 cell pools and individual cells as well as HPLC and F-cell assays. ChIP is employed to assess binding of Bcl11a, GATA-1, and HDAC-1 to the target region.

To assess clinical effectiveness in human cells CD34+ human, HSCs from hemoglobinopathy patients are transduced and cultured using the same methods. In addition to the routine analysis for normal cells, additional disease-specific assessments are performed. Cultured thalassemic cells show minimal expansion, a lack of hemoglobinization, evidence of ineffective erythropoiesis, and increased apoptosis compared to normal cells. This allows for quantitative assessments of improvements in expression and erythropoiesis post-targeting. Similarly, the degree of sickling of erythroid progeny of CD34 cells under hypoxic conditions is assessed. These transduced CD34+ cells from hemogobinopathy patients are transplanted into NSG mice, after which several features of abnormal erythropoiesis are recapitulated, allowing assessment of the effect of targeted mutagenesis.

Clinical effectiveness is assessed in vivo in mouse models of hemoglobinopathies. Knockout of murine Bcl11a leads to a dramatic dose-dependent increase in γ-globin in mice containing a human β-globin locus on a transgene and ameliorates the sickle phenotype in humanized mouse models. While both systems allow the analysis of globin gene expression, the sickle mice allow for the assessment of the improvement of phenotype in these mice with special attention to the hematologic parameters especially the hematocrit, liver and lung pathology, renal function and spleen size. This can be correlated to the number of HbF containing cells, the HbF/S ratio and expression patterns in single cell assays similar to the above.

For RNA analysis total blood is used as it contains sufficient RNA-containing reticulocytes for analysis. For single cell analyses blood is stained with thiazole orange and RNA containing cells with the forward and side scatter profiles of red cells are collected. The erythrocyte lifespan is significantly reduced in the sickle cell mice and improvement in lifespan is assessed after intra-peritoneal injection of NHS-biotin with labels 100% of RBC. At time points, a microliter of blood is stained with strep-avidin FITC and the remaining percent of labeled RBC is assessed by flow cytometry. This is done with the mice from our BERK sickle cell mice. Pászty et al., *Science* 278(5339):876-878 (1997). In addition, the γ-globin/γ-+β-globin ratio is assessed in mice containing the A25 and A85 human β-globin YACs. Porcu et al., *Blood* 90(11):4602-4609 (1997).

Two thalassemic models are assessed, the Th-3 mouse heterozygotes (Yang et al., Proc. Natl. Acad. Sci. U.S.A. 92(25):11608-11612 (1995)) and mice heterozygous for a deletion of the LCR (Bender et al., *Mol Cell*. 5(2):387-393 (2000)). In each case, the focus of analysis for thalassemic mice will be hematocrit, assessment of ineffective erythropoiesis, spleen size, iron overload and organ morphology.

SEQUENCE LISTING

```
<160> NUMBER OF SEQ ID NOS: 69

<210> SEQ ID NO 1
<211> LENGTH: 3603
<212> TYPE: DNA
<213> ORGANISM: Homo sapiens

<400> SEQUENCE: 1
ccagtgagca ggttggttta agataagcag ggtttcatta gtttgtgaga atgaaaaatg      60
aaccttcatt ccactattcc cttaacttgc cctgagattg gctgttctgt catgtgtgtc     120
ttgactcaga aaccctgttc tcctctacat atctccccac cgcatctctt tcagcagttg     180
tttctaaaaa tatcctccta gtttcatttt tgcagaagtg tttaggcta atatagtgga      240 atgtatctta gagtttaact tatttgtttc tgtcactta tactaagaaa acttatctaa      300
aagcagatgt tttaacaagt tgactcaata taaagttctt ctttgcctct agagattttt     360
gtctccaagg gaattttgag aggttggaat ggacaaatct attgctgcag tttaaacttg     420
cttgcttcct ccttcttttg gtaaattctt cctataataa aactctaatt ttttattata     480
ttgaaataaa tatccattaa aagaatattt aaaaaatgaa tagtgtttat ttaccagtta     540
ttgaaatagg ttctggaaac atgaatttta aggttaacat tttaatgaca gataaaatca     600
aatattatat acaaatattt tgaatgttta aaattatggt atgactaaag aaagaatgca     660
aagtgaaaag tagatttacc atattcagcc agattaaatt taacgaagtt cctgggaata     720
tgctagtaca gaacattttt acagatgtgt tcttaaaaaa aaatgtggaa ttagacccag     780
gaatgaagat cccagtagtt tttcactctt ttctgaattc aaataatgcc acaatggcag     840
acaaatacac acccatgagc atatccaaaa ggaaggattg aaggaaagag gaggaagaaa     900
tggagaaagg aaggaaggaa gaggggaaga gagaggatgg aagggatgga ggagaagaag     960
gaaaaataaa taatggagag gagaggagaa aaaaggaggg gagaggagag gagaagggat    1020
agggaagaga aagagaaagg gaagggaaga gaggaaagaa gagaagagga gagaaaagaa    1080
acgaagagag gggaagggaa ggaaaaaaaa gaggaaaaaa gagacaagag aagagataag    1140
actgacagtt caaattttgg tggtgatatg gatcaataga aactcaaact ctgttggtga    1200
cactgtacaa tagtataacc cctttggaaa acctttaata gtatccacaa atgctggatg    1260
cttgataagt ctattaccta gcaattacat ttttagatat tcagaaacac atgcatgtgt    1320
gtatccaaag acatgtatag aaatgcttat gacagcaata atcataaaaa cctcaaaccg    1380
gtagccactt aaatgcttac caacagtaga attgataaat tacggtatag tcaaagaata    1440
gaatattaca cagaaatgaa aagaatcaac tactgcttaa cacgtagcga tacaaatgca    1500
```

-continued

```
ttttacagca tttggttgat taaaagtaac cagaggtgag ttcaaactat atgactttat      1560
ttgtatatag aaagatggat gatgtgcctg agattctgat cacaagggga aatgttataa      1620
aatagggtag agaggagcca tgaatgacct ttaaactttg ttacaagtta tttttctgta      1680
acctggaagc caacgaaaga tattgaataa ttcaagaaag gtggtggcat ggtttgattt      1740
gtgtctttaa aagattattc tcacttagtg aagaaatgta ttttagaagt agagaaaatg      1800
ggagacaaat agctgggctt ctgttgcagt agggaagaaa gtgacaatgc catttctatt      1860
atcagacttg gaccatgacg gtgatgtcag tcgtgaacac aagaataggg ccacatttgt      1920
gagtttagtg gtacgataaa atcagaaata cagtcttgga tacattgtat tgtatgcact      1980
cttgtaaaat gcaaaaagat gtacttagat atgtggatct ggagctcaga aagaatacaa      2040
ccaggtcaag aatacagaat ggaacagaac atacaagaac agatcataat gtgctgtgtg      2100
aatcactacc actacctgtt aaaaatgaca gatgatgtac ttcatcaata tctccttaaa      2160
atcttagaat gtgtttgtga gggaggaatt atgtttccaa ttcatatata agaaaattga      2220
ttctaaaaaa aatgttaggt aaattcttaa ggccatgagg actgttattt gatctttgtc      2280
tgttaattcc aaagacttgg cttttcactt taattctgtt ctacctgaaa tgattttaca      2340
cattgggaga tctggttaca tgtttattct atatggattg cattgagagg atttgtataa      2400
cagaataagg tcttttttttc ttttctcttc tgagatggag tttcatccct attgcccaag      2460
ctagagtgca atggtgcaat ctaggctcac cgcaacctct gcctcctggg ttcaagcaat      2520
tctcctgcct cagccacctg aatagctggg actgcaggca tgcaccacac gcccggctga      2580
ttttgtattt ttagtagaga tggggtttca ccatgttggt caggctggtc ttgaactcct      2640
gacctcaagt gatctgcctg ccttggcctc ccaaagtgct gggtttacaa gcctgagcca      2700
ccgcatccag ccaggataag gtctaaaagt ggaaagaata gcatctactc ttgttcagga      2760
aacaatgagg acctgactgg gcagtaagag tggtgattaa tagataggga caaattgaag      2820
cagaatcgaa ctgttgatta gaggtaggga aatgattta atctgtgacc ttggtgaatg      2880
ggcaagtagc tatctaatga ctaaaatgga aaacactgga agagaaacag ttttagtata      2940
acaagtgaaa tacccatgct gagtctgagg tgcctatagg acatctatat aaataagccc      3000
agtacattgt ttgatatatg ggtttggcac tgaggttgga ggtcagaggt tagaaatcag      3060
agttgggaat tgggattata caggctgtat ttaagagttt agatataact gtgaatccaa      3120
gagtgtgatg aatacaaagt taaatgaagg acctttaatg aacaccaaca tttaatgtga      3180
aatctcaagg aagtatgaag taagacatag tccccaaaat ccccgatgat tttagaactc      3240
agtatcgatt ttaattagtg taatgccaat gtgggttaga atggaagtca acttgctgtt      3300
ggtttcagag caggtaggag ataaggttct agattttgac acagtgaaaa gctgaaacaa      3360
aaaggaaaag gtagggtgaa agatgggaaa tgtatgtaag gaggatgagc cacatggtat      3420
gggaggtata ctaaggactc tagggtcaga gaaatatggg ttatatccttt ctacaaaatt     3480 cacattcttg gctgggtgtg gtggctcacg cctgtgatcc cagcactttc agaggccgag      3540
gagggtggat cacctgatgt taggagttcg agatcagcct gaccaacatg gtgaaacccc      3600
cta                                                                    3603
```

<210> SEQ ID NO 2
<211> LENGTH: 350
<212> TYPE: DNA
<213> ORGANISM: Homo sapiens

<400> SEQUENCE: 2

```
aaagatggat gatgtgcctg agattctgat cacaagggga aatgttataa aataggtag    60
agaggagcca tgaatgacct ttaaactttg ttacaagtta tttttctgta acctggaagc   120
caacgaaaga tattgaataa ttcaagaaag gtggtggcat ggtttgattt gtgtctttaa   180
aagattattc tcacttagtg aagaaatgta ttttagaagt agagaaaatg ggagacaaat   240
agctgggctt ctgttgcagt agggaagaaa gtgacaatgc catttctatt atcagacttg   300
gaccatgacg gtgatgtcag tcgtgaacac aagaataggg ccacatttgt              350
```

<210> SEQ ID NO 3
<211> LENGTH: 21
<212> TYPE: DNA
<213> ORGANISM: Homo sapiens

<400> SEQUENCE: 3

```
gtgcacctca ctccagagga g                                              21
```

<210> SEQ ID NO 4
<211> LENGTH: 21
<212> TYPE: DNA
<213> ORGANISM: Homo sapiens

<400> SEQUENCE: 4

```
gtgcacctca ctccagtgga g                                              21
```

<210> SEQ ID NO 5
<211> LENGTH: 22
<212> TYPE: DNA
<213> ORGANISM: Homo sapiens

<400> SEQUENCE: 5

```
tttccactta ttcaaccttt ta                                             22
```

<210> SEQ ID NO 6
<211> LENGTH: 22
<212> TYPE: DNA
<213> ORGANISM: Homo sapiens

<400> SEQUENCE: 6

```
tgtggcccta ttcttgtgtt ca                                             22
```

<210> SEQ ID NO 7
<211> LENGTH: 22
<212> TYPE: DNA
<213> ORGANISM: Homo sapiens

<400> SEQUENCE: 7

```
cattgtcact ttcttcccta ct                                             22
```

<210> SEQ ID NO 8
<211> LENGTH: 22
<212> TYPE: DNA
<213> ORGANISM: Homo sapiens

<400> SEQUENCE: 8

```
taaaatacat ttcttcacta ag                                             22
```

<210> SEQ ID NO 9
<211> LENGTH: 22
<212> TYPE: DNA
<213> ORGANISM: Homo sapiens
```

```
<400> SEQUENCE: 9
actaagtgag aataatcttt ta                                            22

<210> SEQ ID NO 10
<211> LENGTH: 22
<212> TYPE: DNA
<213> ORGANISM: Homo sapiens

<400> SEQUENCE: 10
gccaccacct ttcttgaatt at                                            22

<210> SEQ ID NO 11
<211> LENGTH: 22
<212> TYPE: DNA
<213> ORGANISM: Homo sapiens

<400> SEQUENCE: 11
tcttgaatta ttcaatatct tt                                            22

<210> SEQ ID NO 12
<211> LENGTH: 22
<212> TYPE: DNA
<213> ORGANISM: Homo sapiens

<400> SEQUENCE: 12
ttaaaggtca ttcatggctc ct                                            22

<210> SEQ ID NO 13
<211> LENGTH: 2606
<212> TYPE: DNA
<213> ORGANISM: Homo sapiens

<400> SEQUENCE: 13
gcaatgaaaa taaatgtttt ttattaggca gaatccagat gctcaaggcc cttcataata     60
tcccccagtt tagtagttgg acttagggaa caaaggaacc tttaatagaa attggacagc    120
aagaaagcga gcttagtgat acttgtgggc cagggcatta gccacaccag ccaccacttt    180
ctgataggca gcctgcactg gtggggtgaa ttctttgcca aagtgatggg ccagcacaca    240
gaccagcacg ttgcccagga gctgtgggag gaagataaga ggtatgaaca tgattagcaa    300
aagggcctag cttggactca gaataatcca gccttatccc aaccataaaa taaaagcaga    360
atggtagctg gattgtagct gctattagca atatgaaacc tcttacatca gttacaattt    420
atatgcagaa atatttatat gcagagatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa aagaagaaag    600 catttttttaa aattacaaat gcaaaattac cctgatttgg tcaatatgtg tacacatatt    660
aaaacattac actttaaccc ataaatatgt ataatgatta tgtatcaatt aaaaataaaa    720
gaaaataaag tagggagatt atgaatatgc aaataagcac acatatattc caaatagtaa    780
tgtactaggc agactgtgta aagtttttttt ttaagttact taatgtatct cagagatatt    840
tccttttgtt atacacaatg ttaaggcatt aagtataata gtaaaaattg cggagaagaa    900
aaaaaaagaa agcaagaatt aaacaaaaga aaacaattgt tatgaacagc aaataaaaga    960
aactaaaacg atcctgagac ttccacactg atgcaatcat tcgtctgttt cccattctaa   1020 actgtacccct gttacttatc cccttcctat gacatgaact taaccataga aagaagggg   1080
```

| | |
|---|---|
| aaagaaaaca tcaagcgtcc catagactca ccctgaagtt ctcaggatcc acgtgcagct | 1140 |
| tgtcacagtg cagctcactc agtgtggcaa aggtgccctt gaggttgtcc aggtgagcca | 1200 |
| ggccatcact aaaggcaccg agcactttct tgccatgagc cttcacctta gggttgccca | 1260 |
| taacagcatc aggagtggac agatccccaa aggactcaaa gaacctctgg gtccaagggt | 1320 |
| agaccaccag cagcctaagg gtgggaaaat agaccaatag gcagagagag tcagtgccta | 1380 |
| tcagaaaccc aagagtcttc tctgtctcca catgcccagt ttctattggt ctccttaaac | 1440 |
| ctgtcttgta accttgatac caacctgccc agggcctcac caccaacttc atccacgttc | 1500 |
| accttgcccc acagggcagt aacggcagac ttctcctcag gagtcagatg caccatggtg | 1560 |
| tctgtttgag gttgctagtg aacacagttg tgtcagaagc aaatgtaagc aatagatggc | 1620 |
| tctgccctga cttttatgcc cagccctggc tcctgcsctc cctgctcctg ggagtagatt | 1680 |
| ggccaaccct agggtgtggc tccacaggt gaggtctaag tgatgacagc cgtacctgtc | 1740 |
| cttggctctt ctggcactgg cttaggagtt ggacttcaaa ccctcagccc tccctctaag | 1800 |
| atatatctct tggccccata ccatcagtac aaattgctac taaaaacatc ctcctttgca | 1860 |
| agtgtattta cgtaatattt ggaatcacag cttggtaagc atattgaaga tcgttttccc | 1920 |
| aattttctta ttacacaaat aagaagttga tgcactaaaa gtggaagagt tttgtctacc | 1980 |
| ataattcagc tttgggatat gtagatggat ctcttcctgc gtctccagaa tatgcaaaat | 2040 |
| acttacagga cagaatggat gaaaactcta cctcggttct aagcatatct tctccttatt | 2100 |
| tggattaaaa ccttctggta agaaaagaaa aatatatat atatatgtgt gtatatatac | 2160 |
| acacatacat atacatatat atgcattcat ttgttgttgt ttttcttaat ttgctcatgc | 2220 |
| atgctaataa attatgtcta aaaatagaat aaatacaaat caatgtgctc tgtgcattag | 2280 |
| ttacttatta ggttttggga acaagagat aaaaaactag agacctctta atgcagtcaa | 2340 |
| aaatacaaat aaataaaaag tcacttacaa cccaaagtgt gactatcaat ggggtaatca | 2400 |
| gtggtgtcaa ataggaggtt aactgggac atctaactgt ttctgcctgg actaatctgc | 2460 |
| aagagtgtct gggggaacaa aaagcctctg tgacttagaa agtaggggta ggaggggaaa | 2520 |
| aggtcttcta cttggctcag attattttttt tcctctagtc cactaagaat actgcgtttt | 2580 |
| aaaatcattt ccttgattca agttcc | 2606 |

<210> SEQ ID NO 14
<211> LENGTH: 606
<212> TYPE: DNA
<213> ORGANISM: Homo sapiens

<400> SEQUENCE: 14

| | |
|---|---|
| caccctgaag ttctcaggat ccacgtgcag cttgtcacag tgcagctcac tcagtgtggc | 60 |
| aaaggtgccc ttgaggttgt ccaggtgagc caggccatca ctaaaggcac cgagcacttt | 120 |
| cttgccatga gccttcacct tagggttgcc cataacagca tcaggagtgg acagatcccc | 180 |
| aaaggactca agaacctct gggtccaagg gtagaccacc agcagcctaa gggtgggaaa | 240 |
| atagaccaat aggcagagag agtcagtgcc tatcagaaac ccaagagtct tctctgtctc | 300 |
| cacatgccca gtttctattg gtctccttaa accgtcttg taaccttgat accaacctgc | 360 |
| ccagggcctc accaccaact tcatccacgt tcaccttgcc ccacagggca gtaacggcag | 420 |
| acttctcctc aggagtcaga tgcaccatgg tgtctgtttg aggttgctag tgaacacagt | 480 |
| tgtgtcagaa gcaaatgtaa gcaatagatg gctctgccct gacttttatg cccagccctg | 540 |
| gctcctgccc tccctgctcc tgggagtaga ttggccaacc ctagggtgtg gctccacagg | 600 | gtgagg                                                                    606

<210> SEQ ID NO 15
<211> LENGTH: 303
<212> TYPE: PRT
<213> ORGANISM: Ophiostoma novo-ulmi

<400> SEQUENCE: 15

Ser Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Met Leu Phe Lys Gln
            100                 105                 110

Ala Phe Cys Val Met Glu Asn Lys Glu His Leu Lys Ile Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Ile Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 16
<211> LENGTH: 110
<212> TYPE: DNA
<213> ORGANISM: Homo sapiens

<400> SEQUENCE: 16
tgggggcccc ttccccacac tatctcaatg caaatatctg tctgaaacgg tccctggcta    60
aactccaccc atgggttggc cagccttgcc ttgaccaata gccttgacaa                110

<210> SEQ ID NO 17
<211> LENGTH: 110
<212> TYPE: DNA
<213> ORGANISM: Homo sapiens

<400> SEQUENCE: 17
tgggggcgcc ttccccacac tatctcaatg caaatatctg tctgaaacgg tccctggcta    60
aactccaccc atgggttggc cagccttgcc ttgaccaata gccttgacaa             110

<210> SEQ ID NO 18
<211> LENGTH: 110
<212> TYPE: DNA
<213> ORGANISM: Homo sapiens

<400> SEQUENCE: 18
tgggggcccc ttccccacac tatctcaatg caaacatctg tctgaaacgg tccctggcta    60
aactccaccc atgggttggc cagccttgcc ttgaccaata gccttgacaa             110

<210> SEQ ID NO 19
<211> LENGTH: 110
<212> TYPE: DNA
<213> ORGANISM: Homo sapiens

<400> SEQUENCE: 19
tgggggcccc ttccccacac tatctcaatg caaatatctg tctgaaacgg tccctggcta    60
aactccaccc atgggttggc cagccttgcc ttgactaata gccttgacaa             110

<210> SEQ ID NO 20
<211> LENGTH: 110
<212> TYPE: DNA
<213> ORGANISM: Homo sapiens

<400> SEQUENCE: 20
tgggggcccc ttctccacac tatctcaatg caaatatctg tctgaaacgg tccctggcta    60
aactccaccc atgggttggc cagccttgcc ttgaccaata gccttgacaa             110

<210> SEQ ID NO 21
<211> LENGTH: 110
<212> TYPE: DNA
<213> ORGANISM: Homo sapiens

<400> SEQUENCE: 21
tgggggcccc ttccccacac tatctcaatg caaacatctg tctgaaacgg tccctggcta    60
aactccaccc atgggttggc cagccttgcc ttgaccaata gccttgacaa             110

<210> SEQ ID NO 22
<211> LENGTH: 110
<212> TYPE: DNA
<213> ORGANISM: Homo sapiens

<400> SEQUENCE: 22
tgggggcccc ttccccacac tatctcaatg caaatatctg tctgaaacgg tccctggcta    60
aactccaccc atgggttggc cagccttgcc ttaaccaata gccttgacaa             110

<210> SEQ ID NO 23
<211> LENGTH: 110
<212> TYPE: DNA
<213> ORGANISM: Homo sapiens

<400> SEQUENCE: 23

```
tgggggcccc ttccccacac tatctcaatg caaatatctg tctgaaacgg tccctggcta    60
aactccaccc atgggttggc cagccttgcc ttgaccaata gccttgacaa              110
```

<210> SEQ ID NO 24
<211> LENGTH: 2508
<212> TYPE: DNA
<213> ORGANISM: Homo sapiens

<400> SEQUENCE: 24

```
atgtctcgcc gcaagcaagg caaacccag cacttaagca aacgggaatt ctcgcccgag     60
cctcttgaag ccattcttac agatgatgaa ccagaccacg gccgttggg agctccagaa    120
ggggatcatg acctcctcac ctgtgggcag tgccagatga acttcccatt gggggacatt   180
cttattttta tcgagcacaa acggaaacaa tgcaatggca gcctctgctt agaaaaagct   240
gtggataagc caccttcccc ttcaccaatc gagatgaaaa agcatccaa tcccgtggag    300
gttggcatcc aggtcacgcc agaggatgac gattgtttat caacgtcatc tagaggaatt   360
tgccccaaac aggaacacat agcagataaa cttctgcact ggaggggcct ctcctcccct   420
cgttctgcac atggagctct aatccccacg cctgggatga gtgcagaata tgccccgcag   480
ggtatttgta aagatgagcc cagcagctac acatgtacaa cttgcaaaca gccattcacc   540
agtgcatggt ttctcttgca acacgcacag aacactcatg gattaagaat ctacttagaa   600
agcgaacacg gaagtcccct gaccccgcgg gttggtatcc cttcaggact aggtgcagaa   660
tgtccttccc agccacctct ccatgggatt catattgcag acaataaccc ctttaacctg   720
ctaagaatac caggatcagt atcgagagag gcttccggcc tggcagaagg gcgctttcca   780
cccactcccc ccctgtttag tccaccaccg agacatcact tggacccccca ccgcatagag   840
cgcctggggg cggaagagat ggccctggcc acccatcacc cgagtgcctt tgacagggtg   900
ctgcggttga atccaatggc tatggagcct ccgccatgg atttctctag gagacttaga   960
gagctggcag ggaacacgtc tagcccaccg ctgtccccag gccggcccag ccctatgcaa  1020
aggttactgc aaccattcca gccaggtagc aagccgccct tcctggcgac gccccccctc  1080
cctcctctgc aatccgcccc tcctccctcc agccccccgg tcaagtccaa gtcatgcgag  1140
ttctgcggca agacgttcaa atttcagagc aacctggtgg tgcaccggcg cagccacacg  1200
ggcgagaagc cctacaagtg caacctgtgc gaccacgcgt gcacccaggc cagcaagctg  1260
aagcgccaca tgaagacgca catgcacaaa tcgtccccca tgacggtcaa gtccgacgac  1320
ggtctctcca ccgccagctc cccggaaccc ggcaccagcg acttggtggg cagcgccagc  1380
agcgcgctca gtccgtggt ggccaagttc aagagcgaga acgaccccaa cctgatcccg  1440
gagaacgggg acgaggagga gaggaggac gacgaggaag aggaagaaga ggaggaagag   1500
gaggaggagg agctgacgga gagcgagagg gtggactacg gcttcgggct gagcctggag  1560
gcggcgcgcc accacgagaa cagctcgcgg ggcgcggtcg tgggcgtggg cgacgagagc  1620
cgcgccctgc ccgacgtcat gcagggcatg gtgctcagct ccatgcagca cttcagcgag  1680
gccttccacc aggtcctggg cgagaagcat aagcgcggcc acctggccga ggccgagggc  1740
cacagggaca cttgcgacga agactcggtg gccggcgagt cggaccgcat agacgatggc  1800
actgttaatg gccgcggctg ctccccgggc gagtcggcct cggggggcct gtccaaaaag  1860
ctgctgctgg gcagccccag ctcgctgagc cccttctcta gcgcatcaa gctcgagaag  1920
gagttcgacc tgccccggc cgcgatgccc aacacggaga acgtgtactc gcagtggctc  1980
```

```
gccggctacg cggcctccag gcagctcaaa gatcccttcc ttagcttcgg agactccaga    2040
caatcgcctt ttgcctcctc gtcggagcac tcctcggaga acgggagttt gcgcttctcc    2100
acaccgcccg gggagctgga cggagggatc tcggggcgca gcggcacggg aagtggaggg    2160
agcacgcccc atattagtgg tccgggcccg ggcaggccca gctcaaaaga gggcagacgc    2220
agcgacactt gtgagtactg tgggaaagtc ttcaagaact gtagcaatct cactgtccac    2280
aggagaagcc acacgggcga aaggccttat aaatgcgagc tgtgcaacta tgcctgtgcc    2340
cagagtagca agctcaccag gcacatgaaa acgcatggcc aggtggggaa ggacgtttac    2400
aaatgtgaaa tttgtaagat gccttttagc gtgtacagta ccctggagaa acacatgaaa    2460
aaatggcaca gtgatcgagt gttgaataat gatataaaaa ctgaatag                 2508

<210> SEQ ID NO 25
<211> LENGTH: 22
<212> TYPE: DNA
<213> ORGANISM: Homo sapiens

<400> SEQUENCE: 25
atgggattca tattgcagac aa                                              22

<210> SEQ ID NO 26
<211> LENGTH: 22
<212> TYPE: DNA
<213> ORGANISM: Homo sapiens

<400> SEQUENCE: 26
agccattgga ttcaaccgca gc                                              22

<210> SEQ ID NO 27
<211> LENGTH: 22
<212> TYPE: DNA
<213> ORGANISM: Homo sapiens

<400> SEQUENCE: 27
caaacagcca ttcaccagtg ca                                              22

<210> SEQ ID NO 28
<211> LENGTH: 771
<212> TYPE: DNA
<213> ORGANISM: Artificial Sequence
<220> FEATURE:
<223> OTHER INFORMATION: Nucleotide Sequence of I-HjeMI, Codon Optimized
      for Expression in E. coli

<400> SEQUENCE: 28
atgggatccc acatggacct gacctacgct tacctggttg gtctgttcga aggtgacggt     60
tacttctcta tcaccaaaaa gggtaaatac ctgacctacg aactgggtat cgaactgtct    120
atcaaagacg ttcagctgat ctacaaaatc aaagacatcc tgggtgttgg taaagtttct    180
ttccgtaaac gtaacgaaat cgaaatggtt tctctgcgta ccgtgacaa gaatcacctg    240 aaaaacttca tcctgccgat cttcgacaaa tacccgatgc tgtctaacaa gcagtacgac    300
tacctgcgtt tcaagacgc tctcctgtct aacattatct actctgacga tctgccggaa    360
tacgctcgtt ctaacgaatc tatcaactct gttgactcta ttatcaacac ctcttacttc    420
tctgcttggc tggttggttt catcgaagct gaaggttgct ctctctaccta caaactgaac    480 aaagatgacg attacctgat cgcttctttc gacatcgctc agaaagacgg tgacatcctg    540
atctctgcta tccacaaaata cctgtctttc accacgaaaa tctacctgga caaaaccaac    600
```

-continued

```
tgctctcgtc tgaaagtgac cggtgtacgt tctgttaaaa acgtggttaa attcatccag        660
ggtgctccgg ttaaactgct cggtaacaag aaactgcagt acaaactgtg gatcaaacag        720
ctgcgtaaaa tctctcgtta ctctgaaaaa atccagctgc cgtctaacta c                 771
```

<210> SEQ ID NO 29
<211> LENGTH: 771
<212> TYPE: DNA
<213> ORGANISM: Artificial Sequence
<220> FEATURE:
<223> OTHER INFORMATION: Nucleotide Sequence of I-HjeMI, Codon Optimized for Expression in Mammals

<400> SEQUENCE: 29

```
atgggcagcc acatggacct gacctacgcc tatctggtcg gcctgttcga gggcgacggc        60
tattttagca taaccaagaa gggcaagtat ctgacgtatg aactgggcat cgagctctcc        120
atcaaggacg tgcagctcat ctacaagatc aaggacatcc tcggcgtggg caaagtgtct        180
tttaggaaga ggaacgagat cgagatggtc agcctgcgaa tcaggacaa aaaccacctg         240 aagaacttca tcctgcccat cttcgacaag tacccatgc tgagcaacaa gcagtacgac        300
tatctccgat tcaaggatgc cctcctgtcc aacatcatct atagcgacga cctgcccgag        360
tacgccagga gcaacgagtc aatcaatagc gtggacagca tcatcaacac ctcatacttc        420
agcgcctggc tggttggctt catcgaggcc gagggctgct tcagcaccta caagctcaac        480
aaggacgacg attatttgat cgcgagcttc gatatagccc agaaggacgg cgacattctc        540
atctccgcga tccacaaata cctgagcttc acgaccaaaa tctacctgga caagaccaac        600
tgtagcaggc tcaaggtcac cggcgtgagg agcgtcaaga acgtggttaa gttcatccag        660
ggtgcgccgg tcaagttgct gggtaacaag aagctgcagt acaaactttg gataaagcag        720
ctgcgcaaga tctcccgata cagcgagaaa atccagctgc ccagtaacta c                 771
```

<210> SEQ ID NO 30
<211> LENGTH: 254
<212> TYPE: PRT
<213> ORGANISM: Trichoderma reesei

<400> SEQUENCE: 30

```
Met Gly Asp Leu Thr Tyr Ala Tyr Leu Val Gly Leu Phe Glu Gly Asp
1               5                   10                  15

Gly Tyr Phe Ser Ile Thr Lys Lys Gly Lys Tyr Leu Thr Tyr Glu Leu
            20                  25                  30

Gly Ile Glu Leu Ser Ile Lys Asp Val Gln Leu Ile Tyr Lys Ile Lys
        35                  40                  45

Asp Ile Leu Gly Val Gly Lys Val Ser Phe Arg Lys Arg Asn Glu Ile
    50                  55                  60

Glu Met Val Ser Leu Arg Ile Arg Asp Lys Asn His Leu Lys Asn Phe
65                  70                  75                  80

Ile Leu Pro Ile Phe Asp Lys Tyr Pro Met Leu Ser Asn Lys Gln Tyr
                85                  90                  95

Asp Tyr Leu Arg Phe Lys Asp Ala Leu Leu Ser Asn Ile Ile Tyr Ser
            100                 105                 110

Asp Asp Leu Pro Glu Tyr Ala Arg Ser Asn Glu Ser Ile Asn Ser Val
        115                 120                 125

Asp Ser Ile Ile Asn Thr Ser Tyr Phe Ser Ala Trp Leu Val Gly Phe
    130                 135                 140
```

```
Ile Glu Ala Glu Gly Cys Phe Ser Thr Tyr Lys Leu Asn Lys Asp Asp
145                 150                 155                 160

Asp Tyr Leu Ile Ala Ser Phe Asp Ile Ala Gln Lys Asp Gly Asp Ile
                165                 170                 175

Leu Ile Ser Ala Ile His Lys Tyr Leu Ser Phe Thr Thr Lys Ile Tyr
            180                 185                 190

Leu Asp Lys Thr Asn Cys Ser Arg Leu Lys Val Thr Gly Val Arg Ser
        195                 200                 205

Val Lys Asn Val Val Lys Phe Ile Gln Gly Ala Pro Val Lys Leu Leu
    210                 215                 220

Gly Asn Lys Lys Leu Gln Tyr Lys Leu Trp Ile Lys Gln Leu Arg Lys
225                 230                 235                 240

Ile Ser Arg Tyr Ser Glu Lys Ile Gln Leu Pro Ser Asn Tyr
                245                 250
```

<210> SEQ ID NO 31
<211> LENGTH: 768
<212> TYPE: DNA
<213> ORGANISM: Artificial Sequence
<220> FEATURE:
<223> OTHER INFORMATION: Nucleotide Sequence for a BCL11A Gene Targeting Nuclease Based on the Homing Endonuclease I-HjeMI; Codon Optimized for Expression in E. coli and Obtained through Directed Evolution in IVC and in Bacteria

<400> SEQUENCE: 31

```
atgggatccc acatggacct gacctacgct tacctggttg gtctgttcga aggtgacggt       60
tacttcacta tcgctaaagc gggtaagtac ctgaattacg agctgggtat cacgctgtct      120
atcaaagacg ctcagctgat ctacaaaatc aagacatcc tgggtgttgg taatgtttat      180
ttccggaaat ataggcagca tgaaatggtt tctctgcgga tccaggacaa gaatcacctg      240
aaaaacttca tcctgccgat cttcgacaaa tacccgatgc tgtctaacaa gcagtacgac      300
tacctgcgtt tcaaagacgc tctcctgtct aacattatct actctgacga tctgccggaa      360
tacgctcgtt ctaacgaatc tatcaactct gttgactcta ttatcaacac ctcttacttc      420
tctgcttggc tggttggttt catcgaagct gaaggttgct tcacgaccta caaagcgagt      480
aaagataagt acctgacggc tgggttcagt atcgctcaga agacggtga catcctgatc      540
tctgctatcc acaaatacct gtctttcacc acgaaaccgt acaaggacaa aaccaactgc      600
tctcatctga aggtgaccgg tgtacgttct gttaacaacg tggttaaatt catccagggt      660
gctccggtta aactgctcgg taacaagaaa ctgcagtaca aactgtggat caaacagctg      720
cgtaaaatct ctcgttactc tgaaaaaatc cagctgccgt ctaactac                   768
```

<210> SEQ ID NO 32
<211> LENGTH: 768
<212> TYPE: DNA
<213> ORGANISM: Artificial Sequence
<220> FEATURE:
<223> OTHER INFORMATION: Nucleotide Sequence of a BCL11A Gene Targeting Nuclease Based on the Homing Endonuclease I-HjeMI; Codon Optimized for Expression in Mammals and Obtained through Directed Evolution in IVC and in Bacteria

<400> SEQUENCE: 32

```
atgggcagcc acatggacct gacctacgcc tatctggtcg gcctgttcga gggcgacggc       60
tattttacaa tagctaaggc cggcaagtat ctgaactacg agctgggcat cacactctcc      120
atcaaggacg ctcagctcat ctacaagatc aaggacatcc tcggcgtggg caacgtgtac      180
```

-continued

```
tttaggaagt acaggcaaca tgagatggtc agcctgcgaa tccaggacaa aaaccacctg    240
aagaacttca tcctgcccat cttcgacaag tacccatgc tgagcaacaa gcagtacgac     300
tacctgcgat tcaaggatgc cctcctgtcc aacatcatct atagcgacga cctgcccgag    360
tacgccagga gcaacgagtc aatcaatagc gtggacagca tcatcaacac ctcatacttc    420
agcgcctggc tggttggctt catcgaggcc gagggctgct tcaccaccta caaggcatcc    480
aaggacaagt acctgacagc gggcttctcc atagcccaga aggacggcga cattctcatc    540
tccgcgatcc acaaatacct gagcttcacg accaaaccct acaaagacaa gaccaactgt    600
agccacctca aggtcaccgg cgtgaggagc gtcaataacg tggttaagtt catccagggt    660
gcgccggtca agctgctggg taacaagaag ctgcagtaca aactttggat aaagcagctg    720
cgcaagatct cccgatacag cgagaaaatc cagctgccca gtaactac                 768
```

<210> SEQ ID NO 33
<211> LENGTH: 256
<212> TYPE: PRT
<213> ORGANISM: Artificial Sequence
<220> FEATURE:
<223> OTHER INFORMATION: Amino Acid Sequence of a BCL11A Gene Targeting Nuclease Based on the Homing Endonuclease I-HjeMI

<400> SEQUENCE: 33

```
Met Gly Ser His Met Asp Leu Thr Tyr Ala Tyr Leu Val Gly Leu Phe
1               5                   10                  15

Glu Gly Asp Gly Tyr Phe Thr Ile Ala Lys Ala Gly Lys Tyr Leu Asn
                20                  25                  30

Tyr Glu Leu Gly Ile Thr Leu Ser Ile Lys Asp Ala Gln Leu Ile Tyr
            35                  40                  45

Lys Ile Lys Asp Ile Leu Gly Val Gly Asn Val Tyr Phe Arg Lys Tyr
        50                  55                  60

Arg Gln His Glu Met Val Ser Leu Arg Ile Gln Asp Lys Asn His Leu
65                  70                  75                  80

Lys Asn Phe Ile Leu Pro Ile Phe Asp Lys Tyr Pro Met Leu Ser Asn
                85                  90                  95

Lys Gln Tyr Asp Tyr Leu Arg Phe Lys Asp Ala Leu Leu Ser Asn Ile
            100                 105                 110

Ile Tyr Ser Asp Asp Leu Pro Glu Tyr Ala Arg Ser Asn Glu Ser Ile
        115                 120                 125

Asn Ser Val Asp Ser Ile Ile Asn Thr Ser Tyr Phe Ser Ala Trp Leu
    130                 135                 140

Val Gly Phe Ile Glu Ala Glu Gly Cys Phe Thr Thr Tyr Lys Ala Ser
145                 150                 155                 160

Lys Asp Lys Tyr Leu Thr Ala Gly Phe Ser Ile Ala Gln Lys Asp Gly
                165                 170                 175

Asp Ile Leu Ile Ser Ala Ile His Lys Tyr Leu Ser Phe Thr Thr Lys
            180                 185                 190

Pro Tyr Lys Asp Lys Thr Asn Cys Ser His Leu Lys Val Thr Gly Val
        195                 200                 205

Arg Ser Val Asn Asn Val Val Lys Phe Ile Gln Gly Ala Pro Val Lys
    210                 215                 220

Leu Leu Gly Asn Lys Lys Leu Gln Tyr Lys Leu Trp Ile Lys Gln Leu
225                 230                 235                 240

Arg Lys Ile Ser Arg Tyr Ser Glu Lys Ile Gln Leu Pro Ser Asn Tyr
                245                 250                 255
```

<210> SEQ ID NO 34
<211> LENGTH: 912
<212> TYPE: DNA
<213> ORGANISM: Artificial Sequence
<220> FEATURE:
<223> OTHER INFORMATION: Nucleotide Sequence of I-OnuI, Codon Optimized for Expression in E. coli

<400> SEQUENCE: 34

| | | | | | |
|---|---|---|---|---|---|
| atgtccgcct | acatgtcccg | tcgcgagtcc | attaacccgt | ggattctcac | cggtttcgcc | 60 |
| gacgcggaag | gctcctttt | gctgcgcatc | cgcaacaaca | acaagtccag | cgtcggctac | 120 |
| tccactgagc | tcggcttcca | aattacactt | cataacaagg | acaagagcat | tcttgagaac | 180 |
| atccagtcaa | catggaaggt | gggcgtgatc | gccaacagcg | gtgacaacgc | cgtgtcgctg | 240 |
| aaggtcacgc | gttttgagga | cctgaaggtc | attatcgacc | attttgaaaa | atacccactg | 300 |
| attacgcaga | agctcggtga | ctacatgctg | tttaagcagg | cgttttgcgt | catggagaac | 360 |
| aaggagcatt | tgaagattaa | tggtatcaag | gagctggtgc | gcattaaggc | aaagctcaat | 420 |
| tggggtctga | cggatgagct | gaagaaggcc | tttccggaga | tcatctcgaa | ggagcgctcc | 480 |
| ctcatcaaca | gaacatccc | taatttcaag | tggctggcgg | ttttacctc | gggcgagggt | 540 |
| tgcttctttg | ttaacctgat | caagtcaaag | tcgaagctag | gtgtccaggt | gcagctggtg | 600 |
| ttcagcatta | cccaacacat | caaggataag | aacctcatga | actctctgat | tacctacttg | 660 |
| ggctgcggct | acattaagga | gaaaaacaag | agtgagttct | cctggcttga | cttcgtcgtc | 720 |
| acgaaattct | ccgacatcaa | cgacaagatc | attccggtct | ttcaggaaaa | cacgctcatc | 780 |
| ggcgtgaagc | tcgaggactt | cgaggattgg | tgtaaggtcg | ctaagctgat | cgaggagaaa | 840 |
| aagcacctga | cagaaagtgg | cctggacgag | atcaagaaga | ttaagctgaa | catgaacaag | 900 |
| ggcagagtat | tc | | | | | 912 |

<210> SEQ ID NO 35
<211> LENGTH: 1998
<212> TYPE: DNA
<213> ORGANISM: Artificial Sequence
<220> FEATURE:
<223> OTHER INFORMATION: Nucleotide Sequence of MegaTAL:5.5 RVD + Y2 I-AniI

<400> SEQUENCE: 35

| | | | | | |
|---|---|---|---|---|---|
| gtggatctac | gcacgctcgg | ctacagtcag | cagcagcaag | agaagatcaa | accgaaggtg | 60 |
| cgttcgacag | tggcgcagca | ccacgaggca | ctggtgggcc | atgggtttac | acacgcgcac | 120 |
| atcgttgcgc | tcagccaaca | cccggcagcg | ttagggaccg | tcgctgtcac | gtatcagcac | 180 |
| ataatcacgg | cgttgccaga | ggcgacacac | gaagacatcg | ttggcgtcgg | caaacagtgg | 240 |
| tccggcgcac | gcgccctgga | ggccttgctc | acggatgcgg | gggagttgag | aggtccgccg | 300 |
| ttacagttgg | acacaggcca | acttgtgaag | attgcaaaac | gtggcggcgt | gaccgcaatg | 360 |
| gaggcagtgc | atgcatcgcg | caatgcactg | acgggtgccc | ccctgaacct | gaccccggac | 420 |
| caagtggtgg | ctatcgccag | caacaatggc | ggcaagcaag | cgctcgaaac | ggtgcagcgg | 480 |
| ctgttgccgg | tgctgtgcca | ggaccatggc | ctgactccgg | accaagtggt | ggctatcgcc | 540 |
| agccacgatg | gcggcaagca | agcgctcgaa | acggtgcagc | ggctgttgcc | ggtgctgtgc | 600 |
| caggaccatg | gcctgacccc | ggaccaagtg | gtggctatcg | ccagcaacat | tggcggcaag | 660 |
| caagcgctcg | aaacggtgca | gcggctgttg | ccggtgctgt | gccaggacca | tggcctgacc | 720 |
| ccggaccaag | tggtggctat | cgccagcaac | aatggcggca | agcaagcgct | cgaaacggtg | 780 |

```
cagcggctgt tgccggtgct gtgccaggac catggcctga ctccggacca agtggtggct    840
atcgccagcc acgatggcgg caagcaagcg ctcgaaacgg tgcagcggct gttgccggtg    900
ctgtgccagg accatggcct gaccccggac caagtggtgg ctatcgccag caacggtggc    960
ggcaagcaag cgctcgaaag cattgtggcc cagctgagcc ggcctgatcc ggcgttggcc   1020
gcgttgacca acgaccacct cgtcgccttg gcctgcctcg gcggacgtcc tgccatggat   1080
gcagtgaaaa agggattgcc gcacgcgccg gaattgatca aaagagtcaa tcgccgtatt   1140
ggcgaacgca cgtcccatcg cgttgcgata tctagagtgg aggaagcga tcttacgtac    1200 gcgtatttag ttggtctcta cgaaggggat ggatacttta gtatcaccaa gaaaggcaag   1260
tacttgactt atgaattagg tattgagctg agcatcaaag acgtccaatt gatttacaag   1320
atcaagaaaa tcctaggtat tggcatcgta agcttcagga agagaaacga gattgaaatg   1380
gttgcattga ggatccgtga taagaatcat ctaaaatcta agatattgcc tatatttgag   1440
aagtatccaa tgttttccaa caaacagtac gactatttaa gattcaggaa tgcattgtta   1500
tctggcatta tatacctaga agacttgcct gattacacta gaagtgacga accattgaat   1560
tctatagaat ccattatcaa cacatcatac ttctccgcct ggctagttgg atttatagaa   1620
gctgagggct gtttcagtgt gtacaagctg aacaaagacg atgactactt gattgcttca   1680
ttcgacattg cccaaagaga tggtgatatc ttgatttcag caattaggaa gtacttaagt   1740
ttcactacta aggtttacct agacaagact aattgtagca aattgaaggt cactagtgtt   1800
agatccgtcg agaacatcat taagtttctg cagaatgctc ctgtcaaatt gttaggcaac   1860
aagaaactgc aatacaagtt gtggttgaaa caactaagga agatttctag gtattccgag   1920
aagatcaaga ttccatcaaa ctacgtcgac cgagcatctt accgccattt atacccatat   1980
ttgttctgtt tttcttga                                                  1998
```

<210> SEQ ID NO 36
<211> LENGTH: 665
<212> TYPE: PRT
<213> ORGANISM: Artificial Sequence
<220> FEATURE:
<223> OTHER INFORMATION: Amino Acid Sequence of MegaTAL:5.5 RVD + Y2
    I-AniI

<400> SEQUENCE: 36

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Thr Tyr Gln His Ile Ile Thr Ala
    50                  55                  60

Leu Pro Glu Ala Thr His Glu Asp Ile Val Gly Val Gly Lys Gln Trp
65                  70                  75                  80

Ser Gly Ala Arg Ala Leu Glu Ala Leu Leu Thr Asp Ala Gly Glu Leu
                85                  90                  95

Arg Gly Pro Pro Leu Gln Leu Asp Thr Gly Gln Leu Val Lys Ile Ala
            100                 105                 110

Lys Arg Gly Gly Val Thr Ala Met Glu Ala Val His Ala Ser Arg Asn
        115                 120                 125

Ala Leu Thr Gly Ala Pro Leu Asn Leu Thr Pro Asp Gln Val Val Ala

```
                130              135              140
Ile Ala Ser Asn Asn Gly Gly Lys Gln Ala Leu Glu Thr Val Gln Arg
145                 150              155                 160

Leu Leu Pro Val Leu Cys Gln Asp His Gly Leu Thr Pro Asp Gln Val
                165              170              175

Val Ala Ile Ala Ser His Asp Gly Gly Lys Gln Ala Leu Glu Thr Val
                180              185              190

Gln Arg Leu Leu Pro Val Leu Cys Gln Asp His Gly Leu Thr Pro Asp
            195              200              205

Gln Val Val Ala Ile Ala Ser Asn Ile Gly Gly Lys Gln Ala Leu Glu
210              215              220

Thr Val Gln Arg Leu Leu Pro Val Leu Cys Gln Asp His Gly Leu Thr
225                 230              235              240

Pro Asp Gln Val Val Ala Ile Ala Ser Asn Asn Gly Gly Lys Gln Ala
                245              250              255

Leu Glu Thr Val Gln Arg Leu Leu Pro Val Leu Cys Gln Asp His Gly
            260              265              270

Leu Thr Pro Asp Gln Val Val Ala Ile Ala Ser His Asp Gly Gly Lys
            275              280              285

Gln Ala Leu Glu Thr Val Gln Arg Leu Leu Pro Val Leu Cys Gln Asp
            290              295              300

His Gly Leu Thr Pro Asp Gln Val Val Ala Ile Ala Ser Asn Gly Gly
305                 310              315                 320

Gly Lys Gln Ala Leu Glu Ser Ile Val Ala Gln Leu Ser Arg Pro Asp
                325              330              335

Pro Ala Leu Ala Ala Leu Thr Asn Asp His Leu Val Ala Leu Ala Cys
            340              345              350

Leu Gly Gly Arg Pro Ala Met Asp Ala Val Lys Lys Gly Leu Pro His
            355              360              365

Ala Pro Glu Leu Ile Arg Arg Val Asn Arg Arg Ile Gly Glu Arg Thr
370              375              380

Ser His Arg Val Ala Ile Ser Arg Val Gly Gly Ser Asp Leu Thr Tyr
385                 390              395                 400

Ala Tyr Leu Val Gly Leu Tyr Glu Gly Asp Gly Tyr Phe Ser Ile Thr
                405              410              415

Lys Lys Gly Lys Tyr Leu Thr Tyr Glu Leu Gly Ile Glu Leu Ser Ile
            420              425              430

Lys Asp Val Gln Leu Ile Tyr Lys Ile Lys Lys Ile Leu Gly Ile Gly
            435              440              445

Ile Val Ser Phe Arg Lys Arg Asn Glu Ile Glu Met Val Ala Leu Arg
450              455              460

Ile Arg Asp Lys Asn His Leu Lys Ser Lys Ile Leu Pro Ile Phe Glu
465                 470              475              480

Lys Tyr Pro Met Phe Ser Asn Lys Gln Tyr Asp Tyr Leu Arg Phe Arg
                485              490              495

Asn Ala Leu Leu Ser Gly Ile Ile Tyr Leu Glu Asp Leu Pro Asp Tyr
            500              505              510

Thr Arg Ser Asp Glu Pro Leu Asn Ser Ile Glu Ser Ile Ile Asn Thr
            515              520              525

Ser Tyr Phe Ser Ala Trp Leu Val Gly Phe Ile Glu Ala Glu Gly Cys
530              535              540

Phe Ser Val Tyr Lys Leu Asn Lys Asp Asp Tyr Leu Ile Ala Ser
545                 550              555              560
```

```
Phe Asp Ile Ala Gln Arg Asp Gly Asp Ile Leu Ile Ser Ala Ile Arg
                565                 570                 575
Lys Tyr Leu Ser Phe Thr Thr Lys Val Tyr Leu Asp Lys Thr Asn Cys
            580                 585                 590
Ser Lys Leu Lys Val Thr Ser Val Arg Ser Val Glu Asn Ile Ile Lys
        595                 600                 605
Phe Leu Gln Asn Ala Pro Val Lys Leu Leu Gly Asn Lys Lys Leu Gln
    610                 615                 620
Tyr Lys Leu Trp Leu Lys Gln Leu Arg Lys Ile Ser Arg Tyr Ser Glu
625                 630                 635                 640
Lys Ile Lys Ile Pro Ser Asn Tyr Val Asp Arg Ala Ser Tyr Arg His
                645                 650                 655
Leu Tyr Pro Tyr Leu Phe Cys Phe Ser
                660             665
```

<210> SEQ ID NO 37
<211> LENGTH: 4146
<212> TYPE: DNA
<213> ORGANISM: Artificial Sequence
<220> FEATURE:
<223> OTHER INFORMATION: Engineered type II CRISPR system for human
      cells; expression format and full sequence of cas9 gene insert of
      Mali et al.

<400> SEQUENCE: 37

```
gccaccatgg acaagaagta ctccattggg ctcgatatcg gcacaaacag cgtcggctgg      60
gccgtcatta cggacgagta caaggtgccg agcaaaaaat tcaaagttct gggcaatacc     120
gatcgccaca gcataaagaa gaacctcatt ggcgccctcc tgttcgactc cggggagacg     180
gccgaagcca cgcggctcaa gaacagcagg cgcagat ataccgcag aaagaatcgg         240 atctgctacc tgcaggagat ctttagtaat gagatggcta aggtggatga ctctttcttc     300
cataggctgg aggagtcctt tttggtggag gaggataaaa agcacgagcg ccacccaatc     360
tttggcaata tcgtggacga ggtggcgtac catgaaaagt acccaaccat atatcatctg     420
aggaagaagc ttgtagacag tactgataag gctgacttgc ggttgatcta tctcgcgctg     480
gcgcatatga tcaaatttcg gggacacttc ctcatcgagg gggacctgaa cccagacaac     540
agcgatgtcg acaaactctt tatccaactg gttcagactt acaatcagct tttcgaagag     600
aacccgatca acgcatccgg agttgacgcc aaagcaatcc tgagcgctag gctgtccaaa     660
tcccggcggc tcgaaaaacct catcgcacag ctccctgggg agaagaagaa cggcctgttt     720
ggtaatctta tcgccctgtc actcgggctg accccaact ttaaatctaa cttcgacctg     780
gccgaagatg ccaagcttca actgagcaaa gacacctacg atgatgatct cgacaatctg     840
ctggcccaga tcggcgacca gtacgcagac cttttttttgg cggcaaagaa cctgtcagac     900
gccattctgc tgagtgatat tctgcgagtg aacacggaga tcaccaaagc tccgctgagc     960
gctagtatga tcaagcgcta tgatgagcac caccaagact tgactttgct gaaggccctt    1020
gtcagacagc aactgcctga aagtacaag gaaattttct tcgatcagtc taaaaatggc     1080
tacgccggat acattgacgg cggagcaagc aggaggaat tttacaaatt tattaagccc     1140
atcttggaaa aaatggacgg caccgaggag ctgctggtaa agcttaacag agaagatctg    1200
ttgcgcaaac agcgcacttt cgacaatgga agcatccccc accagattca cctgggcgaa    1260
ctgcacgcta tcctcaggcg gcaagaggat ttctacccct ttttgaaaga taacagggaa    1320
aagattgaga aaatcctcac atttcggata ccctactatg taggccccct cgcccgggga    1380
```

```
aattccagat tcgcgtggat gactcgcaaa tcagaagaga ccatcactcc ctggaacttc    1440
gaggaagtcg tggataaggg ggcctctgcc cagtccttca tcgaaggat gactaacttt    1500 gataaaaatc tgcctaacga aaaggtgctt cctaaacact ctctgctgta cgagtacttc    1560
acagtttata cgagctcac caaggtcaaa tacgtcacag aagggatgag aaagccagca    1620
ttcctgtctg gagagcagaa gaaagctatc gtggacctcc tcttcaagac gaaccggaaa    1680
gttaccgtga acagctcaa agaagactat ttcaaaaaga ttgaatgttt cgactctgtt    1740
gaaatcagcg gagtggagga tcgcttcaac gcatccctgg gaacgtatca cgatctcctg    1800
aaaatcatta aagacaagga cttcctggac aatgaggaga acgaggacat tcttgaggac    1860
attgtcctca cccttacgtt gtttgaagat agggagatga ttgaagaacg cttgaaaact    1920
tacgctcatc tcttcgacga caaagtcatg aaacagctca agaggcgccg atatacagga    1980
tgggggcggc tgtcaagaaa actgatcaat gggatccgag acaagcagag tggaaagaca    2040
atcctggatt tcttaagtc cgatggattt gccaaccgga acttcatgca gttgatccat    2100
gatgactctc tcacctttaa ggaggacatc cagaaagcac aagtttctgg ccaggggggac   2160 agtcttcacg agcacatcgc taatcttgca ggtagcccag ctatcaaaaa gggaatactg    2220
cagaccgtta aggtcgtgga tgaactcgtc aaagtaatgg gaaggcataa gcccgagaat    2280
atcgttatcg agatggcccg agagaaccaa actacccaga agggacagaa gaacagtagg    2340
gaaaggatga agaggattga agagggtata aaagaactgg ggtcccaaat ccttaaggaa    2400
cacccagttg aaaacaccca gcttcagaat gagaagctct acctgtacta cctgcagaac    2460
ggcagggaca tgtacgtgga tcaggaactg gacatcaatc ggctctccga ctacgacgtg    2520
gatcatatcg tgccccagtc tttttctcaaa gatgattcta ttgataataa agtgttgaca    2580
agatccgata aaaatagagg gaagagtgat aacgtcccct cagaagaagt tgtcaagaaa    2640
atgaaaaatt attggcggca gctgctgaac gccaaactga tcacacaacg gaagttcgat    2700
aatctgacta aggctgaacg aggtggcctg tctgagttgg ataaagccgg cttcatcaaa    2760
aggcagcttg ttgagacacg ccagatcacc aagcacgtgg cccaaattct cgattcacgc    2820
atgaacacca gtacgatga aaatgacaaa ctgattcgag aggtgaaagt tattactctg    2880
aagtctaagc tggtctcaga tttcagaaag gactttcagt tttataaggt gagagagatc    2940
aacaattacc accatgcgca tgatgcctac ctgaatgcag tggtaggcac tgcacttatc    3000
aaaaaatatc ccaagcttga atctgaattt gtttacggag actataaagt gtacgatgtt    3060
aggaaaatga tcgcaaagtc tgagcaggaa ataggcaagg ccaccgctaa gtacttcttt    3120
tacagcaata ttatgaattt tttcaagacc gagattacac tggccaatgg agagattcgg    3180
aagcgaccac ttatcgaaac aaacggagaa acaggagaaa tcgtgtggga caagggtagg    3240
gatttcgcga cagtccggaa ggtcctgtcc atgccgcagg tgaacatcgt taaaaagacc    3300
gaagtacaga ccggaggctt ctccaaggaa agtatcctcc cgaaaaggaa cagcgacaag    3360
ctgatcgcac gcaaaaaaga ttgggacccc aagaaatacg gcggattcga ttctcctaca    3420
gtcgcttaca gtgtactggt tgtggccaaa gtggagaaag ggaagtctaa aaaactcaaa    3480
agcgtcaagg aactgctggg catcacaatc atggagcgat caagcttcga aaaaaacccc    3540
atcgactttc tcgaggcgaa aggatataaa gaggtcaaaa aagacctcat cattaagctt    3600
cccaagtact ctctctttga gcttgaaaac ggccggaaac gaatgctcgc tagtgcgggc    3660
gagctgcaga aaggtaacga gctggcactg ccctctaaat acgttaattt cttgtatctg    3720
```

```
gccagccact atgaaaagct caaagggtct cccgaagata atgagcagaa gcagctgttc    3780
gtggaacaac acaaacacta ccttgatgag atcatcgagc aaataagcga attctccaaa    3840
agagtgatcc tcgccgacgc taacctcgat aaggtgcttt ctgcttacaa taagcacagg    3900
gataagccca tcagggagca ggcagaaaac attatccact tgtttactct gaccaacttg    3960
ggcgcgcctg cagccttcaa gtacttcgac accaccatag acagaaagcg gtacacctct    4020
acaaaggagg tcctggacgc cacactgatt catcagtcaa ttacgggct ctatgaaaca     4080 agaatcgacc tctctcagct cggtggagac agcagggctg accccaagaa gaagaggaag    4140
gtgtga                                                               4146
```

<210> SEQ ID NO 38
<211> LENGTH: 455
<212> TYPE: DNA
<213> ORGANISM: Artificial Sequence
<220> FEATURE:
<223> OTHER INFORMATION: Nucleotide Sequence of RNA Guide Strand for use with Cas9 Endonuclease
<220> FEATURE:
<221> NAME/KEY: misc_feature
<222> LOCATION: (320)..(338)
<223> OTHER INFORMATION: n is a, c, g, or t

<400> SEQUENCE: 38

```
tgtacaaaaa agcaggcttt aaaggaacca attcagtcga ctggatccgg taccaaggtc     60
gggcaggaag agggcctatt tcccatgatt ccttcatatt tgcatatacg atacaaggct    120
gttagagaga taattagaat taatttgact gtaaacacaa agatattagt acaaatacg     180 tgacgtagaa agtaataatt tcttgggtag tttgcagttt taaaattatg ttttaaaatg    240
gactatcata tgcttaccgt aacttgaaag tatttcgatt tcttggcttt atatatcttg    300
tggaaaggac gaaacaccgn nnnnnnnnn nnnnnnnngt tttagagcta gaaatagcaa     360
gttaaaataa ggctagtccg ttatcaactt gaaaaagtgg caccgagtcg gtgcttttt    420 tctagaccca gctttcttgt acaaagttgg catta                                455
```

<210> SEQ ID NO 39
<211> LENGTH: 22
<212> TYPE: DNA
<213> ORGANISM: Artificial Sequence
<220> FEATURE:
<223> OTHER INFORMATION: BCL11A gene target site

<400> SEQUENCE: 39

```
tccaagtgat gtctcggtgg tg                                              22
```

<210> SEQ ID NO 40
<211> LENGTH: 22
<212> TYPE: DNA
<213> ORGANISM: Artificial Sequence
<220> FEATURE:
<223> OTHER INFORMATION: Targeted Homing Endonuclease Target Site

<400> SEQUENCE: 40

```
tttccaatta ttcaaccttt ta                                              22
```

<210> SEQ ID NO 41
<211> LENGTH: 22
<212> TYPE: DNA
<213> ORGANISM: Artificial Sequence
<220> FEATURE:
<223> OTHER INFORMATION: Targeted Homing Endonuclease Target Site

```
<400> SEQUENCE: 41
tcttgaatta ttcaaccttt ta                                              22

<210> SEQ ID NO 42
<211> LENGTH: 22
<212> TYPE: DNA
<213> ORGANISM: Artificial Sequence
<220> FEATURE:
<223> OTHER INFORMATION: Targeted Homing Endonuclease Target Site

<400> SEQUENCE: 42
tttccattta ttcaatattt ta                                              22

<210> SEQ ID NO 43
<211> LENGTH: 22
<212> TYPE: DNA
<213> ORGANISM: Artificial Sequence
<220> FEATURE:
<223> OTHER INFORMATION: Targeted Homing Endonuclease Target Site

<400> SEQUENCE: 43
tttccattta ttcaatatct tt                                              22

<210> SEQ ID NO 44
<211> LENGTH: 12
<212> TYPE: DNA
<213> ORGANISM: Artificial Sequence
<220> FEATURE:
<223> OTHER INFORMATION: U6 Promoter Sequence of a Generic Cas9 Guide
      RNA

<400> SEQUENCE: 44
ggacgaaaca cc                                                         12

<210> SEQ ID NO 45
<211> LENGTH: 20
<212> TYPE: DNA
<213> ORGANISM: Artificial Sequence
<220> FEATURE:
<223> OTHER INFORMATION: Generic Target-specific Sequence of a Generic
      Cas9 Guide RNA
<220> FEATURE:
<221> NAME/KEY: misc_feature
<222> LOCATION: (2)..(20)
<223> OTHER INFORMATION: n is a, c, g, or t

<400> SEQUENCE: 45
gnnnnnnnnn nnnnnnnnnn                                                 20

<210> SEQ ID NO 46
<211> LENGTH: 77
<212> TYPE: DNA
<213> ORGANISM: Artificial Sequence
<220> FEATURE:
<223> OTHER INFORMATION: Guide RNA Scaffold Sequence of a Generic Cas9
      Guide RNA

<400> SEQUENCE: 46
gttttagagc tagaaatagc aagttaaaat aaggctagtc cgttatcaac ttgaaaaagt     60
ggcaccgagt cggtgct                                                    77

<210> SEQ ID NO 47
<211> LENGTH: 10
<212> TYPE: DNA
<213> ORGANISM: Artificial Sequence
<220> FEATURE:
```

```
<223> OTHER INFORMATION: Poly T Tail of a Generic Cas9 Guide RNA
<220> FEATURE:
<221> NAME/KEY: misc_feature
<222> LOCATION: (1)..(4)
<223> OTHER INFORMATION: n is a, c, g, or t

<400> SEQUENCE: 47 nnnntttttt                                                              10

<210> SEQ ID NO 48
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-B

<400> SEQUENCE: 48
gccatttcta ttatcagact tgg                                               23

<210> SEQ ID NO 49
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-C

<400> SEQUENCE: 49
gctgggcttc tgttgcagta ggg                                               23

<210> SEQ ID NO 50
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-D

<400> SEQUENCE: 50
gaaaatggga gacaaatagc tgg                                               23

<210> SEQ ID NO 51
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-E

<400> SEQUENCE: 51
gaataattca agaaaggtgg tgg                                               23

<210> SEQ ID NO 52
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-F

<400> SEQUENCE: 52
gatattgaat aattcaagaa agg                                               23

<210> SEQ ID NO 53
<211> LENGTH: 23
<212> TYPE: DNA
```

```
<213> ORGANISM: Artificial Sequence
<220> FEATURE:
<223> OTHER INFORMATION: Target-specific Sequence for Cas9 Guide RNA
      GGN20GG-G

<400> SEQUENCE: 53
gcctgagatt ctgatcacaa ggg                                          23

<210> SEQ ID NO 54
<211> LENGTH: 23
<212> TYPE: DNA
<213> ORGANISM: Artificial Sequence
<220> FEATURE:
<223> OTHER INFORMATION: Target-specific Sequence for Cas9 Guide RNA
      GGN20GG-H

<400> SEQUENCE: 54
ggtaaattct taaggccatg agg                                          23

<210> SEQ ID NO 55
<211> LENGTH: 22
<212> TYPE: DNA
<213> ORGANISM: Artificial Sequence
<220> FEATURE:
<223> OTHER INFORMATION: Engineered target site

<400> SEQUENCE: 55
ttgaggagat gtctctgtta at                                           22

<210> SEQ ID NO 56
<211> LENGTH: 22
<212> TYPE: DNA
<213> ORGANISM: Artificial Sequence
<220> FEATURE:
<223> OTHER INFORMATION: Engineered target site

<400> SEQUENCE: 56
ttgaggtgat gtctctgtta at                                           22

<210> SEQ ID NO 57
<211> LENGTH: 22
<212> TYPE: DNA
<213> ORGANISM: Artificial Sequence
<220> FEATURE:
<223> OTHER INFORMATION: Engineered target site

<400> SEQUENCE: 57
ttgaagtgat gtctctgtta at                                           22

<210> SEQ ID NO 58
<211> LENGTH: 22
<212> TYPE: DNA
<213> ORGANISM: Artificial Sequence
<220> FEATURE:
<223> OTHER INFORMATION: Engineered target site

<400> SEQUENCE: 58
tccaagtgat gtctctgtta at                                           22

<210> SEQ ID NO 59
<211> LENGTH: 22
<212> TYPE: DNA
<213> ORGANISM: Artificial Sequence
<220> FEATURE:
<223> OTHER INFORMATION: Engineered target site

<400> SEQUENCE: 59
```

```
tccaagtgat gtctctgtta at                                              22
```

<210> SEQ ID NO 60
<211> LENGTH: 22
<212> TYPE: DNA
<213> ORGANISM: Artificial Sequence
<220> FEATURE:
<223> OTHER INFORMATION: Engineered target site

<400> SEQUENCE: 60

```
ttgaggaggt ttctgtgtta at                                              22
```

<210> SEQ ID NO 61
<211> LENGTH: 22
<212> TYPE: DNA
<213> ORGANISM: Artificial Sequence
<220> FEATURE:
<223> OTHER INFORMATION: Engineered target site

<400> SEQUENCE: 61

```
ttgaggaggt ttctcggtgg tg                                              22
```

<210> SEQ ID NO 62
<211> LENGTH: 900
<212> TYPE: DNA
<213> ORGANISM: Artificial Sequence
<220> FEATURE:
<223> OTHER INFORMATION: Nucleotide Sequence of a I-CpaMI homing
       endonuclease; ORF, codon optimized for mammalian expression

<400> SEQUENCE: 62

```
atgaacacca gctctagctt caatccctgg ttcctgaccg gctttagcga tgcagagtgc     60
tctttcagca tcctgataca ggccaacagc aagtactcca ccggttggag gatcaagccc    120
gtgttcgcca tcggcttgca aagaaggac ctggagcttc tgaagagaat ccagagctat    180
ctgggcgtgg gcaagataca cattcacggc aaagacagca ttcagttcag gattgacagc    240
cccaaggagc tggaggtgat catcaaccac tttgagaact acccctggt aaccgccaag    300
tgggccgact acaccctctt taagaaggcc tggacgtaa ttctgttgaa ggagcacctg    360
agccagaagg gcctgcttaa actggtaggc attaaggcga gcctgaatct cgggttgaac    420
ggcagcctca aggaggcgtt cccgaactgg aagaactgc agatcgacag gccgagctac    480
gtgttcaagg gcatccccga ccccaactgg atcagcggct cgcgtcagg cgatagcagc    540
tttaatgtga aaatcagcaa ctcccccacg tcactgctca ataaaagggt gcagctgagg    600
ttcggcatcg gactgaacat cagagagaaa gcccttatcc aatacctggt ggcctacttt    660
gacctgtcag acaacctgaa gaacatctac ttcgacctga cagcgcacg gttcgaggtg    720
gtgaagttca gcgacatcac cgacaagatc atccccttct tcgacaagta cagcatacaa    780
ggcaagaaga gcctggacta catcaacttc aaggaagtgg ccgacattat caagagcaag    840
aaccatctta ctagcgaggg cttccaggaa atcttggaca tcaaagccag tatgaacaag    900
```

<210> SEQ ID NO 63
<211> LENGTH: 300
<212> TYPE: PRT
<213> ORGANISM: Cryphonectria parasitica

<400> SEQUENCE: 63

```
Met Asn Thr Ser Ser Ser Phe Asn Pro Trp Phe Leu Thr Gly Phe Ser
1               5                   10                  15
```

Asp Ala Glu Cys Ser Phe Ser Ile Leu Ile Gln Ala Asn Ser Lys Tyr
            20                  25                  30

Ser Thr Gly Trp Arg Ile Lys Pro Val Phe Ala Ile Gly Leu His Lys
        35                  40                  45

Lys Asp Leu Glu Leu Leu Lys Arg Ile Gln Ser Tyr Leu Gly Val Gly
    50                  55                  60

Lys Ile His Ile His Gly Lys Asp Ser Ile Gln Phe Arg Ile Asp Ser
65                  70                  75                  80

Pro Lys Glu Leu Glu Val Ile Ile Asn His Phe Glu Asn Tyr Pro Leu
                85                  90                  95

Val Thr Ala Lys Trp Ala Asp Tyr Thr Leu Phe Lys Lys Ala Leu Asp
            100                 105                 110

Val Ile Leu Leu Lys Glu His Leu Ser Gln Lys Gly Leu Leu Lys Leu
        115                 120                 125

Val Gly Ile Lys Ala Ser Leu Asn Leu Gly Leu Asn Gly Ser Leu Lys
    130                 135                 140

Glu Ala Phe Pro Asn Trp Glu Glu Leu Gln Ile Asp Arg Pro Ser Tyr
145                 150                 155                 160

Val Phe Lys Gly Ile Pro Asp Pro Asn Trp Ile Ser Gly Phe Ala Ser
                165                 170                 175

Gly Asp Ser Ser Phe Asn Val Lys Ile Ser Asn Ser Pro Thr Ser Leu
            180                 185                 190

Leu Asn Lys Arg Val Gln Leu Arg Phe Gly Ile Gly Leu Asn Ile Arg
        195                 200                 205

Glu Lys Ala Leu Ile Gln Tyr Leu Val Ala Tyr Phe Asp Leu Ser Asp
210                 215                 220

Asn Leu Lys Asn Ile Tyr Phe Asp Leu Asn Ser Ala Arg Phe Glu Val
225                 230                 235                 240

Val Lys Phe Ser Asp Ile Thr Asp Lys Ile Ile Pro Phe Phe Asp Lys
                245                 250                 255

Tyr Ser Ile Gln Gly Lys Lys Ser Leu Asp Tyr Ile Asn Phe Lys Glu
            260                 265                 270

Val Ala Asp Ile Ile Lys Ser Lys Asn His Leu Thr Ser Glu Gly Phe
        275                 280                 285

Gln Glu Ile Leu Asp Ile Lys Ala Ser Met Asn Lys
290                 295                 300

<210> SEQ ID NO 64
<211> LENGTH: 5264
<212> TYPE: DNA
<213> ORGANISM: Artificial Sequence
<220> FEATURE:
<223> OTHER INFORMATION: Nucleotide sequence of BCL11A gene targeting
      nuclease-encoding plasmid pExodusBCL11Ahje

<400> SEQUENCE: 64
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420

| | |
|---|---|
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccactagt ccagtgtggt ggaattctgc | 960 |
| aggtacgttg acgccgccac catgggatat ccatacgatg tcccagatta tgcgccacct | 1020 |
| aagaagaaac gcaaagtccc cggggggcagc acatggacc tgacctacgc ctatctggtc | 1080 |
| ggcctgttcg agggcgacgg ctattttaca atagctaagg ccggcaagta tctgaactac | 1140 |
| gagctgggca tcacactctc catcaaggac gctcagctca tctacaagat caaggacatc | 1200 |
| ctcggcgtgg gcaacgtgta ctttaggaag tacaggcaac atgagatggt cagcctgcga | 1260 |
| atccaggaca aaaccacct gaagaacttc atcctgccca tcttcgacaa gtaccccatg | 1320 |
| ctgagcaaca agcagtacga ctacctgcga ttcaaggatg ccctcctgtc aacatcatc | 1380 |
| tatagcgacg acctgcccga gtacgccagg agcaacgagt caatcaatag cgtggacagc | 1440 |
| atcatcaaca cctcatactt cagcgcctgg ctggttggct tcatcgaggc cgagggctgc | 1500 |
| ttcaccacct acaaggcatc caaggacaag tacctgacag cgggcttctc catagcccag | 1560 |
| aaggacggcg acattctcat ctccgcgatc cacaaatacc tgagcttcac gaccaaaccc | 1620 |
| tacaaagaca agaccaactg tagccacctc aaggtcaccg gcgtgaggag cgtcaataac | 1680 |
| gtggttaagt tcatccaggg tgcgccggtc aagctgctgg gtaacaagaa gctgcagtac | 1740 |
| aaactttgga taaagcagct gcgcaagatc tcccgataca gcgagaaaat ccagctgccc | 1800 |
| agtaactact aatctagagg gcccgtttaa acccgctgat cagcctcgac tgtgccttct | 1860 |
| agttgccagc catctgttgt ttgccccctcc ccgtgccttt ccttgaccct ggaaggtgcc | 1920 |
| actcccactg tccttttccta ataaaatgag gaaattgcat cgcattgtct gagtaggtgt | 1980 |
| cattctattc tggggggtgg ggtggggcag gacagcaagg gggaggattg ggaagacaat | 2040 |
| agcaggcatg ctggggatgc ggtgggctct atggcttctg aggcggaaag aaccagctgg | 2100 |
| ggctctaggg ggtatcccca cgcgccctgt agcggcgcat taagcgcggc gggtgtggtg | 2160 |
| gttacgcgca gcgtgaccgc tacacttgcc agcgccctag cgcccgctcc tttcgctttc | 2220 |
| ttcccttcct ttctcgccac gttcgccggc tttccccgtc aagctctaaa tcggggggctc | 2280 |
| cctttagggt tccgatttag tgctttacgg cacctcgacc ccaaaaaact tgattagggt | 2340 |
| gatggttcac gtagtgggcc atcgccctga tagacggttt ttcgcccttt gacgttggag | 2400 |
| tccacgttct ttaatagtgg actcttgttc caaactggaa caacactcaa ccctatctcg | 2460 |
| gtctattctt ttgatttata agggattttg ccgatttcgg cctattggtt aaaaaatgag | 2520 |
| ctgatttaac aaaaatttaa cgcgaattaa ttctgtggaa tgtgtgtcag ttagggtgtg | 2580 |
| gaaagtcccc aggctcccca gcaggcagaa gtatgcaaag cctatcagga catagcgttg | 2640 |
| gctacccgtg atattgctga agagcttggc ggcgaatggg ctgaccgctt cctcgtgctt | 2700 |
| tacggtatcg ccgctcccga ttcgcagcgc atcgccttct atcgccttct tgacgagttc | 2760 |
| ttctgagcgg gactctgggg ttcgaaatga ccgaccaagc gacgcccaac ctgccatcac | 2820 |

```
gagatttcga ttccaccgcc gccttctatg aaaggttggg cttcggaatc gtttccggg     2880 acgccggctg gatgatcctc cagcgcgggg atctcatgct ggagttcttc gcccacccca     2940
acttgtttat tgcagcttat aatggttaca aataaagcaa tagcatcaca aatttcacaa     3000
ataaagcatt ttttcactg cattctagtt gtggtttgtc caaactcatc aatgtatctt     3060
atcatgtctg tataccgtcg acctctagct agagcttggc gtaatcatgg tcatagctgt     3120
ttcctgtgtg aaattgttat ccgctcacaa ttccacacaa catacgagcc ggaagcataa     3180
agtgtaaagc ctggggtgcc taatgagtga gctaactcac attaattgcg ttgcgctcac     3240
tgcccgcttt ccagtcggga acctgtcgt gccagctgca ttaatgaatc ggccaacgcg     3300
cggggagagg cggtttgcgt attgggcgct cttccgcttc ctcgctcact gactcgctgc     3360
gctcggtcgt tcggctgcgg cgagcggtat cagctcactc aaaggcggta atacggttat     3420
ccacagaatc aggggataac gcaggaaaga acatgtgagc aaaaggccag caaaaggcca     3480
ggaaccgtaa aaaggccgcg ttgctggcgt ttttccatag gctccgcccc cctgacgagc     3540
atcacaaaaa tcgacgctca agtcagaggt ggcgaaaccc gacaggacta taaagatacc     3600
aggcgtttcc ccctggaagc tccctcgtgc gctctcctgt tccgaccctg ccgcttaccg     3660
gatacctgtc cgcctttctc ccttcgggaa gcgtggcgct ttctcatagc tcacgctgta     3720
ggtatctcag ttcggtgtag gtcgttcgct ccaagctggg ctgtgtgcac gaaccccccg     3780
ttcagcccga ccgctgcgcc ttatccggta actatcgtct tgagtccaac ccggtaagac     3840
acgacttatc gccactggca gcagccactg gtaacaggat tagcagagcg aggtatgtag     3900
gcggtgctac agagttcttg aagtggtggc ctaactacgg ctacactaga agaacagtat     3960
ttggtatctg cgctctgctg aagccagtta ccttcggaaa aagagttggt agctcttgat     4020
ccggcaaaca aaccaccgct ggtagcggtt ttttgtttg caagcagcag attacgcgca     4080
gaaaaaaagg atctcaagaa gatcctttga tcttttctac ggggtctgac gctcagtgga     4140
acgaaaactc acgttaaggg attttggtca tgagattatc aaaaaggatc ttcacctaga     4200
tccttttaaa ttaaaaatga agttttaaat caatctaaag tatatatgag taaacttggt     4260
ctgacagtta ccaatgctta atcagtgagg cacctatctc agcgatctgt ctatttcgtt     4320
catccatagt tgcctgactc cccgtcgtgt agataactac gatacgggag gcttaccat     4380 ctggccccag tgctgcaatg ataccgcgag acccacgctc accggctcca gatttatcag     4440
caataaacca gccagccgga agggccgagc gcagaagtgg tcctgcaact ttatccgcct     4500
ccatccagtc tattaattgt tgccgggaag ctagagtaag tagttcgcca gttaatagtt     4560
tgcgcaacgt tgttgccatt gctacaggca tcgtggtgtc acgctcgtcg tttggtatgg     4620
cttcattcag ctccggttcc caacgatcaa ggcgagttac atgatccccc atgttgtgca     4680
aaaaagcggt tagctccttc ggtcctccga tcgttgtcag aagtaagttg gccgcagtgt     4740
tatcactcat ggttatggca gcactgcata attctcttac tgtcatgcca tccgtaagat     4800
gcttttctgt gactggtgag tactcaacca agtcattctg agaatagtgt atgcggcgac     4860
cgagttgctc ttgcccggcg tcaatacggg ataataccgc gccacatagc agaactttaa     4920
aagtgctcat cattggaaaa cgttcttcgg ggcgaaaact ctcaaggatc ttaccgctgt     4980
tgagatccag ttcgatgtaa cccactcgtg cacccaactg atcttcagca tcttttactt     5040
tcaccagcgt ttctgggtga gcaaaaacag gaaggcaaaa tgccgcaaaa aagggaataa     5100
gggcgacacg gaaatgttga atactcatac tcttcctttt tcaatattat tgaagcattt     5160
```

```
atcagggtta ttgtctcatg agcggataca tatttgaatg tatttagaaa aataaacaaa   5220
taggggttcc gcgcacattt ccccgaaaag tgccacctga cgtc                     5264

<210> SEQ ID NO 65
<211> LENGTH: 5100
<212> TYPE: DNA
<213> ORGANISM: Artificial Sequence
<220> FEATURE:
<223> OTHER INFORMATION: Nucleotide sequence of TREX2-encoding plasmid
      pExodus CMV.Trex2

<400> SEQUENCE: 65
gacggatcgg gagatctccc gatcccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgcc ccattgacgc aaatgggcg    780 gtaggcgtgt acggtgggag gtctatataa gcagagctct ctggctaact agagaaccca   840
ctgcttactg gcttatcgaa attaatacga ctcactatag ggagacccaa gctggctagc   900
atgtctgagc cacctcgggc tgagaccttt gtattcctgg acctagaagc cactgggctc   960
ccaaacatgg accctgagat tgcagagata ccctttttg ctgttcaccg ctcttccctg   1020
gagaacccag aacgggatga ttctggttcc ttggtgctgc ccgtgttct ggacaagctc   1080 acactgtgca tgtgcccgga gcgcccctt actgccaagg ccagtgagat tactggtttg   1140
agcagcgaaa gcctgatgca ctgcgggaag gctggtttca tggcgctgt ggtaaggaca   1200 ctgcagggct tcctaagccg caggagggc cccatctgcc ttgtggccca aatggcttc   1260 gattatgact cccactgct gtgcacggag ctacaacgtc tgggtgccca tctgccccaa   1320
gacactgtct gcctggacac actgcctgca ttgcggggcc tggaccgtgc tcacagccac   1380
ggcaccaggg ctcaaggccg caaaagctac agcctggcca gtctcttcca ccgctacttc   1440
caggctgaac ccagtgctgc ccattcagca gaaggtgatg tgcacaccct gcttctgatc   1500
ttcctgcatc gtgctcctga gctgctcgcc tgggcagatg agcaggcccg cagctgggct   1560
catattgagc ccatgtacgt gccacctgat ggtccaagcc tcgaagcctg aattctgcag   1620
atatccagca cagtggcggc cgctcgagtc tagagggccc gtttaaaccc gctgatcagc   1680
ctcgactgtg ccttctagtt gccagccatc tgttgtttgc cctcccccg tgccttcctt   1740 gaccctggaa ggtgccactc ccactgtcct ttcctaataa aatgaggaaa ttgcatcgca   1800
ttgtctgagt aggtgtcatt ctattctggg ggtggggtg gggcaggaca gcaaggggga   1860
ggattgggaa gacaatagca ggcatgctgg ggatgcggtg ggctctatgg cttctgaggc   1920
```

```
ggaaagaacc agctggggct ctaggggta tccccacgcg ccctgtagcg gcgcattaag    1980
cgcggcgggt gtggtggtta cgcgcagcgt gaccgctaca cttgccagcg ccctagcgcc    2040
cgctcctttc gctttcttcc cttcctttct cgccacgttc gccggctttc ccgtcaagc    2100 tctaaatcgg gggctcccctt tagggttccg atttagtgct ttacggcacc tcgaccccaa    2160
aaaacttgat tagggtgatg gttcacgtag tgggccatcg ccctgataga cggttttcg     2220 cccttttgacg ttggagtcca cgttctttaa tagtggactc ttgttccaaa ctggaacaac    2280
actcaaccct atctcggtct attcttttga tttataaggg attttgccga tttcggccta    2340
ttggttaaaa aatgagctga tttaacaaaa attaacgcg aattaattct gtggaatgtg     2400
tgtcagttag ggtgtggaaa gtccccaggc tccccagcag gcagaagtat gcaaagccta    2460
tcaggacata gcgttggcta cccgtgatat tgctgaagag cttggcggcg aatgggctga    2520
ccgcttcctc gtgctttacg gtatcgccgc tcccgattcg cagcgcatcg ccttctatcg    2580
ccttcttgac gagttcttct gagcgggact ctggggttcg aaatgaccga ccaagcgacg    2640
cccaacctgc catcacgaga tttcgattcc accgccgcct tctatgaaag gttgggcttc    2700
ggaatcgttt tccgggacgc cggctggatg atcctccagc gcggggatct catgctggag    2760
ttcttcgccc accccaactt gtttattgca gcttataatg gttacaaata aagcaatagc    2820
atcacaaatt tcacaaataa agcatttttt tcactgcatt ctagttgtgg tttgtccaaa    2880
ctcatcaatg tatcttatca tgtctgtata ccgtcgacct ctagctagag cttggcgtaa    2940
tcatggtcat agctgtttcc tgtgtgaaat tgttatccgc tcacaattcc acacaacata    3000
cgagccggaa gcataaagtg taaagcctgg ggtgcctaat gagtgagcta actcacatta    3060
attgcgttgc gctcactgcc cgctttccag tcgggaaacc tgtcgtgcca gctgcattaa    3120
tgaatcggcc aacgcgcggg gagaggcggt ttgcgtattg ggcgctcttc cgcttcctcg    3180
ctcactgact cgctgcgctc ggtcgttcgg ctgcggcgag cggtatcagc tcactcaaag    3240
gcggtaatac ggttatccac agaatcaggg gataacgcag gaaagaacat gtgagcaaaa    3300
ggccagcaaa aggccaggaa ccgtaaaaag gccgcgttgc tggcgttttt ccataggctc    3360
cgcccccctg acgagcatca caaaaatcga cgctcaagtc agaggtggcg aaacccgaca    3420
ggactataaa gataccaggc gtttccccct ggaagctccc tcgtgcgctc tcctgttccg    3480
accctgccgc ttaccggata cctgtccgcc tttctccctt cgggaagcgt ggcgctttct    3540
catagctcac gctgtaggta tctcagttcg gtgtaggtcg ttcgctccaa gctgggctgt    3600
gtgcacgaac cccccgttca gcccgaccgc tgcgccttat ccggtaacta tcgtcttgag    3660
tccaacccgg taagacacga cttatcgcca ctggcagcag ccactggtaa caggattagc    3720
agagcgaggt atgtaggcgg tgctacagag ttcttgaagt ggtggcctaa ctacggctac    3780
actagaagaa cagtatttgg tatctgcgct ctgctgaagc cagttacctt cggaaaaaga    3840
gttggtagct cttgatccgg caaacaaacc accgctggta gcggtttttt tgtttgcaag    3900
cagcagatta cgcgcagaaa aaaaggatct caagaagatc ctttgatctt ttctacgggg    3960
tctgacgctc agtggaacga aaactcacgt taagggattt tggtcatgag attatcaaaa    4020
aggatcttca cctagatcct tttaaattaa aaatgaagtt ttaaatcaat ctaaagtata    4080
tatgagtaaa cttggtctga cagttaccaa tgcttaatca gtgaggcacc tatctcagcg    4140
atctgtctat ttcgttcatc catagttgcc tgactccccg tcgtgtagat aactacgata    4200
cgggagggct taccatctgg ccccagtgct gcaatgatac gcgagaccc acgctcaccg    4260 gctccagatt tatcagcaat aaaccagcca gccggaaggg ccgagcgcag aagtggtcct    4320
```

```
gcaactttat ccgcctccat ccagtctatt aattgttgcc gggaagctag agtaagtagt    4380
tcgccagtta atagtttgcg caacgttgtt gccattgcta caggcatcgt ggtgtcacgc    4440
tcgtcgtttg gtatggcttc attcagctcc ggttcccaac gatcaaggcg agttacatga    4500
tcccccatgt tgtgcaaaaa agcggttagc tccttcggtc ctccgatcgt tgtcagaagt    4560
aagttggccg cagtgttatc actcatggtt atggcagcac tgcataattc tcttactgtc    4620
atgccatccg taagatgctt ttctgtgact ggtgagtact caaccaagtc attctgagaa    4680
tagtgtatgc ggcgaccgag ttgctcttgc ccggcgtcaa tacgggataa taccgcgcca    4740
catagcagaa ctttaaaagt gctcatcatt ggaaaacgtt cttcggggcg aaaactctca    4800
aggatcttac cgctgttgag atccagttcg atgtaaccca ctcgtgcacc caactgatct    4860
tcagcatctt ttactttcac cagcgtttct gggtgagcaa aaacaggaag gcaaaatgcc    4920
gcaaaaaagg gaataagggc gacacggaaa tgttgaatac tcatactctt ccttttcaa    4980 tattattgaa gcatttatca gggttattgt ctcatgagcg gatacatatt tgaatgtatt    5040
tagaaaaata aacaaatagg ggttccgcgc acatttcccc gaaaagtgcc acctgacgtc    5100
```

<210> SEQ ID NO 66
<211> LENGTH: 20
<212> TYPE: DNA
<213> ORGANISM: Artificial Sequence
<220> FEATURE:
<223> OTHER INFORMATION: PCR Primer

<400> SEQUENCE: 66
gctggaatgg ttgcagtaac                                                20

<210> SEQ ID NO 67
<211> LENGTH: 20
<212> TYPE: DNA
<213> ORGANISM: Artificial Sequence
<220> FEATURE:
<223> OTHER INFORMATION: PCR Primer

<400> SEQUENCE: 67
caaacagcca ttcaccagtg                                                20

<210> SEQ ID NO 68
<211> LENGTH: 21
<212> TYPE: DNA
<213> ORGANISM: Artificial Sequence
<220> FEATURE:
<223> OTHER INFORMATION: PCR Primer

<400> SEQUENCE: 68
ctgccagctc tctaagtctc c                                              21

<210> SEQ ID NO 69
<211> LENGTH: 21
<212> TYPE: DNA
<213> ORGANISM: Artificial Sequence
<220> FEATURE:
<223> OTHER INFORMATION: PCR Primer

<400> SEQUENCE: 69
tgcaacacgc acagaacact c                                              21

What is claimed is:

1. An I-OnuI homing endonuclease (HE) variant that binds to a target site in a fetal hemoglobin (HbF) silencing region set forth in SEQ ID NO: 2,
   wherein the I-OnuI HE variant comprises one or more amino acid substitutions at positions L26, R28, R30, N32, S40, E42, G44, Q46, A70, S72, S78, K80, and T82 set forth in SEQ ID NO: 15;
   wherein the I-OnuI HE variant comprises one or more amino acid substitutions at positions F182, N184, 1186, S190, K191, Q197, V199, S201, K225, K227, D236, V238, and T240 set forth in SEQ ID NO: 15; and
   wherein the I-OnuI HE variant is fused to a TALE DNA binding domain that binds a nucleotide sequence within the HbF silencing region and adjacent to the target site.

2. The I-OnuI HE variant of claim 1, wherein the I-OnuI HE variant further comprises a TREX2 nuclease domain.

3. A polynucleotide encoding the I-OnuI variant of claim 1 or claim 2.

4. A vector comprising the polynucleotide of claim 3.

5. The vector system of claim 4, wherein the vector is selected from the group consisting of an AAV6, a modified adenovirus vector, an integration-deficient lentiviral vector (IDLV), and an integration-deficient foamyviral vector (IDFV).

6. A composition comprising the I-OnuI variant of claim 1 or claim 2.

7. A composition comprising the polynucleotide of claim 3.

8. A cell comprising the I-OnuI variant of claim 1 or claim 2.

9. A cell comprising the polynucleotide of claim 3.

* * * * *